(12) United States Patent
Luthra et al.

(10) Patent No.: US 11,574,514 B2
(45) Date of Patent: Feb. 7, 2023

(54) DIGITAL PASS VERIFICATION SYSTEMS AND METHODS

(71) Applicant: Abbott Laboratories, Abbott Park, IL (US)

(72) Inventors: Nitesh Luthra, Vernon Hills, IL (US); Lev F. Frayman, Maple Grove, MN (US); Terry Finch, Libertyville, IL (US); John Schullian, Cary, IL (US); Douglas Wager, Kansas City, MO (US); Nicholas Alexander Robertson Wood, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 17/476,223

(22) Filed: Sep. 15, 2021

(65) Prior Publication Data

US 2022/0020239 A1 Jan. 20, 2022

Related U.S. Application Data

(63) Continuation of application No. 17/240,644, filed on Apr. 26, 2021, which is a continuation of application
(Continued)

(51) Int. Cl.
*G07C 9/22* (2020.01)
*G16H 10/40* (2018.01)
(Continued)

(52) U.S. Cl.
CPC ............. *G07C 9/22* (2020.01); *G06K 7/1417* (2013.01); *G06K 19/06037* (2013.01);
(Continued)

(58) Field of Classification Search
CPC ........ G16H 40/67; G16H 10/65; G16H 50/80; G16H 10/40; G16H 15/00; G16H 40/63;
(Continued)

(56) References Cited

U.S. PATENT DOCUMENTS

| 4,347,568 A | 8/1982 | Giguere et al. |
| 4,803,625 A | 2/1989 | Fu et al. |

(Continued)

FOREIGN PATENT DOCUMENTS

| AU | 2003226069 | 10/2003 |
| AU | 2011292257 | 1/2013 |

(Continued)

OTHER PUBLICATIONS

United States Patent and Trademark Office, "Notice of Allowance and Fee(s) Due," issued in connection with U.S. Appl. No. 17/208,754, dated Jul. 5, 2022, 9 pages.
(Continued)

*Primary Examiner* — Yong Hang Jiang
(74) *Attorney, Agent, or Firm* — Hanley, Flight & Zimmerman, LLC

(57) ABSTRACT

Digital pass verification systems and methods are disclosed herein. One or more servers are to distribute instructions on a network. The instructions, when executed, cause a first device carried by a person to at least: access a result of a diagnostic test performed on the person, the result provided by a second device; generate a machine-readable code in response to the result being negative; and display the machine-readable code on a display of the first device to enable the person to gain access to a location.

20 Claims, 41 Drawing Sheets

Related U.S. Application Data

No. 17/068,599, filed on Oct. 12, 2020, now Pat. No. 10,991,185.

(60) Provisional application No. 63/080,391, filed on Sep. 18, 2020, provisional application No. 63/054,170, filed on Jul. 20, 2020.

(51) Int. Cl.

| | |
|---|---|
| *G07C 9/25* | (2020.01) |
| *G16H 40/63* | (2018.01) |
| *G06K 7/14* | (2006.01) |
| *G16H 10/65* | (2018.01) |
| *G07C 9/29* | (2020.01) |
| *G06Q 50/26* | (2012.01) |
| *G16H 15/00* | (2018.01) |
| *G16H 50/80* | (2018.01) |
| *G06K 19/06* | (2006.01) |
| *G16H 40/20* | (2018.01) |

(52) U.S. Cl.
CPC ............. *G06Q 50/265* (2013.01); *G07C 9/25* (2020.01); *G07C 9/29* (2020.01); *G16H 10/40* (2018.01); *G16H 10/65* (2018.01); *G16H 15/00* (2018.01); *G16H 40/20* (2018.01); *G16H 40/63* (2018.01); *G16H 50/80* (2018.01)

(58) Field of Classification Search
CPC . G16H 40/20; G07C 9/25; G07C 9/27; G07C 9/22; G07C 9/29; G06Q 50/265; G06K 19/06037; G06K 7/1417
See application file for complete search history.

(56) References Cited

U.S. PATENT DOCUMENTS

| | | | |
|---|---|---|---|
| 4,835,372 A | 5/1989 | Gombrich et al. |
| 4,838,275 A | 6/1989 | Lee |
| 5,171,977 A | 12/1992 | Morrison |
| 5,301,105 A | 4/1994 | Cummings, Jr. |
| 5,502,636 A | 3/1996 | Clarke |
| 5,619,991 A | 4/1997 | Sloane |
| 5,730,124 A | 3/1998 | Yamauchi |
| 5,827,180 A | 10/1998 | Goodman |
| 5,841,975 A | 11/1998 | Layne et al. |
| 5,868,669 A | 2/1999 | Iliff |
| 6,032,119 A | 2/2000 | Brown et al. |
| 6,057,758 A | 5/2000 | Dempsey et al. |
| 6,454,709 B1 | 9/2002 | Kleinschmidt et al. |
| 6,702,988 B1 | 3/2004 | Sagona et al. |
| 6,944,767 B1 | 9/2005 | Judson |
| 7,092,891 B2 | 8/2006 | Maus et al. |
| 7,097,108 B2 | 8/2006 | Zellner et al. |
| 7,278,579 B2 | 10/2007 | Loffredo et al. |
| 7,315,825 B2 | 1/2008 | Rosenfeld et al. |
| 7,392,167 B2 | 6/2008 | Brown |
| 7,565,132 B2 | 7/2009 | Ben Ayed |
| 7,625,763 B2 | 12/2009 | Panotopoulos |
| 7,657,396 B1 | 2/2010 | Brown et al. |
| 7,809,816 B2 | 10/2010 | Johnson et al. |
| 7,811,824 B2 | 10/2010 | Lamont et al. |
| 7,860,725 B2 | 12/2010 | Gopinathan et al. |
| 7,903,152 B2 | 3/2011 | Kim |
| 7,908,153 B2 | 3/2011 | Scherpbier et al. |
| 7,917,377 B2 | 3/2011 | Rao et al. |
| 7,943,381 B2 | 5/2011 | Lappe et al. |
| 7,945,670 B2 * | 5/2011 | Nakamura ............ H04L 63/104 709/226 |
| 7,977,103 B2 | 7/2011 | Martin et al. |
| 7,993,266 B2 | 8/2011 | Colston, Jr. et al. |
| 8,043,224 B2 | 10/2011 | Sarel |
| 8,111,151 B2 | 2/2012 | Zhu et al. |
| 8,131,478 B2 | 3/2012 | Kai |
| 8,147,426 B2 | 4/2012 | Neel et al. |
| 8,211,715 B1 | 7/2012 | Royds |
| 8,234,222 B2 | 7/2012 | Thompson et al. |
| 8,306,831 B2 | 11/2012 | Eisenberger et al. |
| 8,380,541 B1 | 2/2013 | Holmes |
| 8,423,385 B2 | 4/2013 | Radoccia et al. |
| 8,423,435 B1 | 4/2013 | Poteet et al. |
| 8,510,129 B2 | 8/2013 | Morris |
| 8,527,209 B2 | 9/2013 | Hyde et al. |
| 8,531,291 B2 | 9/2013 | Tran |
| 8,560,339 B2 | 10/2013 | Khan |
| 8,577,697 B2 | 11/2013 | Demopulos |
| 8,597,190 B2 | 12/2013 | Rule et al. |
| 8,603,832 B2 | 12/2013 | Whitesides et al. |
| 8,651,383 B2 | 2/2014 | Litz et al. |
| 8,737,971 B2 | 5/2014 | van Rooyen et al. |
| 8,764,655 B2 | 7/2014 | Yoo |
| 8,805,698 B2 | 8/2014 | Stiles et al. |
| 8,821,810 B2 | 9/2014 | Whitesides et al. |
| 8,881,040 B2 | 11/2014 | Li |
| 8,899,478 B2 | 12/2014 | Rowlandson et al. |
| 8,930,178 B2 | 1/2015 | Pestian et al. |
| 8,954,719 B2 | 2/2015 | Dicks et al. |
| 8,996,314 B2 | 3/2015 | Ohnemus et al. |
| 9,041,530 B2 | 5/2015 | Sprigg et al. |
| 9,060,683 B2 | 6/2015 | Tran |
| 9,072,425 B1 | 7/2015 | Bogema |
| 9,076,142 B2 | 7/2015 | Adolphe |
| 9,083,546 B2 | 7/2015 | Sadhu |
| 9,141,762 B2 | 9/2015 | Lev et al. |
| 9,147,092 B2 | 9/2015 | Jeng et al. |
| 9,161,716 B2 | 10/2015 | Estocado |
| 9,185,200 B2 | 11/2015 | Cunningham |
| 9,208,672 B2 | 12/2015 | Patil et al. |
| 9,241,663 B2 | 1/2016 | Jena et al. |
| 9,268,911 B2 | 2/2016 | Sia et al. |
| 9,310,300 B2 | 4/2016 | Alt et al. |
| 9,390,458 B2 | 7/2016 | Sarkis, Jr. et al. |
| 9,414,776 B2 | 8/2016 | Sillay et al. |
| 9,436,924 B2 | 9/2016 | Kokic et al. |
| 9,460,263 B2 | 10/2016 | Holmes et al. |
| 9,485,345 B2 | 11/2016 | Dantu et al. |
| 9,489,703 B2 | 11/2016 | Kauniskangas et al. |
| 9,500,865 B2 | 11/2016 | Chen |
| 9,524,372 B2 | 12/2016 | Hengstler et al. |
| 9,597,016 B2 | 3/2017 | Stone et al. |
| 9,653,002 B2 | 5/2017 | Alberts et al. |
| 9,658,152 B2 | 5/2017 | Zimmerle et al. |
| 9,713,425 B2 | 7/2017 | Gross et al. |
| 9,715,579 B2 | 7/2017 | Hengstler et al. |
| 9,727,702 B2 | 8/2017 | Kass-Hout et al. |
| 9,782,075 B2 | 10/2017 | Redei |
| 9,787,815 B2 | 10/2017 | Erickson et al. |
| 9,805,165 B2 | 10/2017 | Xiang et al. |
| 9,857,373 B1 | 1/2018 | Pulitzer et al. |
| 9,886,750 B2 | 2/2018 | Price et al. |
| 9,903,857 B2 | 2/2018 | Polwart et al. |
| 9,974,485 B2 | 5/2018 | Robertson |
| 9,977,870 B2 | 5/2018 | Hanina et al. |
| 9,983,197 B2 | 5/2018 | Lin et al. |
| 9,989,952 B2 | 6/2018 | Ghazizadeh |
| 9,999,385 B2 | 6/2018 | Copeland et al. |
| 10,012,019 B2 | 7/2018 | Veerasamy et al. |
| 10,026,508 B2 | 7/2018 | Silva et al. |
| 10,031,076 B2 | 7/2018 | Mucci et al. |
| 10,042,016 B2 | 8/2018 | Hanada et al. |
| 10,043,590 B2 | 8/2018 | Karvela et al. |
| 10,052,010 B2 | 8/2018 | Feddema |
| 10,062,020 B2 | 8/2018 | Oron |
| 10,078,875 B2 | 9/2018 | Powell et al. |
| 10,092,007 B2 | 10/2018 | Pierce et al. |
| 10,102,017 B2 | 10/2018 | Ganguly et al. |
| 10,122,010 B2 | 11/2018 | Tajima et al. |
| 10,129,450 B2 | 11/2018 | Nabhan |
| 10,132,743 B2 | 11/2018 | Lenigk et al. |
| 10,132,794 B2 | 11/2018 | Chou et al. |
| 10,152,013 B2 | 12/2018 | Kusano et al. |
| 10,152,702 B2 | 12/2018 | Ingber |
| 10,182,770 B2 | 1/2019 | Asianto et al. |

(56) References Cited

U.S. PATENT DOCUMENTS

| | | |
|---|---|---|
| 10,188,323 B2 | 1/2019 | Sales et al. |
| 10,202,015 B2 | 2/2019 | Halbauer |
| 10,202,020 B2 | 2/2019 | Hattori |
| 10,219,739 B2 | 3/2019 | Mestha et al. |
| 10,242,515 B2 | 3/2019 | Novero et al. |
| 10,252,011 B2 | 4/2019 | Garde et al. |
| 10,267,742 B2 | 4/2019 | Khan |
| 10,269,451 B2 | 4/2019 | Walker |
| 10,271,998 B2 | 4/2019 | LaVon et al. |
| 10,272,020 B2 | 4/2019 | Jolliff et al. |
| 10,297,354 B2 | 5/2019 | Craine et al. |
| 10,303,843 B2 | 5/2019 | Bitran et al. |
| 10,303,851 B2 | 5/2019 | Nguyen et al. |
| 10,312,017 B2 | 6/2019 | Huang et al. |
| 10,321,065 B2 | 6/2019 | Shi |
| 10,324,009 B2 | 6/2019 | Chou et al. |
| 10,325,070 B2 | 6/2019 | Beale et al. |
| 10,331,924 B2 | 6/2019 | Pulitzer et al. |
| 10,349,893 B2 | 7/2019 | Lee et al. |
| 10,352,920 B2 | 7/2019 | Ehrenkranz |
| 10,372,877 B2 | 8/2019 | Merkin |
| 10,410,308 B2 | 9/2019 | Abousy et al. |
| 10,430,552 B2 | 10/2019 | Mihai |
| 10,470,670 B2 | 11/2019 | Smith |
| 10,473,659 B2 | 11/2019 | Pulitzer et al. |
| 10,475,533 B2 | 11/2019 | Hanina et al. |
| 10,534,116 B2 | 1/2020 | Darty |
| 10,534,903 B2 | 1/2020 | Trelin |
| 10,561,317 B2 | 2/2020 | Kambham |
| 10,586,617 B1 | 3/2020 | Mair |
| 10,602,987 B2 | 3/2020 | Khachaturian et al. |
| 10,605,816 B1 | 3/2020 | Koo et al. |
| 10,607,732 B2 | 3/2020 | Xing et al. |
| 10,613,082 B2 | 4/2020 | Ehrenkranz |
| 10,629,311 B2 | 4/2020 | Shaya |
| 10,632,342 B2 | 4/2020 | Quy |
| 10,635,870 B2 | 4/2020 | Pulitzer et al. |
| 10,636,527 B2 | 4/2020 | Pulitzer et al. |
| 10,638,957 B2 | 5/2020 | Mirza |
| 10,641,766 B2 | 5/2020 | Mudanyali et al. |
| 10,645,472 B1 | 5/2020 | Manzella et al. |
| 10,650,916 B2 | 5/2020 | Moturu et al. |
| 10,660,522 B2 | 5/2020 | Redei |
| 10,663,466 B2 | 5/2020 | Ozcan et al. |
| 10,664,486 B2 | 5/2020 | Fonesca et al. |
| 10,681,516 B2 | 6/2020 | Zin et al. |
| 10,706,966 B2 | 7/2020 | Hengstler et al. |
| 10,712,199 B2 | 7/2020 | Won et al. |
| 10,732,169 B2 | 8/2020 | Leung |
| 10,734,099 B2 | 8/2020 | Evans et al. |
| 10,753,861 B2 | 8/2020 | Zaccari et al. |
| 10,768,185 B2 | 9/2020 | Klapperich et al. |
| 10,769,489 B2 | 9/2020 | Nahum et al. |
| 10,772,552 B2 | 9/2020 | Bedell, Jr. |
| 10,776,772 B2 | 9/2020 | Vityaz |
| 10,776,804 B2 | 9/2020 | Avallone et al. |
| 10,777,308 B2 | 9/2020 | Kutty |
| 10,777,325 B1 | 9/2020 | Li |
| 10,777,326 B2 | 9/2020 | Shaya |
| 10,780,224 B2 | 9/2020 | Handler |
| 10,783,546 B2 | 9/2020 | Llewelyn |
| 10,783,988 B1 | 9/2020 | Atkin |
| 10,789,555 B2 | 9/2020 | Experton |
| 10,796,559 B2 | 10/2020 | Kusens |
| 10,810,518 B2 | 10/2020 | Block et al. |
| 10,818,379 B2 | 10/2020 | Krishnan et al. |
| 10,824,825 B2 | 11/2020 | Jinedatha |
| 10,830,761 B2 | 11/2020 | Chou et al. |
| 10,835,122 B2 | 11/2020 | Pulitzer et al. |
| 10,841,737 B2 | 11/2020 | Millius |
| 10,841,775 B2 | 11/2020 | Barash et al. |
| 10,867,700 B2 | 12/2020 | Marshall |
| 10,887,104 B1 | 1/2021 | Jayachandran et al. |
| 10,888,283 B1 | 1/2021 | Benjauthrit et al. |
| 10,890,534 B2 | 1/2021 | Pulitzer et al. |
| 10,902,308 B2 | 1/2021 | Gire et al. |
| 10,915,505 B2 | 2/2021 | Soni et al. |
| 10,923,216 B1 | 2/2021 | White et al. |
| 10,923,231 B2 | 2/2021 | Kelly et al. |
| 10,929,509 B2 | 2/2021 | Raja |
| 10,930,381 B2 | 2/2021 | Pulitzer et al. |
| 10,931,643 B1 | 2/2021 | Neumann |
| 10,936,698 B2 | 3/2021 | Hodge |
| 10,937,296 B1 | 3/2021 | Kukreja et al. |
| 10,991,185 B1 | 4/2021 | Luthra et al. |
| 10,991,190 B1 | 4/2021 | Luthra et al. |
| 11,151,820 B1 | 10/2021 | Klein et al. |
| 2001/0039502 A1 | 11/2001 | Case |
| 2001/0041991 A1 | 11/2001 | Segal et al. |
| 2002/0059030 A1 | 5/2002 | Otworth et al. |
| 2002/0099572 A1 | 7/2002 | Dyckman et al. |
| 2002/0177759 A1 | 11/2002 | Schoenberg et al. |
| 2003/0036683 A1 | 2/2003 | Kehr et al. |
| 2003/0196097 A1 | 10/2003 | Korosec et al. |
| 2003/0217037 A1 | 11/2003 | Bicker et al. |
| 2004/0010425 A1 | 1/2004 | Wilkes et al. |
| 2004/0157612 A1 | 8/2004 | Kim |
| 2004/0166550 A1 | 8/2004 | Sullivan et al. |
| 2004/0225527 A1 | 11/2004 | Holz |
| 2005/0060174 A1 | 3/2005 | Heyward et al. |
| 2005/0137481 A1 | 6/2005 | Sheard et al. |
| 2005/0203353 A1 | 9/2005 | Ma et al. |
| 2005/0277872 A1 | 12/2005 | Colby, Jr. et al. |
| 2006/0009702 A1 | 1/2006 | Iwaki et al. |
| 2006/0022834 A1 | 2/2006 | Rosenfeld et al. |
| 2006/0031101 A1 | 2/2006 | Ross |
| 2006/0036619 A1 | 2/2006 | Fuerst et al. |
| 2006/0094028 A1 | 5/2006 | Danna et al. |
| 2006/0106646 A1 | 5/2006 | Squilla et al. |
| 2006/0154642 A1 | 7/2006 | Scannell, Jr. |
| 2006/0165040 A1 | 7/2006 | Rathod et al. |
| 2006/0218010 A1 | 9/2006 | Michon et al. |
| 2006/0222567 A1 | 10/2006 | Kloepfer et al. |
| 2007/0002791 A1 | 1/2007 | Kasprzyk et al. |
| 2007/0004969 A1 | 1/2007 | Kong et al. |
| 2007/0043694 A1 | 2/2007 | Sawafta et al. |
| 2007/0078689 A1 | 4/2007 | Zubak et al. |
| 2007/0092871 A1 | 4/2007 | Lodes et al. |
| 2007/0138253 A1 | 6/2007 | Libin et al. |
| 2007/0156456 A1 | 7/2007 | McGillin et al. |
| 2007/0179810 A1 | 8/2007 | Goodman |
| 2007/0222599 A1 | 9/2007 | Coveley et al. |
| 2007/0229290 A1 | 10/2007 | Kahn et al. |
| 2007/0239487 A1 | 10/2007 | Abraham-Fuchs et al. |
| 2007/0276702 A1 | 11/2007 | Dani |
| 2007/0298436 A1 | 12/2007 | Lappe |
| 2009/0180927 A1 | 7/2009 | Petruno et al. |
| 2009/0221059 A1 | 9/2009 | Williams et al. |
| 2009/0325276 A1 | 12/2009 | Battrell et al. |
| 2010/0021937 A1 | 1/2010 | Greenberg et al. |
| 2010/0039259 A1* | 2/2010 | Hazzani .............. G08B 21/22 340/541 |
| 2010/0042394 A1 | 2/2010 | Khan |
| 2010/0169220 A1 | 7/2010 | Choing et al. |
| 2010/0255795 A1 | 10/2010 | Rubinsky et al. |
| 2010/0257027 A1 | 10/2010 | Greenberg et al. |
| 2010/0268057 A1 | 10/2010 | Firminger et al. |
| 2010/0279718 A1 | 11/2010 | Borve |
| 2011/0004488 A1 | 1/2011 | Benja-Athon |
| 2011/0084132 A1 | 4/2011 | Tofighbakhsh |
| 2011/0172550 A1 | 7/2011 | Martin et al. |
| 2011/0183351 A1 | 7/2011 | Hyde et al. |
| 2011/0270631 A1 | 11/2011 | Cambray et al. |
| 2012/0035279 A1 | 2/2012 | Miller |
| 2012/0091202 A1* | 4/2012 | Cohen ............... H04M 1/72403 235/382 |
| 2012/0109688 A1 | 5/2012 | Yoo |
| 2012/0123686 A1 | 5/2012 | Xiang et al. |
| 2012/0190132 A1 | 7/2012 | McAleer |
| 2012/0190936 A1 | 7/2012 | Rao et al. |
| 2012/0265702 A1 | 10/2012 | Maher |
| 2012/0284046 A1 | 11/2012 | Baym et al. |
| 2012/0284047 A1 | 11/2012 | Baym et al. |
| 2013/0013333 A1 | 1/2013 | Gopinathan et al. |

(56) References Cited

U.S. PATENT DOCUMENTS

| | | |
|---|---|---|
| 2013/0138451 A1 | 5/2013 | Shiono et al. |
| 2013/0203043 A1 | 8/2013 | Ozcan et al. |
| 2013/0218588 A1 | 8/2013 | Kehr et al. |
| 2013/0310671 A1 | 11/2013 | Goodnow |
| 2014/0006051 A1 | 1/2014 | Vuong et al. |
| 2014/0012599 A1 | 1/2014 | Weiss |
| 2014/0014720 A1 | 1/2014 | Sarkis, Jr. et al. |
| 2014/0016977 A1 | 1/2014 | Kakitani et al. |
| 2014/0017643 A1 | 1/2014 | Sady |
| 2014/0186294 A1 | 7/2014 | Gardai et al. |
| 2014/0210968 A1 | 7/2014 | Kauniskangas et al. |
| 2014/0242612 A1 | 8/2014 | Wang et al. |
| 2014/0249394 A1 | 9/2014 | Maus et al. |
| 2014/0250205 A1 | 9/2014 | Kauniskangas et al. |
| 2014/0257047 A1 | 9/2014 | Sillay et al. |
| 2014/0257058 A1 | 9/2014 | Clarysse et al. |
| 2014/0272928 A1 | 9/2014 | Rey et al. |
| 2014/0315229 A1 | 10/2014 | Karlsson et al. |
| 2014/0324373 A1 | 10/2014 | Xiang et al. |
| 2014/0330579 A1 | 11/2014 | Cashman et al. |
| 2014/0335505 A1 | 11/2014 | Holmes |
| 2015/0036131 A1 | 2/2015 | Salsman |
| 2015/0070187 A1 | 3/2015 | Wiesner et al. |
| 2015/0106118 A1 | 4/2015 | Melo et al. |
| 2015/0119652 A1 | 4/2015 | Hyde et al. |
| 2015/0164323 A1 | 6/2015 | Holtzclaw |
| 2015/0177147 A1 | 6/2015 | Mangan et al. |
| 2015/0223057 A1 | 8/2015 | Dellarciprete et al. |
| 2015/0269325 A1 | 9/2015 | Ohta et al. |
| 2015/0324526 A1 | 11/2015 | Cambray et al. |
| 2015/0379206 A1 | 12/2015 | Villare |
| 2016/0029957 A1 | 2/2016 | Faybishenko et al. |
| 2016/0063215 A1 | 3/2016 | Zamer |
| 2016/0077091 A1 | 3/2016 | Tyrrell et al. |
| 2016/0178607 A1 | 6/2016 | Husheer et al. |
| 2016/0189174 A1 | 6/2016 | Heath |
| 2016/0196391 A1 | 7/2016 | Peak et al. |
| 2016/0210416 A1 | 7/2016 | Whitehurst |
| 2016/0262689 A1 | 9/2016 | Batista |
| 2016/0267295 A1 | 9/2016 | Gervais et al. |
| 2016/0292393 A1 | 10/2016 | Balwani |
| 2016/0300021 A1 | 10/2016 | Abbott |
| 2016/0321480 A1 | 11/2016 | Hamlin et al. |
| 2016/0365006 A1 | 12/2016 | Minturn |
| 2016/0367188 A1 | 12/2016 | Malik et al. |
| 2016/0367194 A1 | 12/2016 | Murphy |
| 2017/0000359 A1 | 1/2017 | Kohli et al. |
| 2017/0007126 A1 | 1/2017 | Shahar |
| 2017/0021356 A1 | 1/2017 | Dority et al. |
| 2017/0023542 A1 | 1/2017 | Wang et al. |
| 2017/0023556 A1 | 1/2017 | Shevkoplyas et al. |
| 2017/0024531 A1 | 1/2017 | Malaviya |
| 2017/0027424 A1 | 2/2017 | Ferren et al. |
| 2017/0027482 A1 | 2/2017 | Zilberstein et al. |
| 2017/0055111 A1 | 2/2017 | Nazareth et al. |
| 2017/0055878 A1 | 3/2017 | Chon et al. |
| 2017/0068785 A1 | 3/2017 | Experton et al. |
| 2017/0068794 A1 | 3/2017 | Pagels et al. |
| 2017/0124263 A1 | 5/2017 | Crafts, Jr. et al. |
| 2017/0140120 A1 | 5/2017 | Thrower |
| 2017/0168051 A1 | 6/2017 | Lui et al. |
| 2017/0177797 A1 | 6/2017 | Kumiawan et al. |
| 2017/0188938 A1 | 7/2017 | Toh et al. |
| 2017/0193198 A1 | 7/2017 | Kamatani et al. |
| 2017/0248592 A1 | 8/2017 | Wang et al. |
| 2017/0262604 A1 | 9/2017 | Francois |
| 2017/0270253 A1 | 9/2017 | Haider |
| 2017/0293730 A1 | 10/2017 | Fish et al. |
| 2017/0308679 A1 | 10/2017 | Murray |
| 2017/0308779 A1 | 10/2017 | Thuries et al. |
| 2017/0323070 A1 | 11/2017 | Hodge |
| 2017/0323285 A1 | 11/2017 | Xing |
| 2017/0323441 A1 | 11/2017 | Shah et al. |
| 2018/0004910 A1 | 1/2018 | Xiang et al. |
| 2018/0011973 A1 | 1/2018 | Fish et al. |
| 2018/0032757 A1 | 2/2018 | Michael |
| 2018/0042559 A1 | 2/2018 | Cabrera, Jr. et al. |
| 2018/0046772 A1 | 2/2018 | Mitteldorf |
| 2018/0089376 A1 | 3/2018 | Tucker et al. |
| 2018/0106789 A1 | 4/2018 | Pulitzer et al. |
| 2018/0107802 A1 | 4/2018 | Satterwhite et al. |
| 2018/0108430 A1 | 4/2018 | Vo et al. |
| 2018/0108434 A1 | 4/2018 | Freedman |
| 2018/0121625 A1 | 5/2018 | Barker |
| 2018/0143215 A1 | 5/2018 | Chang et al. |
| 2018/0150600 A1 | 5/2018 | Astigarraga et al. |
| 2018/0165417 A1 | 6/2018 | Hall et al. |
| 2018/0166155 A1 | 6/2018 | Pulitzer et al. |
| 2018/0166171 A1 | 6/2018 | Pulitzer et al. |
| 2018/0166177 A1 | 6/2018 | Pulitzer et al. |
| 2018/0174689 A1 | 6/2018 | Pulitzer et al. |
| 2018/0196193 A1 | 7/2018 | Ozcan et al. |
| 2018/0197623 A1 | 7/2018 | Sim |
| 2018/0218124 A1 | 8/2018 | Gorelick et al. |
| 2018/0226158 A1 | 8/2018 | Fish et al. |
| 2018/0267759 A1 | 9/2018 | Llewelyn |
| 2018/0276651 A1 | 9/2018 | Gauli et al. |
| 2018/0277252 A1 | 9/2018 | Drenkard et al. |
| 2018/0278691 A1 | 9/2018 | Vergara, Jr. |
| 2018/0299468 A1 | 10/2018 | Kelleher |
| 2018/0303344 A1 | 10/2018 | Huber et al. |
| 2018/0305773 A1 | 10/2018 | Abudayyeh et al. |
| 2018/0308569 A1 | 10/2018 | Luellen |
| 2018/0308585 A1 | 10/2018 | Holmes et al. |
| 2018/0317769 A1 | 11/2018 | Khan |
| 2018/0330804 A1 | 11/2018 | Hiruta et al. |
| 2018/0356407 A1 | 12/2018 | Ehrenkranz et al. |
| 2018/0358117 A1 | 12/2018 | Neagle |
| 2018/0360675 A1 | 12/2018 | Darrah et al. |
| 2018/0364224 A1 | 12/2018 | Pulitzer et al. |
| 2018/0366230 A1 | 12/2018 | Pulitzer et al. |
| 2018/0372669 A1 | 12/2018 | Javitt et al. |
| 2018/0372755 A1 | 12/2018 | Gehrke et al. |
| 2018/0374582 A1 | 12/2018 | Holmes et al. |
| 2019/0014996 A1 | 1/2019 | Qian et al. |
| 2019/0019578 A1 | 1/2019 | Vaccaro |
| 2019/0027250 A1 | 1/2019 | Pulitzer et al. |
| 2019/0027251 A1 | 1/2019 | Pulitzer et al. |
| 2019/0027258 A1 | 1/2019 | Pulitzer et al. |
| 2019/0027259 A1 | 1/2019 | Pulitzer et al. |
| 2019/0034591 A1 | 1/2019 | Mossin et al. |
| 2019/0035491 A1 | 1/2019 | Pulitzer et al. |
| 2019/0035499 A1 | 1/2019 | Daya |
| 2019/0038148 A1 | 2/2019 | Valys et al. |
| 2019/0054347 A1 | 2/2019 | Saigh et al. |
| 2019/0080789 A1 | 3/2019 | Kloosterman |
| 2019/0086400 A1 | 3/2019 | Ehrenkranz |
| 2019/0088373 A1 | 3/2019 | Sarmentero |
| 2019/0095587 A1 | 3/2019 | Warner et al. |
| 2019/0095957 A1 | 3/2019 | Ibarria et al. |
| 2019/0096516 A1 | 3/2019 | Pulitzer et al. |
| 2019/0108898 A1 | 4/2019 | Gulati |
| 2019/0113520 A1 | 4/2019 | Blume et al. |
| 2019/0117069 A1 | 4/2019 | Johnson |
| 2019/0122768 A1 | 4/2019 | Pulitzer et al. |
| 2019/0122771 A1 | 4/2019 | Pulitzer et al. |
| 2019/0128816 A1 | 5/2019 | Chou et al. |
| 2019/0147997 A1 | 5/2019 | Pulitzer et al. |
| 2019/0156937 A1 | 5/2019 | Shimomura et al. |
| 2019/0170734 A1 | 6/2019 | Chou et al. |
| 2019/0187140 A1 | 6/2019 | Kamei et al. |
| 2019/0229907 A1 | 7/2019 | Nicolson et al. |
| 2019/0237195 A1 | 8/2019 | Berberian et al. |
| 2019/0244695 A1 | 8/2019 | Dejima et al. |
| 2019/0279777 A1 | 9/2019 | Conlin et al. |
| 2019/0287671 A1 | 9/2019 | Mako et al. |
| 2019/0294919 A1 | 9/2019 | Nahum et al. |
| 2019/0320900 A1 | 10/2019 | Majmudar |
| 2019/0343386 A1 | 11/2019 | Pulitzer et al. |
| 2019/0346369 A1 | 11/2019 | Ozcan et al. |
| 2019/0355451 A1 | 11/2019 | Clark |
| 2019/0362841 A1 | 11/2019 | Aysin et al. |
| 2019/0362852 A1 | 11/2019 | Von Berg et al. |
| 2019/0369126 A1 | 12/2019 | Nguyen et al. |

(56) References Cited

U.S. PATENT DOCUMENTS

| | | |
|---|---|---|
| 2019/0370576 A1 | 12/2019 | Surendran et al. |
| 2019/0374152 A1 | 12/2019 | Wayne et al. |
| 2019/0376966 A1 | 12/2019 | Pulitzer et al. |
| 2019/0384890 A1 | 12/2019 | Pulitzer et al. |
| 2020/0026401 A1 | 1/2020 | Krimsky et al. |
| 2020/0029837 A1 | 1/2020 | Joudi |
| 2020/0043586 A1 | 2/2020 | Teucher et al. |
| 2020/0066381 A1 | 2/2020 | Johnson |
| 2020/0066415 A1 | 2/2020 | Hettig et al. |
| 2020/0090794 A1 | 3/2020 | Jung et al. |
| 2020/0090801 A1 | 3/2020 | Scott et al. |
| 2020/0090805 A1 | 3/2020 | Bowers et al. |
| 2020/0098461 A1 | 3/2020 | Macoviak et al. |
| 2020/0105409 A1 | 4/2020 | Kochar et al. |
| 2020/0107787 A1 | 4/2020 | Sarkaria et al. |
| 2020/0118164 A1 | 4/2020 | DeFrank et al. |
| 2020/0125965 A1 | 4/2020 | Benja-Athon |
| 2020/0132662 A1 | 4/2020 | Hengstler et al. |
| 2020/0150049 A1 | 5/2020 | Pulitzer et al. |
| 2020/0152339 A1 | 5/2020 | Pulitzer et al. |
| 2020/0159957 A1 | 5/2020 | Reimers |
| 2020/0164373 A1 | 5/2020 | Khattak et al. |
| 2020/0167871 A1 | 5/2020 | Basu et al. |
| 2020/0176124 A1 | 6/2020 | Chatterjea et al. |
| 2020/0183137 A1 | 6/2020 | Hu et al. |
| 2020/0204370 A1 | 6/2020 | Wisniewski |
| 2020/0204377 A1 | 6/2020 | Wisniewski |
| 2020/0254445 A1 | 8/2020 | Chou et al. |
| 2020/0257103 A1 | 8/2020 | Fletcher et al. |
| 2020/0260992 A1 | 8/2020 | Mirza |
| 2020/0278297 A1 | 9/2020 | Karlovac et al. |
| 2020/0279339 A1 | 9/2020 | Akutagawa et al. |
| 2020/0279464 A1 | 9/2020 | Llewelyn |
| 2020/0279585 A1 | 9/2020 | Rothschild |
| 2020/0279631 A1 | 9/2020 | Bass et al. |
| 2020/0279642 A1 | 9/2020 | Lee et al. |
| 2020/0279657 A1 | 9/2020 | Lee et al. |
| 2020/0281469 A1 | 9/2020 | Redei |
| 2020/0286606 A1 | 9/2020 | Sy |
| 2020/0291490 A1 | 9/2020 | Jolly et al. |
| 2020/0303044 A1 | 9/2020 | Stephen |
| 2020/0304944 A1 | 9/2020 | Millius et al. |
| 2020/0312428 A1 | 10/2020 | Reeves et al. |
| 2020/0321090 A1 | 10/2020 | Sonbol et al. |
| 2020/0327986 A1 | 10/2020 | Kurniawan et al. |
| 2020/0330029 A1 | 10/2020 | Chou et al. |
| 2020/0330979 A1 | 10/2020 | Cyr et al. |
| 2020/0333312 A1 | 10/2020 | Islam |
| 2020/0334811 A1 | 10/2020 | Mansi et al. |
| 2020/0335219 A1 | 10/2020 | Fogel |
| 2020/0337794 A1 | 10/2020 | Hall et al. |
| 2020/0340988 A1 | 10/2020 | Ehrenkranz |
| 2020/0340989 A1 | 10/2020 | Rurack et al. |
| 2020/0342980 A1 | 10/2020 | Westin et al. |
| 2020/0345316 A1 | 11/2020 | Noel |
| 2020/0350079 A1 | 11/2020 | Thomas et al. |
| 2020/0350989 A1 | 11/2020 | Llewelyn |
| 2020/0357497 A1 | 11/2020 | Kamber Todd |
| 2020/0357512 A1 | 11/2020 | Coghlan |
| 2020/0357526 A1 | 11/2020 | Odiz et al. |
| 2020/0363408 A1 | 11/2020 | Chou et al. |
| 2020/0397935 A1 | 12/2020 | Church et al. |
| 2020/0402671 A1 | 12/2020 | Shaw |
| 2021/0012869 A1 | 1/2021 | Kotlarz et al. |
| 2021/0043288 A1 | 2/2021 | Nakanishi |
| 2021/0043326 A1 | 2/2021 | Janssen |
| 2021/0043330 A1 | 2/2021 | Ikeshima |
| 2021/0050116 A1 | 2/2021 | Sabeti et al. |
| 2021/0056639 A1 | 2/2021 | Eberting |
| 2021/0057074 A1 | 2/2021 | Wearne |
| 2021/0057111 A1 | 2/2021 | Barkol et al. |
| 2021/0058736 A1 | 2/2021 | Ghazzaoui et al. |
| 2021/0248853 A1* | 8/2021 | Vilhelmsen ............... G07C 9/27 |
| 2021/0286864 A1* | 9/2021 | Burke ..................... G06F 21/32 |
| 2021/0287768 A1* | 9/2021 | Craig ..................... G16H 10/60 |
| 2021/0326474 A1 | 10/2021 | Sparks et al. |
| 2021/0350649 A1 | 11/2021 | Jafri |
| 2021/0358068 A1 | 11/2021 | Boszczyk et al. |
| 2022/0020236 A1 | 1/2022 | Luthra et al. |
| 2022/0020237 A1 | 1/2022 | Luthra et al. |
| 2022/0020481 A1 | 1/2022 | Luthra et al. |
| 2022/0165423 A1 | 5/2022 | Luber et al. |

FOREIGN PATENT DOCUMENTS

| | | |
|---|---|---|
| AU | 2013100344 | 5/2013 |
| AU | 2014100086 | 2/2014 |
| AU | 2015218578 | 8/2016 |
| AU | 2016206364 | 2/2017 |
| AU | 2019200625 | 2/2019 |
| AU | 2019204791 | 7/2019 |
| AU | 2020201726 | 3/2020 |
| AU | 2020100481 | 5/2020 |
| AU | 2020101208 | 8/2020 |
| AU | 2020101336 | 8/2020 |
| AU | 2020101728 | 9/2020 |
| AU | 2020102044 | 10/2020 |
| AU | 2020103842 | 2/2021 |
| BR | 1007141 | 2/2018 |
| BR | 0818877 | 6/2019 |
| BR | 112020008334 | 10/2020 |
| CA | 2342977 | 10/2002 |
| CA | 2468483 | 11/2005 |
| CA | 2716575 | 8/2008 |
| CA | 2745107 | 7/2009 |
| CA | 2757599 | 10/2010 |
| CA | 2698078 | 9/2011 |
| CA | 2840871 | 1/2013 |
| CA | 2977384 | 2/2019 |
| CH | 711954 | 6/2017 |
| CN | 1700879 | 11/2005 |
| CN | 100361133 | 1/2008 |
| CN | 101129257 | 2/2008 |
| CN | 102539735 | 7/2012 |
| CN | 102762152 | 10/2012 |
| CN | 102157023 | 12/2012 |
| CN | 203153725 | 8/2013 |
| CN | 104198482 | 12/2014 |
| CN | 103091486 | 2/2015 |
| CN | 104718557 | 6/2015 |
| CN | 204428014 | 7/2015 |
| CN | 104838264 | 8/2015 |
| CN | 103248681 | 4/2016 |
| CN | 105675854 | 6/2016 |
| CN | 105740322 | 7/2016 |
| CN | 205404383 | 7/2016 |
| CN | 106198538 | 12/2016 |
| CN | 106250668 | 12/2016 |
| CN | 106339857 | 1/2017 |
| CN | 106771286 | 5/2017 |
| CN | 106872341 | 6/2017 |
| CN | 106872538 | 6/2017 |
| CN | 106909796 | 6/2017 |
| CN | 103997951 | 7/2017 |
| CN | 107022650 | 8/2017 |
| CN | 107211097 | 9/2017 |
| CN | 107239655 | 10/2017 |
| CN | 107255712 | 10/2017 |
| CN | 107330524 | 11/2017 |
| CN | 206772947 | 12/2017 |
| CN | 107610745 | 1/2018 |
| CN | 107655889 | 2/2018 |
| CN | 104756093 | 3/2018 |
| CN | 108053134 | 5/2018 |
| CN | 207408411 | 5/2018 |
| CN | 104732468 | 6/2018 |
| CN | 207457253 | 6/2018 |
| CN | 107121542 | 8/2018 |
| CN | 108461158 | 8/2018 |
| CN | 108562741 | 9/2018 |
| CN | 108614100 | 10/2018 |
| CN | 108615214 | 10/2018 |
| CN | 109147916 | 1/2019 |
| CN | 105572110 | 3/2019 |

(56) References Cited

FOREIGN PATENT DOCUMENTS

| | | |
|---|---|---|
| CN | 109587337 | 4/2019 |
| CN | 109658303 | 4/2019 |
| CN | 106645116 | 6/2019 |
| CN | 109900893 | 6/2019 |
| CN | 110021415 | 7/2019 |
| CN | 110038652 | 7/2019 |
| CN | 110045106 | 7/2019 |
| CN | 105898217 | 8/2019 |
| CN | 110189823 | 8/2019 |
| CN | 110349641 | 10/2019 |
| CN | 106659484 | 11/2019 |
| CN | 110444296 | 11/2019 |
| CN | 209678887 | 11/2019 |
| CN | 110546638 | 12/2019 |
| CN | 110570918 | 12/2019 |
| CN | 110580953 | 12/2019 |
| CN | 110796422 | 2/2020 |
| CN | 110827997 | 2/2020 |
| CN | 210071666 | 2/2020 |
| CN | 210199118 | 3/2020 |
| CN | 110957032 | 4/2020 |
| CN | 111027525 | 4/2020 |
| CN | 111161812 | 5/2020 |
| CN | 111210886 | 5/2020 |
| CN | 111220801 | 6/2020 |
| CN | 111243150 | 6/2020 |
| CN | 111247422 | 6/2020 |
| CN | 111261302 | 6/2020 |
| CN | 111276257 | 6/2020 |
| CN | 111311018 | 6/2020 |
| CN | 111312406 | 6/2020 |
| CN | 111340442 | 6/2020 |
| CN | 111354119 | 6/2020 |
| CN | 111354443 | 6/2020 |
| CN | 111354473 | 6/2020 |
| CN | 111369721 | 7/2020 |
| CN | 111370135 | 7/2020 |
| CN | 111370136 | 7/2020 |
| CN | 111403045 | 7/2020 |
| CN | 111430023 | 7/2020 |
| CN | 111444444 | 7/2020 |
| CN | 111461272 | 7/2020 |
| CN | 111462460 | 7/2020 |
| CN | 111465882 | 7/2020 |
| CN | 211015833 | 7/2020 |
| CN | 111484929 | 8/2020 |
| CN | 111513691 | 8/2020 |
| CN | 111540427 | 8/2020 |
| CN | 111540476 | 8/2020 |
| CN | 111540477 | 8/2020 |
| CN | 111550880 | 8/2020 |
| CN | 111552000 | 8/2020 |
| CN | 111554404 | 8/2020 |
| CN | 111564209 | 8/2020 |
| CN | 111582097 | 8/2020 |
| CN | 111582660 | 8/2020 |
| CN | 111598134 | 8/2020 |
| CN | 111601541 | 8/2020 |
| CN | 106874632 | 9/2020 |
| CN | 111370139 | 9/2020 |
| CN | 111403006 | 9/2020 |
| CN | 111627562 | 9/2020 |
| CN | 111627565 | 9/2020 |
| CN | 111629334 | 9/2020 |
| CN | 111630604 | 9/2020 |
| CN | 111639272 | 9/2020 |
| CN | 111640228 | 9/2020 |
| CN | 111640513 | 9/2020 |
| CN | 111643121 | 9/2020 |
| CN | 111651216 | 9/2020 |
| CN | 111652104 | 9/2020 |
| CN | 111654825 | 9/2020 |
| CN | 111667390 | 9/2020 |
| CN | 111667902 | 9/2020 |
| CN | 111681727 | 9/2020 |
| CN | 111693694 | 9/2020 |
| CN | 111710401 | 9/2020 |
| CN | 211454690 | 9/2020 |
| CN | 211454692 | 9/2020 |
| CN | 106999041 | 10/2020 |
| CN | 111755124 | 10/2020 |
| CN | 111785393 | 10/2020 |
| CN | 111798607 | 10/2020 |
| CN | 111798951 | 10/2020 |
| CN | 111798970 | 10/2020 |
| CN | 111798982 | 10/2020 |
| CN | 111816294 | 10/2020 |
| CN | 111835762 | 10/2020 |
| CN | 111863168 | 10/2020 |
| CN | 111863223 | 10/2020 |
| CN | 111863224 | 10/2020 |
| CN | 111867672 | 10/2020 |
| CN | 211674200 | 10/2020 |
| CN | 211776141 | 10/2020 |
| CN | 211787238 | 10/2020 |
| CN | 211787265 | 10/2020 |
| CN | 107133901 | 11/2020 |
| CN | 111879769 | 11/2020 |
| CN | 111882164 | 11/2020 |
| CN | 111918797 | 11/2020 |
| CN | 111935203 | 11/2020 |
| CN | 111968730 | 11/2020 |
| CN | 211858162 | 11/2020 |
| CN | 211883765 | 11/2020 |
| CN | 211906967 | 11/2020 |
| CN | 112017342 | 12/2020 |
| CN | 112102945 | 12/2020 |
| CN | 112119469 | 12/2020 |
| CN | 212061244 | 12/2020 |
| CN | 112368782 | 2/2021 |
| DE | 10248682 | 5/2004 |
| DE | 69731901 | 12/2005 |
| DE | 102005010094 | 9/2006 |
| DE | 102007010757 | 4/2010 |
| DE | 102012102918 | 10/2013 |
| DE | 202015100937 | 6/2015 |
| DE | 102014105937 | 10/2015 |
| DE | 202015006405 | 2/2016 |
| DE | 202016105331 | 11/2016 |
| DE | 202015009440 | 8/2017 |
| DE | 102016202428 | 6/2018 |
| DE | 202020002331 | 7/2020 |
| DE | 202020104079 | 7/2020 |
| DE | 202020004020 | 10/2020 |
| EP | 359623 | 3/1990 |
| EP | 761160 | 3/1997 |
| EP | 1027459 | 8/2000 |
| EP | 1327215 | 7/2003 |
| EP | 1575010 | 9/2005 |
| EP | 1688086 | 8/2006 |
| EP | 1883345 | 2/2008 |
| EP | 1583585 | 6/2008 |
| EP | 1952162 | 8/2008 |
| EP | 2094153 | 9/2009 |
| EP | 2416702 | 2/2012 |
| EP | 2415243 | 1/2015 |
| EP | 2912626 | 9/2015 |
| EP | 3061062 | 8/2016 |
| EP | 2753917 | 3/2017 |
| EP | 3207472 | 8/2017 |
| EP | 3218715 | 9/2017 |
| EP | 3317865 | 5/2018 |
| EP | 3454341 | 3/2019 |
| EP | 3397744 | 8/2019 |
| EP | 2946198 | 10/2019 |
| EP | 3552018 | 10/2019 |
| EP | 3026874 | 11/2019 |
| EP | 3607321 | 2/2020 |
| EP | 3420713 | 5/2020 |
| EP | 3647900 | 5/2020 |
| EP | 3662259 | 6/2020 |
| EP | 3311163 | 8/2020 |
| EP | 3691788 | 8/2020 |
| EP | 3559849 | 9/2020 |

(56) References Cited

FOREIGN PATENT DOCUMENTS

| | | |
|---|---|---|
| EP | 3701543 | 9/2020 |
| EP | 3702988 | 9/2020 |
| EP | 3711062 | 9/2020 |
| EP | 3714459 | 9/2020 |
| EP | 3729335 | 10/2020 |
| EP | 3257026 | 11/2020 |
| EP | 3737947 | 11/2020 |
| ES | 2327385 | 10/2009 |
| FI | 201305093 | 8/2014 |
| FR | 3087918 | 5/2020 |
| GB | 2347503 | 9/2000 |
| GB | 2533066 | 9/2017 |
| GB | 2553512 | 3/2018 |
| HK | 1200186 | 7/2015 |
| HK | 1206426 | 1/2016 |
| IN | 290952 | 4/2010 |
| IN | 201001258 | 6/2010 |
| IN | 201200846 | 8/2015 |
| IN | 201811043670 | 12/2018 |
| IN | 201711027532 | 3/2019 |
| IN | 201917036547 | 11/2019 |
| IN | 202011012796 | 3/2020 |
| IN | 202041015755 | 5/2020 |
| IN | 202041024780 | 6/2020 |
| IN | 202021024064 | 7/2020 |
| IN | 202041028143 | 7/2020 |
| IN | 201811030959 | 8/2020 |
| IN | 201917027562 | 9/2020 |
| IN | 202017033677 | 9/2020 |
| IN | 202038032228 | 9/2020 |
| IN | 202041040216 | 9/2020 |
| IN | 202011041126 | 10/2020 |
| IN | 202021044172 | 10/2020 |
| IN | 202041043957 | 10/2020 |
| IN | 202041044040 | 10/2020 |
| JP | 2002511965 | 4/2002 |
| JP | 2007200107 | 8/2007 |
| JP | 4076386 | 4/2008 |
| JP | 2009031887 | 2/2009 |
| JP | 2010190867 | 9/2010 |
| JP | 2011065540 | 3/2011 |
| JP | 2012002435 | 1/2012 |
| JP | 5928332 | 6/2016 |
| JP | 5946030 | 7/2016 |
| JP | 2017042601 | 3/2017 |
| JP | 2017204214 | 11/2017 |
| JP | 2018000278 | 1/2018 |
| JP | 6275876 | 2/2018 |
| JP | 6329627 | 5/2018 |
| JP | 6356141 | 7/2018 |
| JP | 2019188162 | 10/2019 |
| JP | 2019528092 | 10/2019 |
| JP | 2019209203 | 12/2019 |
| JP | 6669658 | 3/2020 |
| JP | 2020042685 | 3/2020 |
| JP | 2020067939 | 4/2020 |
| JP | 2020080083 | 5/2020 |
| JP | 2020514775 | 5/2020 |
| JP | 2020516999 | 6/2020 |
| JP | 2020101571 | 7/2020 |
| JP | 2020102249 | 7/2020 |
| JP | 2020520690 | 7/2020 |
| JP | 2020128995 | 8/2020 |
| JP | 2020128999 | 8/2020 |
| JP | 2020524806 | 8/2020 |
| JP | 6765777 | 10/2020 |
| JP | 2020169999 | 10/2020 |
| JP | 6786906 | 11/2020 |
| JP | 2019130494 | 11/2020 |
| JP | 2019561485 | 11/2020 |
| JP | 2020184290 | 11/2020 |
| JP | 2020184379 | 11/2020 |
| KR | 100514036 | 9/2005 |
| KR | 100700219 | 3/2007 |
| KR | 100955002 | 4/2010 |
| KR | 20120016877 | 2/2012 |
| KR | 20130047776 | 5/2013 |
| KR | 20150138244 | 12/2015 |
| KR | 2016096455 | 8/2016 |
| KR | 101773416 | 9/2017 |
| KR | 1789208 | 10/2017 |
| KR | 1798818 | 11/2017 |
| KR | 1837081 | 3/2018 |
| KR | 2018132914 | 12/2018 |
| KR | 2034352 | 10/2019 |
| KR | 20190134314 | 12/2019 |
| KR | 20200041458 | 4/2020 |
| KR | 2020047457 | 5/2020 |
| KR | 20200054203 | 5/2020 |
| KR | 20200082445 | 7/2020 |
| KR | 2152030 | 8/2020 |
| KR | 2020095041 | 8/2020 |
| KR | 2159722 | 9/2020 |
| KR | 2020111292 | 9/2020 |
| KR | 20200105711 | 9/2020 |
| KR | 20200121808 | 10/2020 |
| KR | 102190872 | 12/2020 |
| KR | 102190873 | 12/2020 |
| KR | 1022161480000 | 2/2021 |
| MX | 362826 | 2/2019 |
| MY | 171637 | 10/2019 |
| RU | 2564832 | 2/2014 |
| RU | 2015115133 | 11/2016 |
| RU | 2639731 | 12/2017 |
| SG | 10201914077 | 3/2020 |
| TW | I377046 | 12/1999 |
| TW | 537880 | 6/2003 |
| TW | 200835465 | 9/2008 |
| TW | 201400813 | 1/2014 |
| TW | M523925 | 6/2016 |
| TW | 560437 | 12/2016 |
| TW | 698221 | 7/2020 |
| WO | 00033259 | 6/2000 |
| WO | 01027857 | 4/2001 |
| WO | 0165443 | 9/2001 |
| WO | 01097050 | 12/2001 |
| WO | 2004001640 | 12/2003 |
| WO | 2004042596 | 5/2004 |
| WO | 2004114180 | 12/2004 |
| WO | 2005034008 | 4/2005 |
| WO | 2008119182 | 10/2008 |
| WO | 2009012585 | 1/2009 |
| WO | 2011049886 A1 | 4/2011 |
| WO | 2012154488 | 11/2012 |
| WO | 2013006615 | 1/2013 |
| WO | 2013026999 | 2/2013 |
| WO | 2013120199 | 8/2013 |
| WO | 2013155002 | 10/2013 |
| WO | 2014178062 | 11/2014 |
| WO | 2014196535 | 12/2014 |
| WO | 2015073878 | 5/2015 |
| WO | 2015143309 | 9/2015 |
| WO | 2016057786 | 4/2016 |
| WO | 2016201595 | 12/2016 |
| WO | 2017079849 | 5/2017 |
| WO | 2018035147 | 2/2018 |
| WO | 2018044894 | 3/2018 |
| WO | 2018082257 | 5/2018 |
| WO | 2018163207 | 9/2018 |
| WO | 2018208820 | 11/2018 |
| WO | 2018227256 | 12/2018 |
| WO | 2019130494 | 7/2019 |
| WO | 2019140334 | 7/2019 |
| WO | 2019144112 | 7/2019 |
| WO | 2019175660 | 9/2019 |
| WO | 2019200148 | 10/2019 |
| WO | 2019215199 | 11/2019 |
| WO | 2019222081 | 11/2019 |
| WO | 2020000598 | 1/2020 |
| WO | 2020008192 | 1/2020 |
| WO | 2020009900 | 1/2020 |
| WO | 2020012476 | 1/2020 |
| WO | 2020016616 | 1/2020 |
| WO | 2020028837 | 2/2020 |

(56) References Cited

FOREIGN PATENT DOCUMENTS

| WO | 2020038461 | | 2/2020 |
|---|---|---|---|
| WO | 2020041528 | | 2/2020 |
| WO | 2020051365 | | 3/2020 |
| WO | 2020091155 | | 5/2020 |
| WO | 2020102223 | | 5/2020 |
| WO | 2020118152 | | 6/2020 |
| WO | 2020128146 | | 6/2020 |
| WO | 2020141346 | | 7/2020 |
| WO | 2020150403 | | 7/2020 |
| WO | 2020171448 | | 8/2020 |
| WO | 2020186231 | | 9/2020 |
| WO | 2020198511 | | 10/2020 |
| WO | 2020263745 | | 12/2020 |
| WO | 2021252571 | A1 | 12/2021 |
| WO | 2022112843 | A1 | 6/2022 |

OTHER PUBLICATIONS

United States Patent and Trademark Office, "Notice of Allowance and Fee(s) Due," issued in connection with U.S. Appl. No. 17/240,644, dated Jul. 28, 2022, 8 pages.

United States Patent and Trademark Office, "Non-Final Office Action," issued in connection with U.S. Appl. No. 17/240,644, dated Jun. 20, 2022, 6 pages.

"Abbott's New NAVICA App: What You Need to Know" Abbott, dated Aug. 26, 2020, 2 pages, <https://www.abbott.com/corpnewsroom/diagnostics-testing/abbotts-new-NAVICA-app-what-you-need-to-know.html>.

Virki, "Estonia starts testing digital immunity passport for workplaces" Reuters, dated May 23, 2020, 2 pages. < https://www.reuters.com/article/health-coronavirus-estonia-digital/estonia-starts-testing-digital-immunity-passport-for-workplaces-idUSKBN22WOGE>.

United States Patent and Trademark Office, "Notice of Allowance," issued in connection with U.S. Appl. No. 17/068,608, dated Dec. 4, 2020, 10 pages.

United States Patent and Trademark Office, "Non-Final Office Action," issued in connection with U.S. Appl. No. 17/068,601, dated Dec. 30, 2020, 13 pages.

Nadeem Ahmed et al., "A Survey of Covid-19 Contact Tracing Apps," in IEEE Access, vol. 8, pp. 134577-134601, published Jul. 20, 2020, 25 pages.

Qing Ye et al., "Using Information Technology to Manage the COVID-19 Pandemic: Development of a Technical Framework Based on Practical Experience in China," National Library of Medicine, JMIR Medical Informatics, Jun. 8, 2020, 2 pages.

Weimin Xin et al., "Fighting COVID-19 and helping economy reopen by using blockchain technology," IEEE/CIC International Conference on Communications in China (ICCC Workshops), Chongqing, China, pp. 102-105, 2020, 4 pages.

United States Patent and Trademark Office, "Notice of Allowance," issued in connection with U.S. Appl. No. 17/068,599, dated Dec. 16, 2020, 9 pages.

International Searching Authority, "Search Report and Written Opinion," issued in connection with Application No. PCT/US2021/023488, dated May 17, 2021, 15 pages.

Hicks et al., "SecureABC: Secure AntiBody Certificates for COVID-19," arXiv: 2005.1183 3, last revised Oct. 12, 2020, 11 pages.

Icaomid, "Travel Pass," IATA, Third Middle East Directions General of Civil Aviation DGGA-MID/3 Virtual Meeting, Dec. 7, 2020, 19 pages.

United States Patent and Trademark Office, "Final Office Action," issued in connection with U.S. Appl. No. 17/068,601, dated May 13, 2021, 19 pages.

Marc Eisenstadt et al., "COVID-19 Antibody Test/Vaccination Certification: There's an App for That," in IEEE Open Journal of Engineering in Medicine and Biology, vol. 1, pp. 148-155, published online on Jun. 1, 2020, 13 pages.

Jessica X. H. Wong et al. "Direct Reading of Bona Fide Barcode Assays for Diagnostics with Smartphone Apps." Scientific reports vol. 5:11727, published Jun. 30, 2015, 11 pages.

Giovanni Rateni et al. "Smartphone-Based Food Diagnostic Technologies: A Review." Sensors (Basel, Switzerland) vol. 17, 1453, published Jun. 20, 2017, 22 pages.

United States Patent and Trademark Office, "Non-Final Office Action," issued in connection with U.S. Appl. No. 17/208,754, dated Dec. 27, 2021, 8 pages.

* cited by examiner

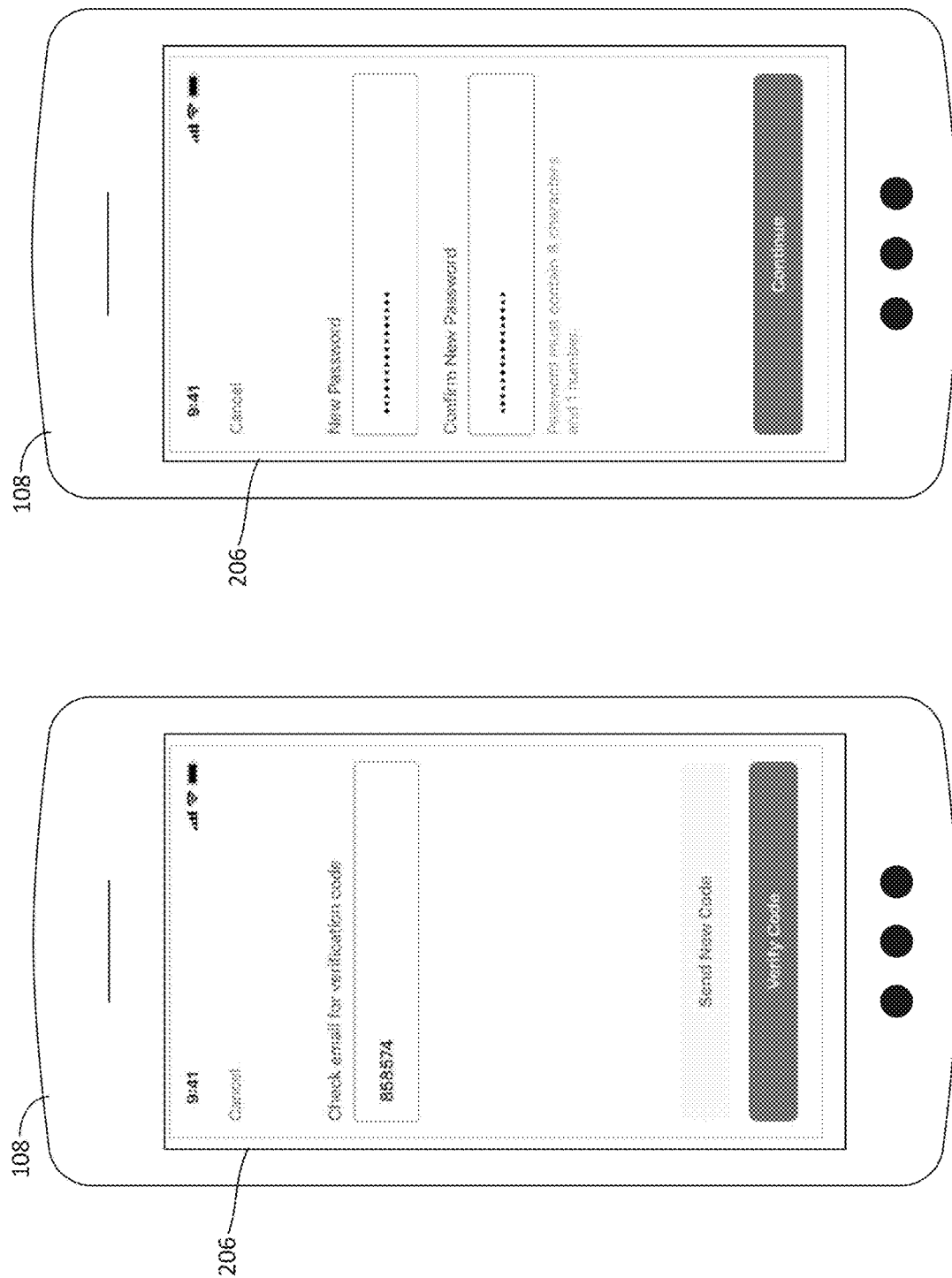

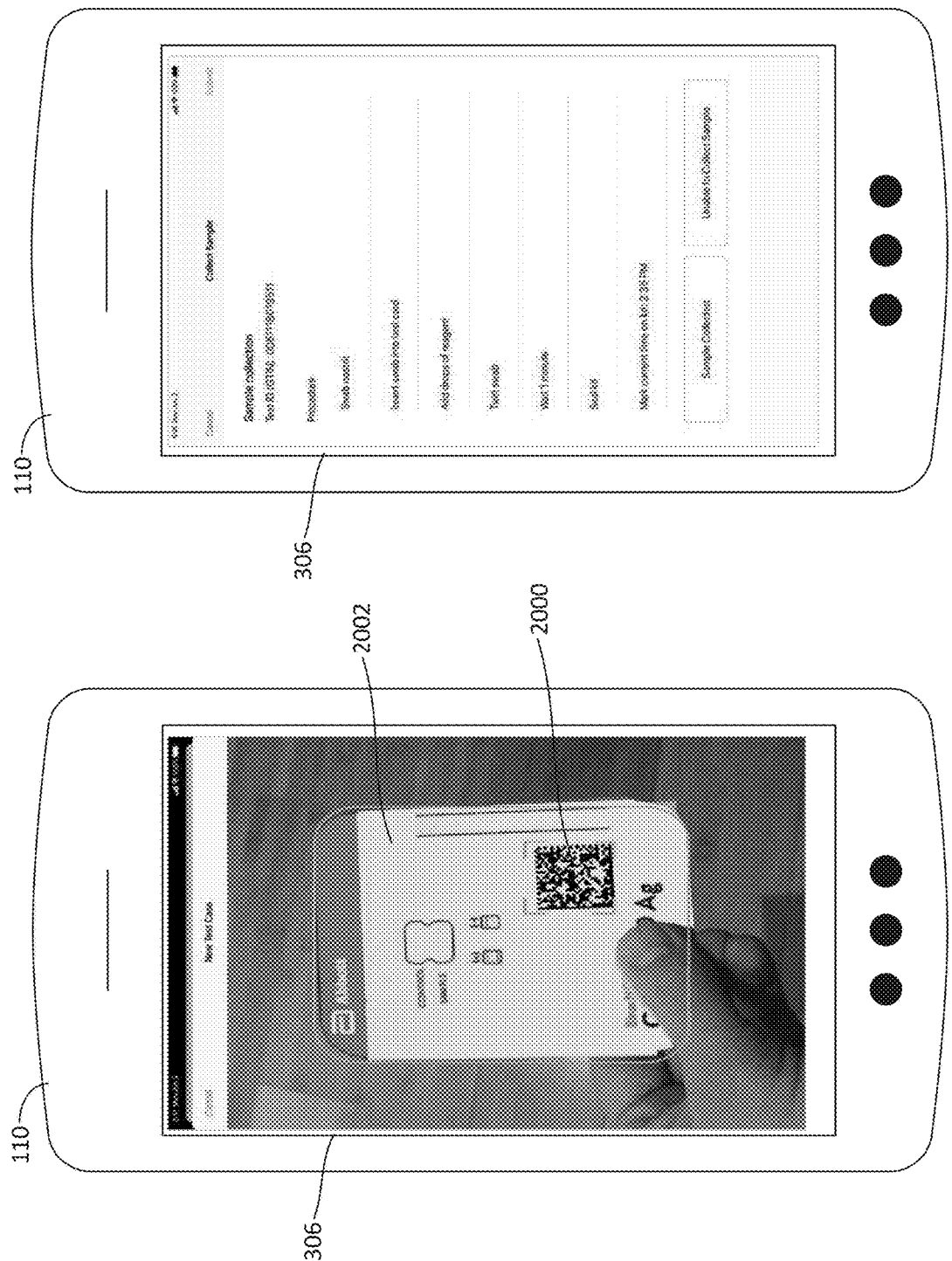

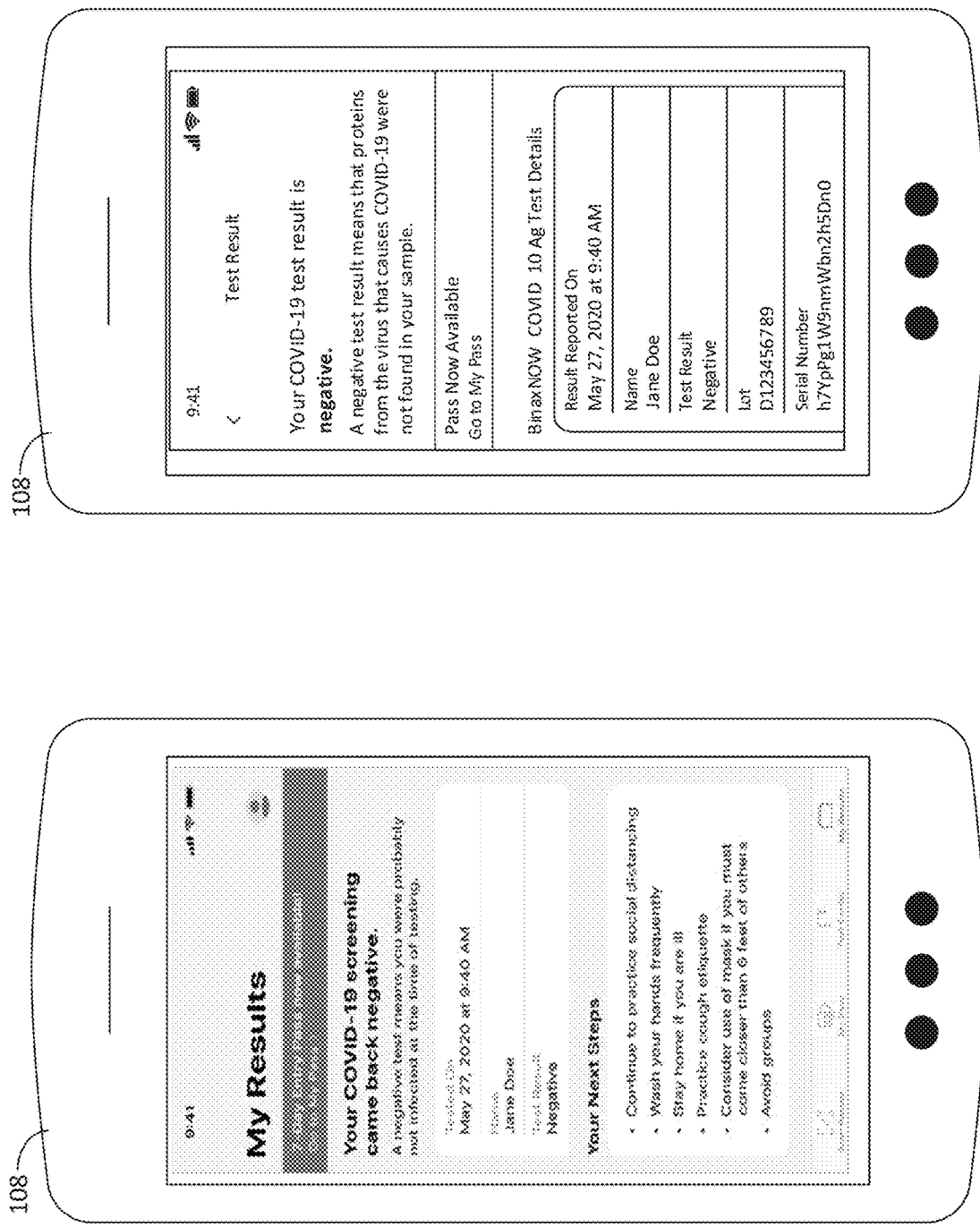

DIGITAL PASS VERIFICATION SYSTEMS AND METHODS

RELATED PATENT APPLICATIONS

This patent arises from a continuation of U.S. application Ser. No. 17/240,644, titled "DIGITAL PASS VERIFICATION SYSTEMS AND METHODS," filed Apr. 26, 2021, which is a continuation of U.S. application Ser. No. 17/068,599 (U.S. Pat. No. 10,991,185), titled "DIGITAL PASS VERIFICATION SYSTEMS AND METHODS," filed Oct. 12, 2020. U.S. application Ser. No. 17/068,599 claims the benefit under 35 U.S.C. § 119(e) to U.S. Provisional Application No. 63/054,170, titled "ELECTRONIC HEALTH PASS VERIFICATION SYSTEMS AND METHODS," filed Jul. 20, 2020, and to U.S. Provisional Application No. 63/080,391, titled "ELECTRONIC HEALTH PASS VERIFICATION SYSTEMS AND METHODS," filed Sep. 18, 2020. Thus, priority to U.S. application Ser. No. 17/240,644; U.S. application Ser. No. 17/068,599; U.S. Provisional Application No. 63/054,170; and U.S. Provisional Application No. 63/080,391 is claimed. U.S. application Ser. No. 17/240,644; U.S. application Ser. No. 17/068,599; U.S. Provisional Application No. 63/054,170; and U.S. Provisional Application No. 63/080,391 are incorporated herein by this reference in their entireties.

FIELD OF THE DISCLOSURE

This disclosure relates generally to health-based screening and, more particularly, to digital pass verification systems and methods.

BACKGROUND

In recent years, there has been a rise in outbreaks of infectious diseases (e.g., viral diseases, bacterial diseases, etc.) such as the COVID-19 virus, Ebola virus, H1N1pdm09 virus, Middle East respiratory syndrome coronavirus (MERS-CoV), and Severe Acute Respiratory Syndrome (SARS), to name a few. These infectious diseases are often contagious and easily transmitted from person-to-person in close proximity or through indirect contact via objects and surfaces. To curb the spread of infectious diseases, many entities (e.g., companies, schools, retailers, governments, facility managers, etc.) restrict people with symptoms of infectious diseases from accessing their locations or facilities.

BRIEF DESCRIPTION OF THE DRAWINGS

FIG. 1 shows an example user, an example tester, an example verifier, and an example digital pass management system.

FIGS. 6-13 are example user interface screens that may be displayed on the example user device of FIG. 2 by the example user application.

FIGS. 14-25 are example user interface screens that may be displayed on the example tester device of FIG. 3 by the example tester application.

FIGS. 26, 27A, 27B, 28A, and 28B are example user interface screens that may be displayed on the example user device of FIG. 2 by the example user application.

The figures are not to scale. In general, the same reference numbers will be used throughout the drawing(s) and accompanying written description to refer to the same or like parts.

Figure 1:
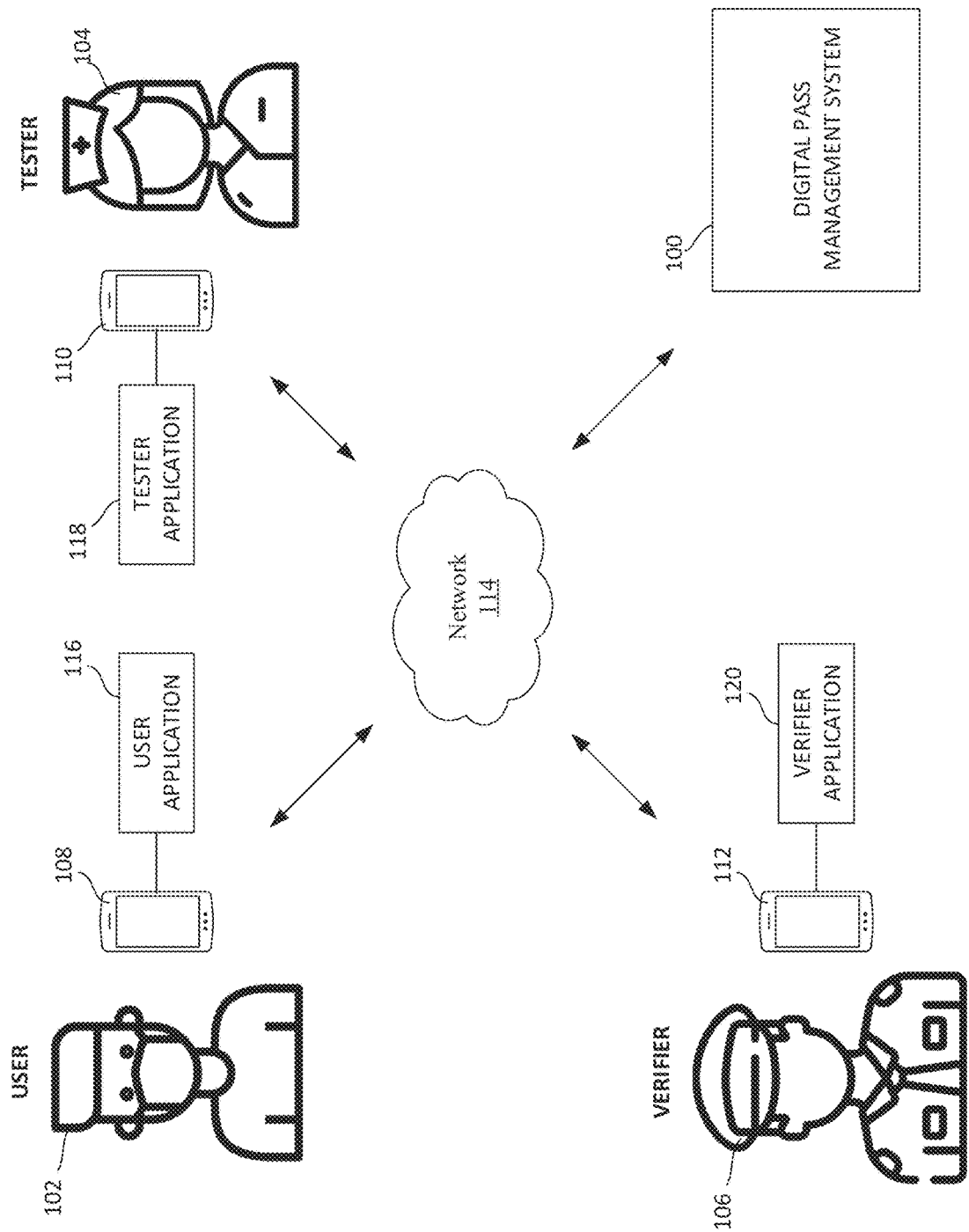
FIG. 1 illustrates an example system or network of entities or persons with which the examples disclosed herein can be employed.

Unless specifically stated otherwise, descriptors such as "first," "second," "third," etc. are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name.

DETAILED DESCRIPTION

Disclosed herein are example apparatus, systems, methods, and articles of manufacture that enable entities or persons, referred to herein as verifiers, to verify whether a person has recently tested negative for an infectious disease (e.g., a pathogen, a virus, a bacteria, etc.) before granting the person access to a particular location or area. This enables a verifier to maintain a safe environment for the people in the particular area and reduce the likelihood of infection. Example verifiers may include airlines, offices, malls, libraries, sporting arenas, schools, theatres, retailers, utilities, employers, governments, facility managers, and/or any other entity or person that desires to control access to a particular location. Many examples disclosed herein are described in connection with testing for pathogens, viruses, and other infectious diseases. However, it is understood that any examples disclosed herein can be implemented in connection with testing for any analyte of interest.

In examples disclosed herein, a person, referred to herein as a user, may be tested for a particular infectious disease. If the results are negative, a digital pass (which may also be referred to as an electronic pass, a digital health pass, an electronic health pass, a health pass, a digital health card, an electronic health card, or a health card) is generated that can be stored on the user's electronic device, such as, for example, his/her smartphone, smartwatch, etc. In some examples, the digital pass includes a code such as, for example, a Data Matrix Code, a Quick Response (QR) code, a bar code, and/or other machine-readable code. In some examples, the digital pass code includes a user identification (e.g., a user account ID) and a test kit identification associated with a test kit used to test the user. In other examples, the digital pass code can include other information. When the user arrives at a verifier location, a verifier can scan the digital pass code of the digital pass on the user's electronic device to confirm the user has been tested and the test was negative (i.e., the user is not infected with the pathogen subject to the test). In some examples, the verifier uses a verifier device, such as a smartphone, a handheld scanner, or a mounted scanner communicatively coupled to a computer to scan the digital pass code. In some examples, the scanner is a camera. In some examples, a record of the user's test result is stored in a digital pass management system. The verifier can check the identity of the user and their test result with the digital pass management system. The digital pass code enables the verifier to quickly and accurately obtain identifying information about the user that can be used to confirm whether the user has recently been tested and whether the test result was negative for the infectious disease. If the digital pass is valid, the verifier can allow the user to access the location. However, if the user does not have a digital pass, or the digital pass is invalid or expired, the verifier can deny the user access to the location, thereby reducing the risk of infection to others in the location.

In some examples, the user is tested by a tester (e.g., medical professional such as a nurse, a doctor, etc.) at a testing facility (e.g., a doctor's office, hospital, medical clinic, etc.). In some examples, the user's electronic device generates a unique identity code to identify the user. The tester can scan the identity code (e.g., with a tester electronic device such as a tablet or smartphone) to create a record of the user and the test with the digital pass management system. The results of the test are stored with the user's record in the digital pass management system.

In some examples, each user device, tester device, and verifier device operates an application that enables the persons and devices to interface with the digital pass management system. The digital pass management system stores account information, test results, and other information. The digital pass management system provides an interface between the various entities.

In some examples, the verifier is a workplace that desires to keep their employees safe. The verifier may require that the employees have a valid digital pass every day the employees enter the workplace. In some examples, the digital pass expires after a certain period of time after being tested (e.g., 5 days, 7 days, 10 days, etc.). Therefore, the employees may need to be tested multiple times and/or on a regular basis.

The examples disclosed herein benefit all parties, including the employees, the employers (the verifiers), and the testers. From an employee standpoint, for example, the examples disclosed herein enable the employee to safely return to work, which could be a more effective and productive environment than working remotely or could be the employee's only option to work if they cannot perform their duties remotely. This also encourages employees to be better citizens by maintaining awareness of their health and risk to others. From an employer standpoint, for example, the examples disclosed herein can be used to reinforce the importance of employee safety at the workplace, have confidence in the safety of the workplace, manage risk to employees at the workplace, understand who has access to a site, verify employee's pass ad-hoc, act locally based on high frequency data, and access data that may inform access policies to the workplace. From a tester standpoint, for example, the examples disclosed herein enable testers to administer tests and record results efficiently, manage throughput of employees in a reasonable fashion, and maintain the safety of employees awaiting testing and results. These and other benefits are similarly achieved in connection with other types of verifier organizations, such as schools, malls, airlines, sports arenas, etc.

FIG. 1 illustrates an example digital pass management system 100 constructed in accordance with the teachings of this disclosure. The digital pass management system 100 interfaces with multiple persons or entities and/or distributes software to such persons or entities to facilitate the example digital pass verification processes disclosed herein. For example, the example digital pass management system 100 can be used to facilitate the generation of an digital pass for a user (e.g., a person) and enable a verifier to grant or deny access to the user based on the digital pass. FIG. 1 shows an example user 102, an example tester 104, and an example verifier 106. In this example, the user 102 has a first electronic device 108 referred to herein as a user device 108, the tester 104 has a second electronic device 110 referred to herein as a tester device 110, and the verifier 106 has a third electronic device 112 referred to herein as a verifier device 112. While only one user, tester, and verifier are illustrated, it is understood that the example digital pass management system 100 can support multiple (e.g., hundreds, thousands, millions, etc. of users) users, testers, and/or verifiers.

The verifier 106 can represent any person or entity that desires to verify a health status of a person (e.g., the user 102) before granting access to a physical location. The health status includes information related to a person's health such as, for example, a positive or negative result from a diagnostic test for an infectious disease. The verifier 106 may be an airline, an office, a school, a mall, a library, other businesses, a government, a park ranger, other facility managers, etc. For example, the verifier 106 may be an airline gate agent who checks tickets and digital passes of the user 102 prior to boarding a plane. In another example, the verifier 106 may be a security agent or other person who checks the pass of the user 102 prior to the user entering an office building. The verifier 106 uses the verifier device 112 to check the health status of the user 102, as disclosed in further detail herein. In some examples, the verifier device 112 is a mobile electronic device, such as a smartphone, a tablet, a laptop computer, a handheld code scanner, etc. In other examples, the verifier device 112 can be implemented as a non-mobile electronic device, such as a desktop computer, a kiosk, a non-mobile interne connected device capable of scanning a QR code, Data Matrix Code, and/or a barcode, etc.

The user 102 can represent any person that desires to access the location regulated by the verifier 106. The user 102 can interact with the user device 108 to create a digital pass account, receive and view results of a diagnostic test, and/or display a digital pass, as disclosed in further detail herein. The user device 108 is an electronic device that is carried by the user 102. In this example, the user device 108 is a smartphone. However, in other examples, the user device 108 can be implemented by any type of mobile or non-mobile electronic device, such as a tablet, a smartwatch, a laptop computer, a desktop computer, etc.

The tester 104 can represent any person or entity, such as a nurse, a doctor, a testing facility, a hospital, a clinic, etc. that tests a sample from a person/user to be tested for an infectious disease (e.g., a disease caused by a virus, a bacteria, etc.). The tester 104 can interact with the tester device 110 to match the user 102 with a testing kit, enter the test results, etc., as disclosed in further detail herein. In this example, the tester device 110 is a tablet. However, in other examples, the tester device 108 can be implemented by any type of mobile or non-mobile electronic device, such as a smartphone, a laptop computer, a desktop computer, etc.

The digital pass management system 100, the user device 108, the tester device 110, and the verifier device 112 communicate via a network 114, such as, for example, the Internet. In some examples, each of the user device 108, the tester device 110, and the verifier device 112 downloads an application through which the digital pass management system 100, the user device 108, the tester device 110, and the verifier device 112 can communicate. The applications may be specific to the type of entity. For example, as shown in FIG. 1, the user device 108 includes a user application 116, the tester device 110 includes a tester application 118, and the verifier device 112 includes a verification application 120. In some examples the applications are downloaded onto the respective devices from the digital pass management system 100 or another entity, such as, for example, the Apple App Store or the Google Play Store. Thus, the example application disclosed herein can utilize different operating systems. The digital pass management system 100, the user device 108, the tester device 110, and the verifier device 112 may communicate and view information provided in the applications.

While many of the example operations disclosed herein are described in connection with functions performed by the specific applications, these operations are not limited to functions performed by an application downloaded onto a device. Instead, the operations can be performed via a web browser or web-based applications. In some such examples, one or more of the operations can be performed remotely, such as by the digital pass management system 100, and displayed on the respective devices. Also, in some examples, the operations of the applications disclosed herein are cloud based, partially cloud based, or edge based.

Figure 2:
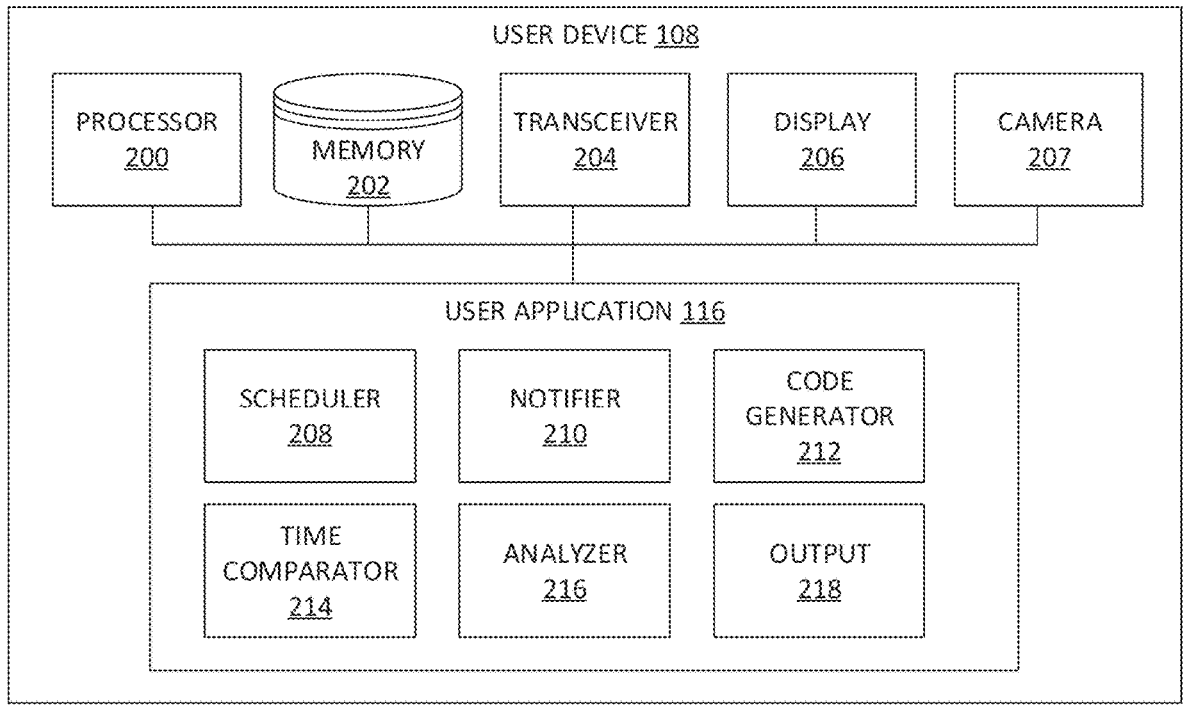
FIG. 2 is a block diagram of an example user device associated with the example user of FIG. 1 and used to execute an example user application.

FIG. 2 is a block diagram of the example user device 108. As disclosed above, in some examples, the user device 108 is implemented as a smartphone. However, in other examples, the user device 108 can be implemented as any other type of mobile or non-mobile electronic device. In this example, the user device 108 includes an example processor 200, an example memory 202, an example transceiver 204, an example display 206 (e.g., a capacitive touchscreen), and an example camera 207. The transceiver 204 can be any type of wired or wireless hardware, firmware, or software for enabling communication with other devices, such as via a wireless internet connection, Bluetooth®, Ethernet connection, etc. The user application 116 can be stored in the memory 202 and executed by the processor 200. The user application 116 includes an example scheduler 208, an example notifier 210, an example code generator 212, an example time comparator 214, an example analyzer 216, and an example output 218. Operation of the user application 116 is disclosed in further detail below.

Figure 3:
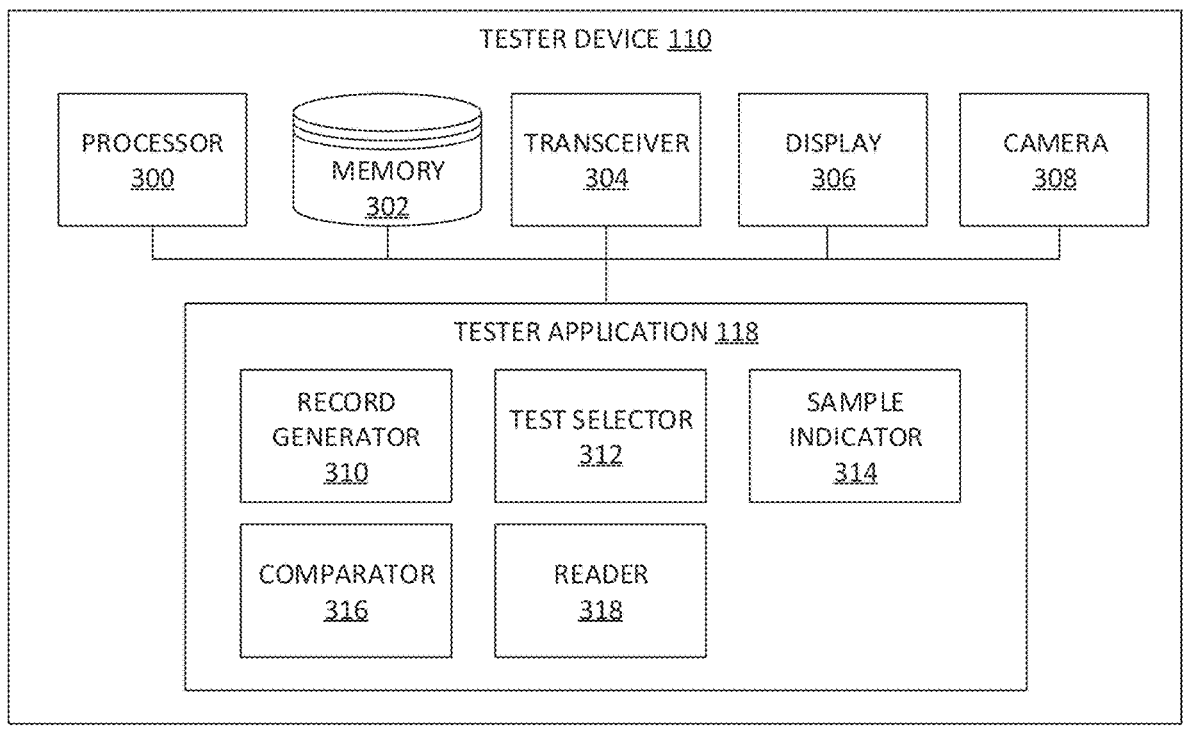
FIG. 3 is a block diagram of an example tester device associated with the example tester of FIG. 1 and used to execute an example tester application.

FIG. 3 is a block diagram of the example tester device 110. In some examples, the tester device 110 is implemented by a mobile electronic device such as a smartphone, a laptop computer, a tablet, etc. In other examples, the tester device 110 can be implemented by a non-mobile electronic device such as a desktop computer, a medical instrument, a server, etc. The tester device 110 includes an example processor 300, an example memory 302, an example transceiver 304, and an example display 306. In this example, the tester device 110 also includes a camera 308. The camera 308 can be used to take pictures and/or scan codes, such as QR codes, as disclosed in further detail herein. The camera 308 can be part of the tester device 110 (e.g., a camera built into a smartphone) or communicatively coupled to the tester device 110 (e.g., a handheld scanner in wireless communication with the tester device 110). The tester application 118 can be stored in the memory 302 and executed by the processor 300. The tester application 118 includes an example record generator 310, an example test selector 312, an example sample indicator 314, an example comparator 316, and an example reader 318. Operation of the tester application 118 is disclosed in further detail below.

Figure 4:
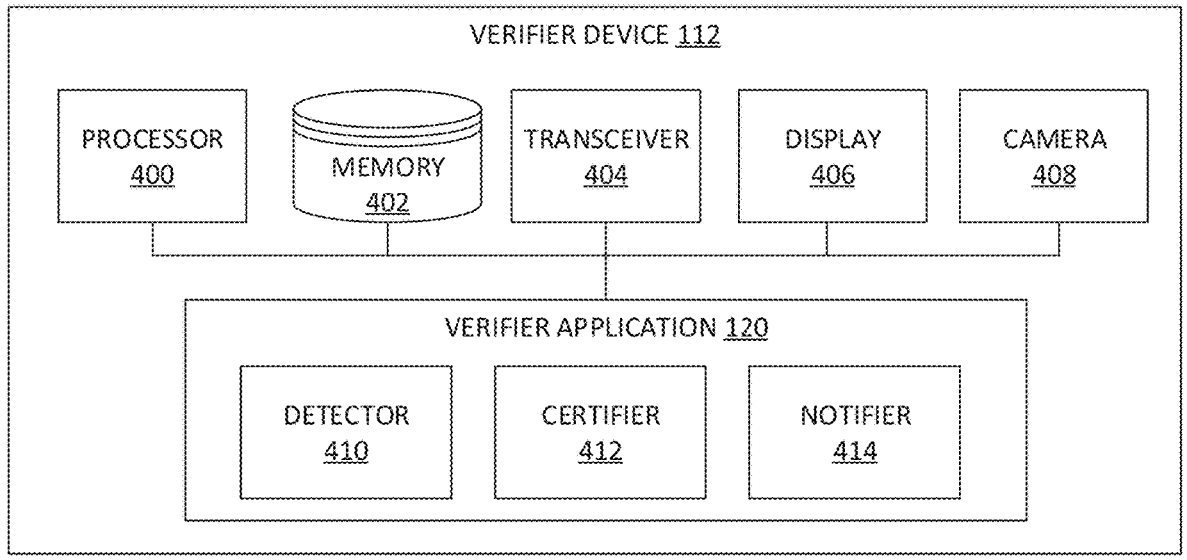
FIG. 4 is a block diagram of an example verifier device associated with the example verifier of FIG. 1 and used to execute an example verifier application.

FIG. 4 is a block diagram of the example verifier device 112. In some examples, the verifier device 112 is implemented by a mobile electronic device, such as a smartphone, a laptop computer, tablet, etc. In other examples, the verifier device 112 can be implemented by a scanner such as, for example, a handheld code scanner. In other examples, the user device 108 can be implemented as any other type of mobile or non-mobile electronic device. The verifier device 112 includes an example processor 400, an example memory 402, an example transceiver 404, an example display 406, and an example camera 408. The camera 408 can be part of the verifier device 112 (e.g., a camera built into a smartphone) or communicatively coupled to the verifier device 112 (e.g., a mounted or a handheld scanner in wireless communication with the verifier device 112). The verifier application 120 can be stored in the memory 402 and executed by the processor 404. The verifier application 120 includes an example detector 410, an example certifier 412, and an example notifier 414. Operation of the verifier application 120 is disclosed in further detail below.

Figure 5:
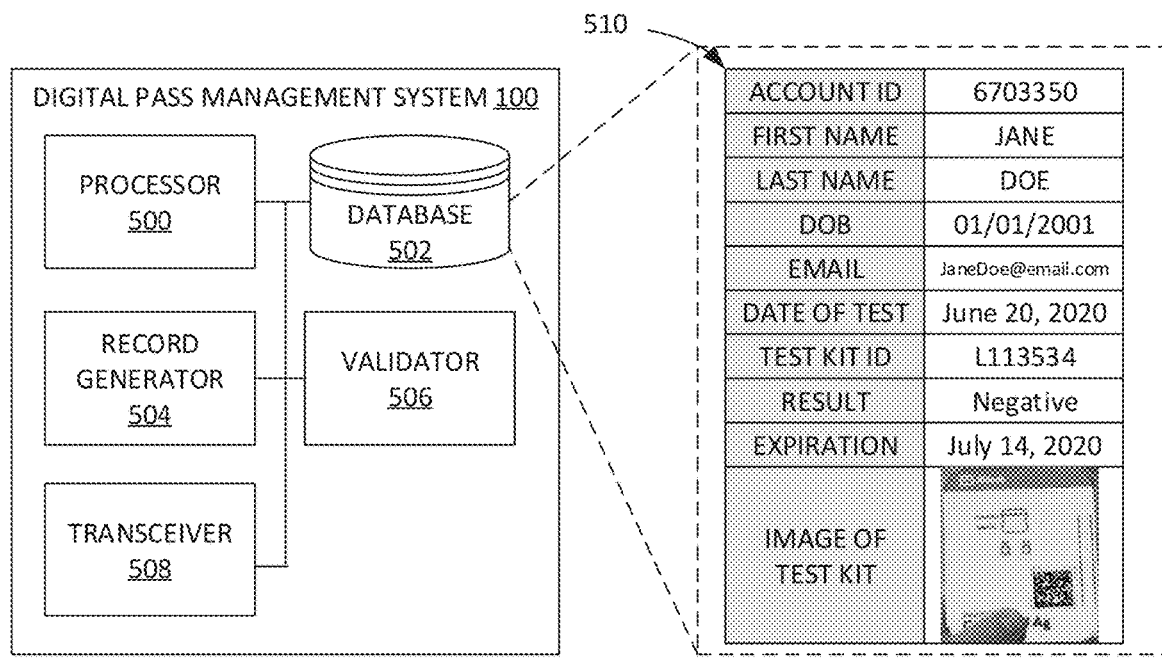
FIG. 5 is a block diagram of the example digital pass management system of FIG. 1.
Figure 7:
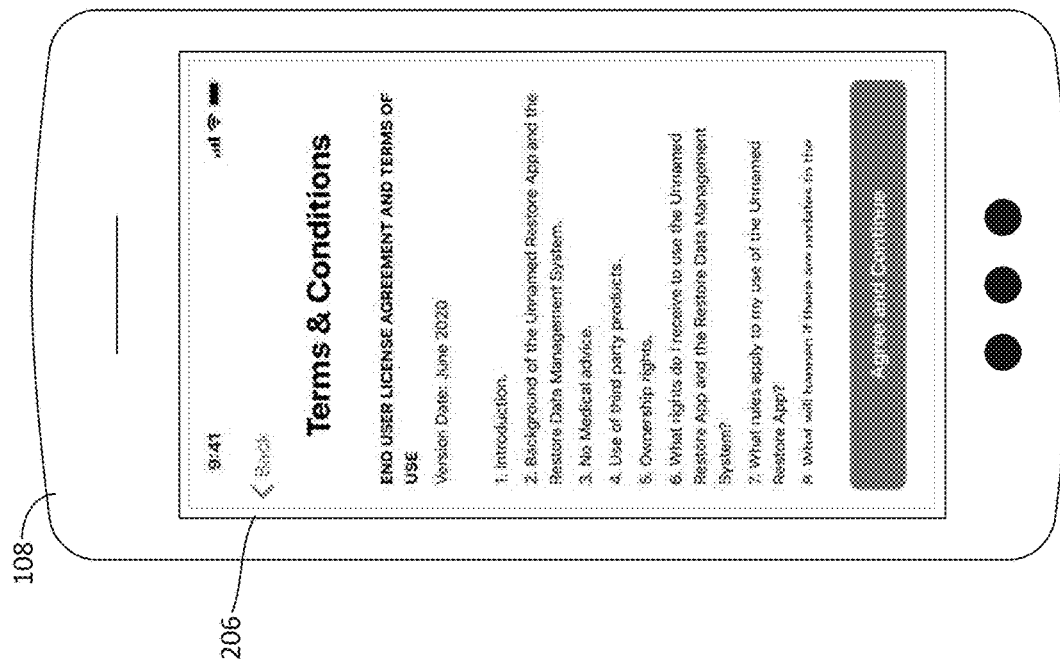
Figure 6:
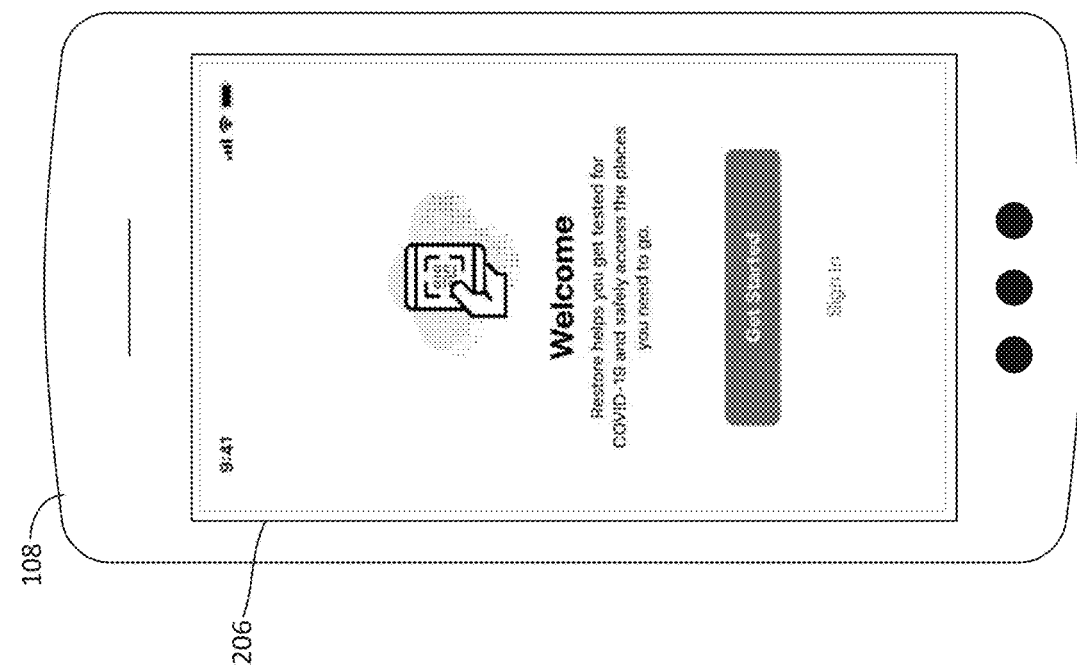
Figure 9:
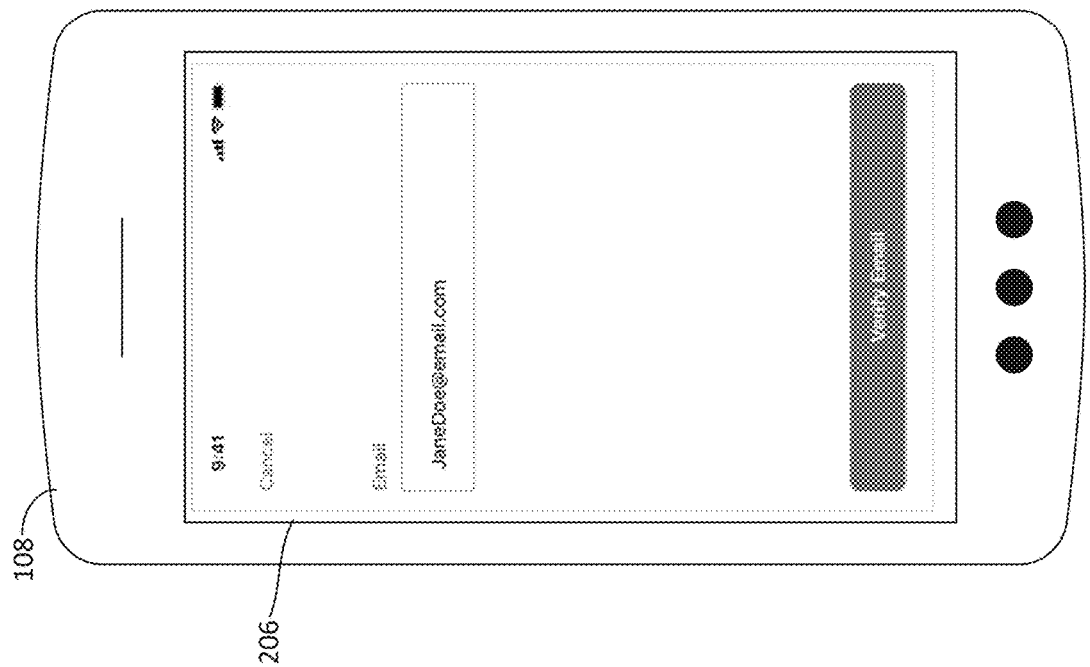
Figure 8:
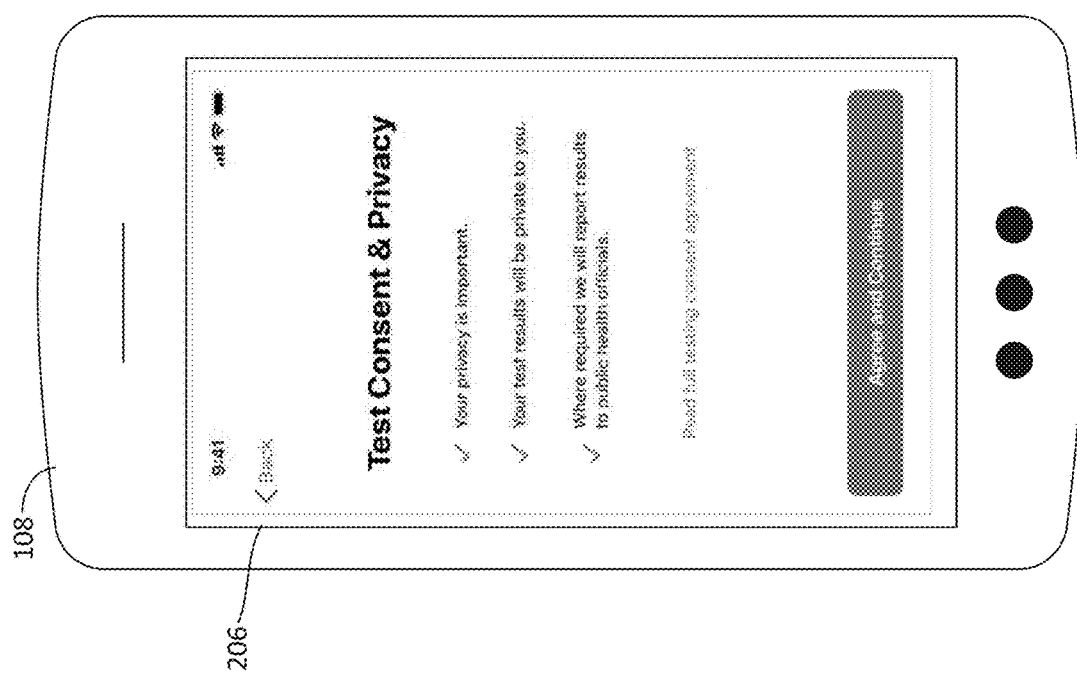

FIG. 5 is a block diagram of the example digital pass management system 100. In some examples, the digital pass management system 100 is an application server that supports the applications executed on the other devices. The digital pass management system 100 includes an example processor 500, an example database 502, an example record generator 504, an example validator 506, and an example transceiver 508. The database 502 can store information regarding users, tests, etc., and/or records generated by the record generator 504 as disclosed in further detail herein. In some examples, the digital pass management system 100 is owned, controlled, and/or otherwise operated by the verifier entity. For example, if the verifier entity is an airline, the digital pass management system 100 can be controlled by the airline. As another example, if the verifier entity is an office, the digital pass management system 100 can be controlled by the office. In other examples, the digital pass management system 100 can be controlled or operated by the testing entity. For example, the digital pass management system 100 can be provided by a hospital or medical facility. In other examples, the digital pass management system 100 can be operated by a different entity not related to the verifier entity and/or the testing entity. For example, the digital pass management system 100 could be owned by an entity or company that licenses the applications and/or data from the digital pass management system 100 to different verifier organizations (e.g., airlines, schools, offices, etc.). In some such examples, the verifier organizations may have access and/or control to certain data and/or reporting (e.g., identity of the testers, test results, etc.), while the company owning the digital pass management system 100 may be responsible for operating the backend datasets and environments in which the system(s) operate.

The verifier organizations may have separate accounts within the digital pass management system 100. The verifier organizations may be able to access their account information (e.g., via an application on a device, such as a computer) to add, remove, edit, etc. users or user profiles as well as modify various parameters (e.g., digital pass expiration times, testing frequency, verification rules, approved testing sites, etc.) associated with the digital pass verification system for the respective verifier organization. The verifier organizations can also sync the digital passes with employment records so that digital passes of employees that have left employment can be deactivated. The verifier organizations may be operated by one or more designated persons from the verifier organization (e.g., a human resources (HR) personnel).

In some examples, the digital pass management system 100 enables the verifier organization to view its list of users/participants and their associated information (e.g., ID, digital pass statuses, statuses of creating an account, statuses of getting tested, etc.) and generate reports (e.g., a report indicating people who are able to work). For example, the verifier organization can generate reports of the users that tested positive, negative, and/or invalid, and/or can be filtered by certain dates or ranges (e.g., all users that tested positive between two dates). In some examples, the verifier organization can send the reports to a local, state, or federal government agency (e.g., the Center for Disease Control (CDC)), another business, another verifier organization, and/or any other entity (e.g., a parent-teacher association). In some examples, the verifier organization manually generates and sends (e.g., via email) the reports. In other examples, the digital pass management system 100 automatically generates and sends the reports (e.g., once a week, once a month, etc.). In some examples, the report generation and/or sending could be triggered by an event, such as a request by an outside entity (e.g., a request from the CDC). In some examples, the digital pass management system 100 accesses results of diagnostic tests, receives sets of user identifications and test kit identifications from one or more second devices (e.g., tester devices), generates a report based on the results and receipt of the sets of user identifications and test kit identifications and transmits the report to a government agency.

In some examples, the digital pass management system 100 may send out invites to the users to be added to the verifier organization. For example, a place of employment (a verifier organization) can create a verifier organization account and send out invites to all of its employees (users) to create user accounts via the user application 116. Invitations may also be sent to new hires. The invites may be sent via email or text, for example. The invites may include a unique link or token code to link/associate the user's account with the verification organization account. Additionally or alternatively, a user may be able to search for certain verifier organizations via the user application 116 and then associate his/her account with the verification organization's account. In some examples, one or more of the users may be granted administrative control to access and/or modify the verifier organization account information. In some examples, a verifier organization can assign different levels of access to different users based on various roles. The digital pass management system 100 can be remote to the tester 104 and/or the verifier 106. One or more operations disclosed herein as being implemented by the applications can be partially or fully executed at the digital pass management system 100.

An example of a digital pass verification process is described below in connection with the interface screens in FIGS. 6-38. The example process is described in connection with the user 102 being tested for COVID-19. However, it is understood that the example process could be similarly performed in connection with assays for detection for any analyte of interest including analytes associated with the presence of an infectious disease and/or for multiple tests or assays for multiple analytes of interest or diseases.

Figure 36:
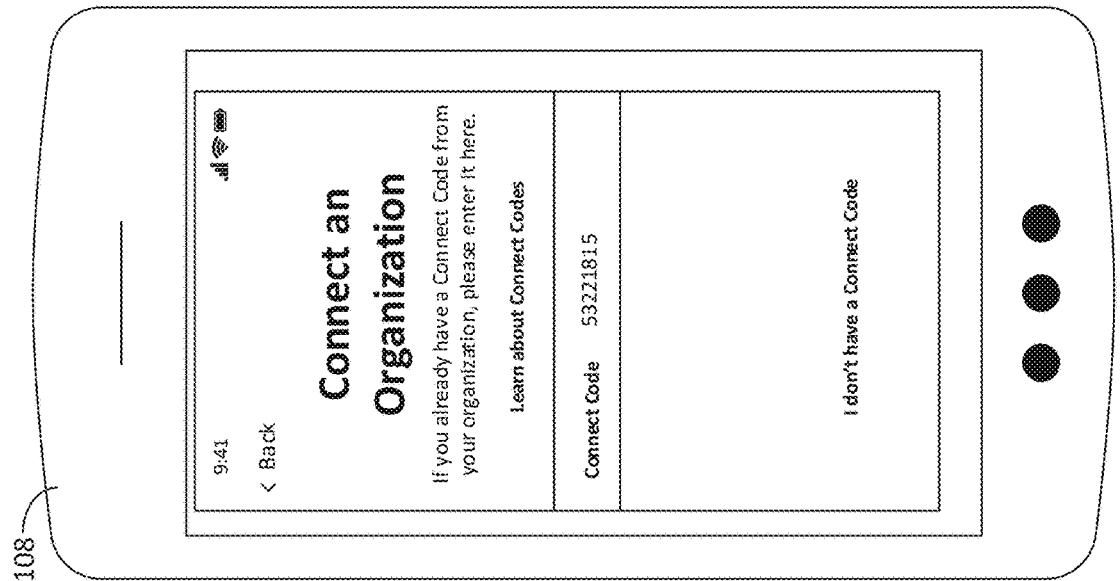
Figure 38:
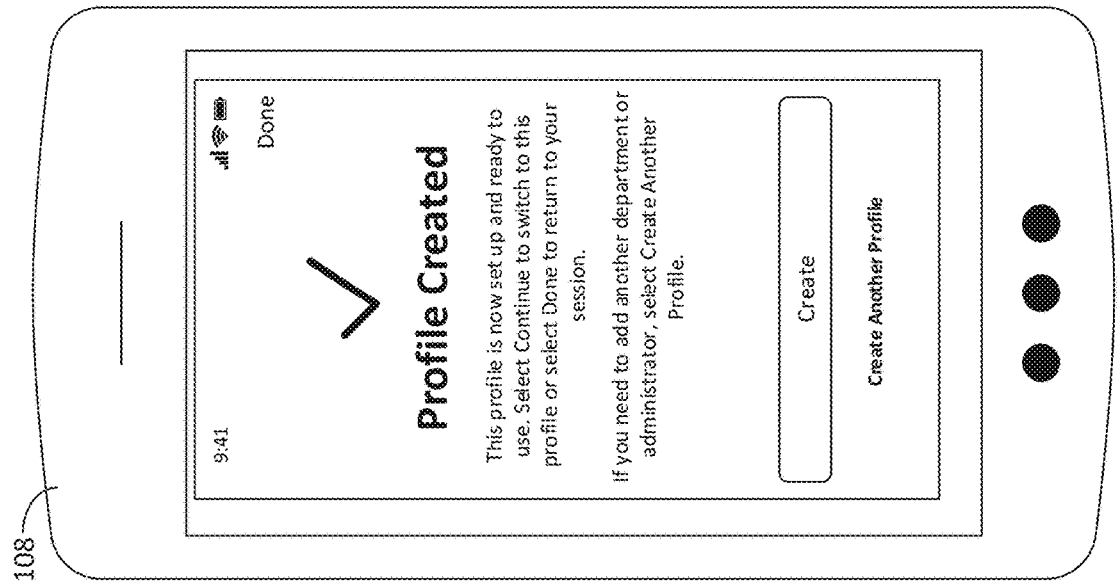
Figure 37:
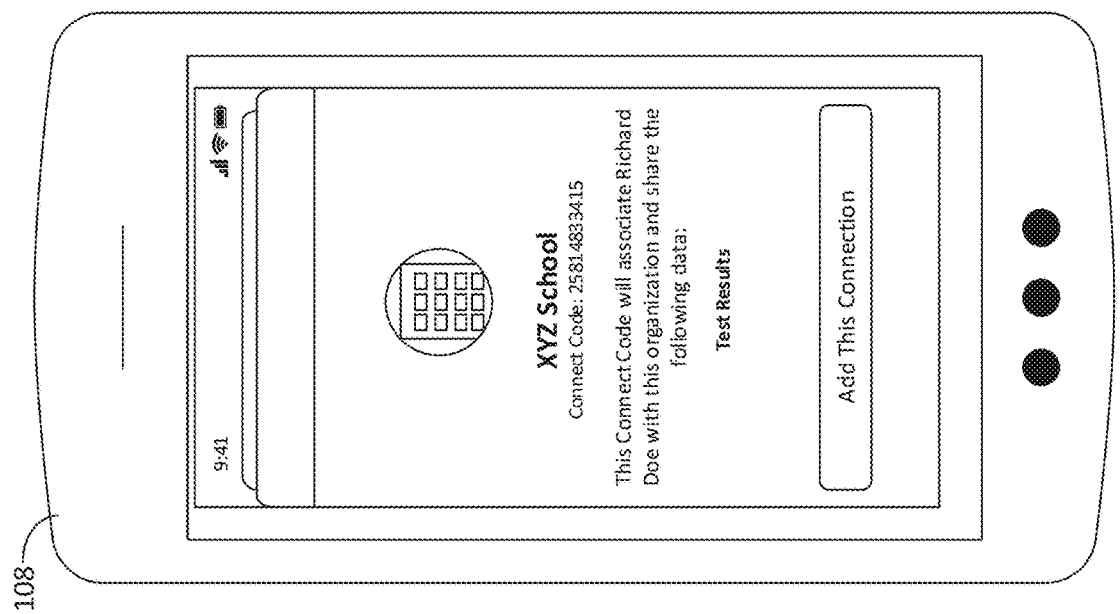

As disclosed above, the user 102 may download the user application 116 on the user device 108. In some examples, the user 102 opens the user application 116 on the user device 108 and creates an account with the digital pass management system 100, such as by agreeing to terms and conditions, agreeing to test consent and privacy conditions, entering identifying information (e.g., name, age, email, etc.), and creating a username and password. In some examples, the user 102 creates an account in response to receiving an invite from a verifier organization and/or a tester. For example, the user's employer may send out invites (e.g., via email, via text, etc.) to all employees to create an account using the user application 116. The unique link or token code may cause the application to open on the user device 108, or if not installed, prompt the user 102 to install the user application 116 on the user device 108. Additionally or alternatively, invite may include a unique link or token code to associate with the verifier organization. An example of this is shown in FIGS. 36-38 and disclosed in further detail below. In some examples, the user 102 uses a username and password that the user already has established with the verifier 106. For example, if the verifier 106 is a place of business such as the user's employer, the user 102 may use the username and password used to access their employer's computer network.

FIGS. 6-11 show example interface screens presented by the user application 116 on the display 206 of the user device 108 for creating an account with the digital pass management system 100. The user 102 can enter his/her email address (and/or a username) and create a password to create an account. After creating an account, the user 102 may use his/her email address (and/or username) and password to sign-in and access his/her information via the user application 116. The user 102 can manually enter his/her identifying information (e.g., name, address, etc.) in to the user device 108 to create an account. In some examples, in addition to or as an alternative to manually entering the user information, the user 102 can scan (e.g., a barcode on the ID) or take a picture of his/her driver's license or other form of ID (e.g., an employee ID card) to enter his/her user information into the user application 116 automatically. For example, the user 102 can use the camera 207 (FIG. 2) of the user device 108 to scan or take a picture of the ID. The information may include the user's full name, address including zip code, date of birth, gender, license number, etc. Additionally or alternatively, the user 102 can manually enter his/her information, such as if the user 102 does not have a phone. In some examples, additional information such as the user's race and/or ethnicity may be entered into the user application 116. This information may be stored in the database 502 with user's account. In some examples, this information is used to support state reporting (e.g., determining metrics of infected demographics).

The user application 116 uses the transceiver 204 to send the account information to the digital pass management system 100 (e.g., via the Internet). The record generator 504 of the digital pass management system 100 creates an account for the user 102 in the database 502. An example record or data entry 510 for the user account is shown in FIG. 5. As shown, the data entry 510 can include the user's name, date of birth (DOB), email address, and/or other identifying information. The record generator 504 of the digital pass management system 100 also creates a unique user account ID (e.g., a serial number) for the user's account, as shown in the data entry 510 in FIG. 5. The user account ID can be used to identify the user 102 during the digital pass verification process. The digital pass management system 100 sends the user account ID to the user device 108, which can then be stored in the memory 202.

The user 102 then gets tested for the infectious disease or pathogen. In some examples, the user 102 schedules an appointment with the tester 104. In some examples, the user 102 uses the scheduler 208 in the user application 116 on the user device 108 to search for testing facility, to schedule an appointment with a testing facility, and/or schedule a telehealth session. The scheduler 208 may provide an interface that allows the user to search for testing facilities within a certain geographical location. In some examples, the scheduler 208 automatically returns testing facilities within a certain radius (e.g., 20 miles) of the user's zip code or location, which was obtained during the account setup process. In some examples only certain testing facilities that are approved by the verifier 106 are displayed (e.g., partner testing facilities). In some examples, the scheduler 208 interfaces with the testing facilities' schedule applications or programs to enable the user 102 to schedule an appointment through the user application 116. Additionally or alternatively, the scheduler 208 may provide a link to access the testing facilities' sites for scheduling. The scheduler 208 can provide a link to telehealth services to order tests and/or schedule a telehealth session. The scheduler 208 may save the scheduled appointment with the user account in the memory 202 of the user device 108 and/or in the database 502 with the user's account. In some examples, the notifier 210 in the user application 116 provides reminders or alerts to the user when an appointment is approaching. In other examples, the user 102 can use another application to schedule the test or schedules the test without an application such as, for example, by calling the tester 104 or testing facility. In still other examples, the user 102 does not schedule an appointment, but merely arrives at the testing facility to be tested. In some examples, the tester application 118 provides the tester 102 with a schedule of all the scheduled tests. In some examples, the tester application 118 supports appointments from within the organization and/or from outside of the organization.

Figure 13:
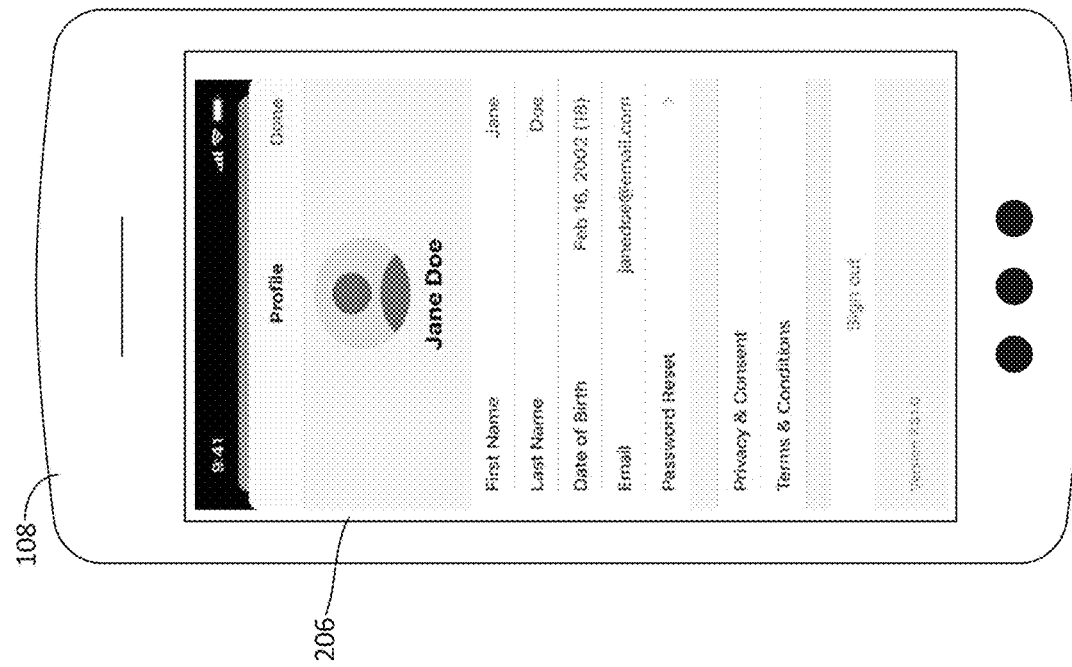
Figure 12:
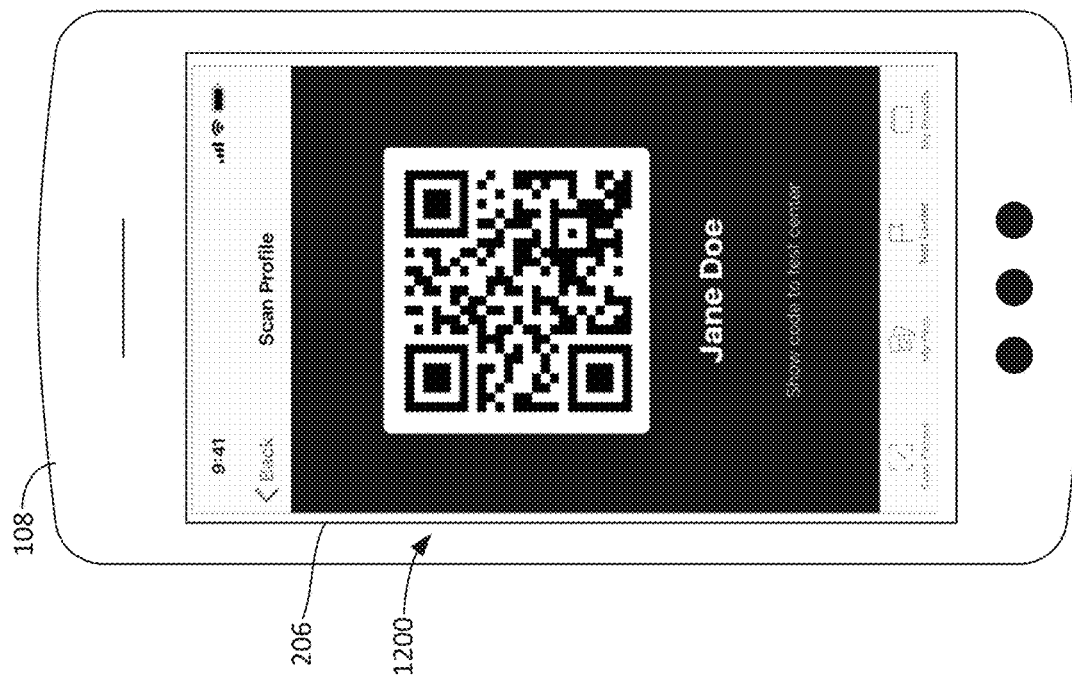

In some examples, to help identify the user 102 and link the user's test to the user's account, the code generator 212 of the user application 116 generates an identity code, such as a machine-readable code. In some examples, the identity code may be a 1D code such as a bar code. In some examples, the identity code may be a 2D code such as a Data Matrix Code or a QR code. Other examples may use other types of codes or combinations of codes including, for example, other machine-readable codes. In some examples, the identity represented in the code contains the user account ID for the user 102. In particular, the code generator 212 of the user application 116 converts the user account ID into the code format. The identity code is displayed on the user device 108 so that the user 102 can present the identity code to the tester 104. FIG. 12 shows an example identity code 1200 presented on the display 206 of the user device 108. In this example, the identity code 1200 is a QR code. However, in other examples, the identity code 1200 can be another type of code. In some examples, the identity code 1200 is presented in response to a user selection to present the identity code 1200 (e.g., selecting a "Display ID" button on the display 206). FIG. 13 shows another example interface on the display 206 of the user device 108 showing the profile of the user 102.

Figure 15:
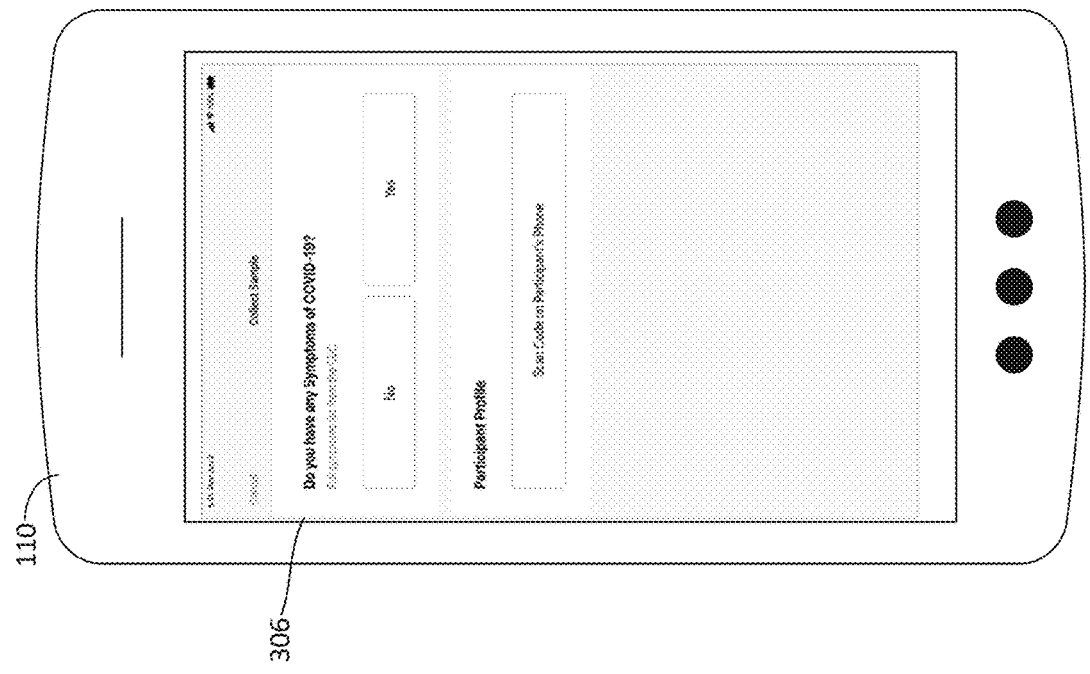
Figure 14:
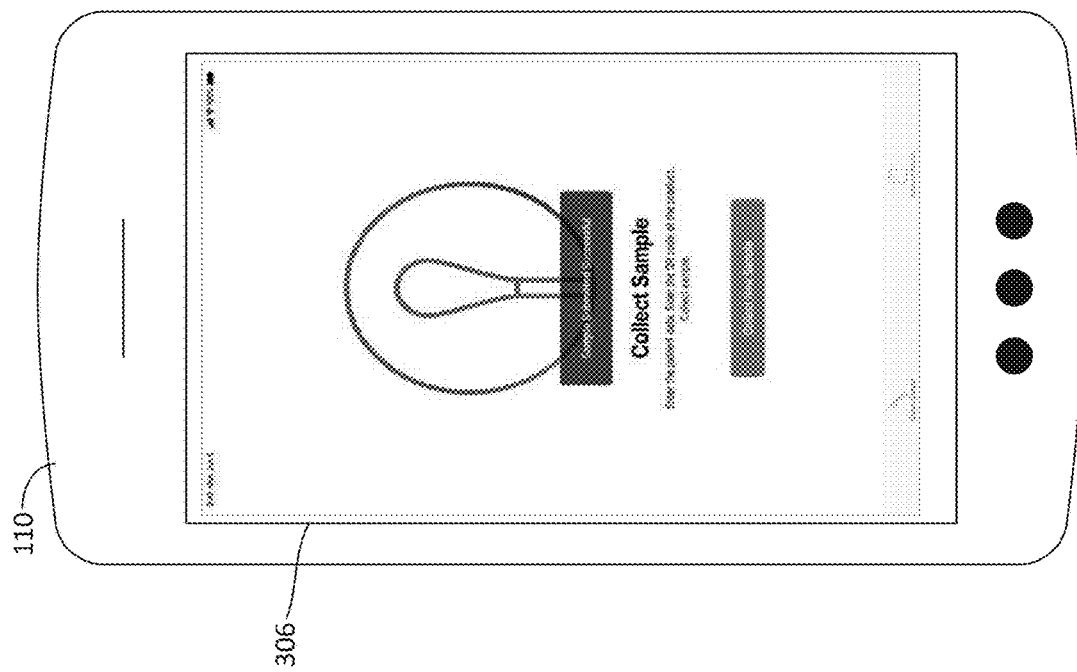

FIGS. 14-25 show example interface screens presented on the display 306 of the tester device 110. The tester 104 uses the record generator 310 of the tester application 118 to create a test record for the user 102. FIGS. 14 and 15 show example interface screens presented by the tester application 118 on the display 306 of the tester device 110 for the creation of a new test record. In some examples, the tester 104 logs into the tester application 118 with a unique login name and/or password. In some examples, as shown in FIG. 15, the tester 104 can ask the user 102 if he/she has experienced any symptoms. The tester 104 can enter the results into the tester application 118. Additionally or alternatively, the user 102 could enter his/her results into the tester application 118 on the tester device 110 or into the user application 116 on the user device 108. In some examples, the user 102 is prompted with targeted questions directed to particular physiological conditions, behaviors, and/or activities. In some examples, the tester application 118 provides a link to a list of symptoms provided by the Center for Disease Control and Prevention (CDC). In other examples, the symptoms are stored in the memory 302. In some examples, the tester application 118 prompts the tester 104 to gather information from the user 102 regarding the user's travel history, health conditions and/or history, family health history, lifestyle, etc.

In some examples, details related to the user's symptoms, user's travel history, health conditions and/or history, family health history, lifestyle, etc. are presented to the user 102 via the user application 116 and stored in the memory 202 of the user device 108. In some examples, some or all of this information may be shared between the user application 116 and the tester application 118. In some examples, some or all of this information may be shared between the user application 116 and digital pass management system 100.

Figure 17:
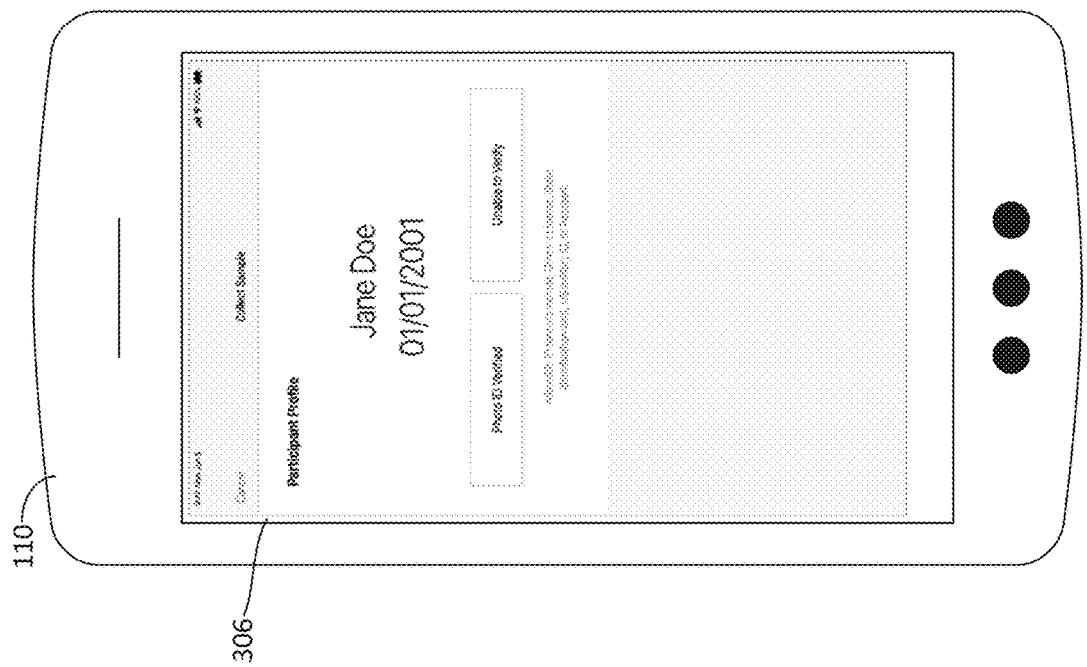
Figure 16:
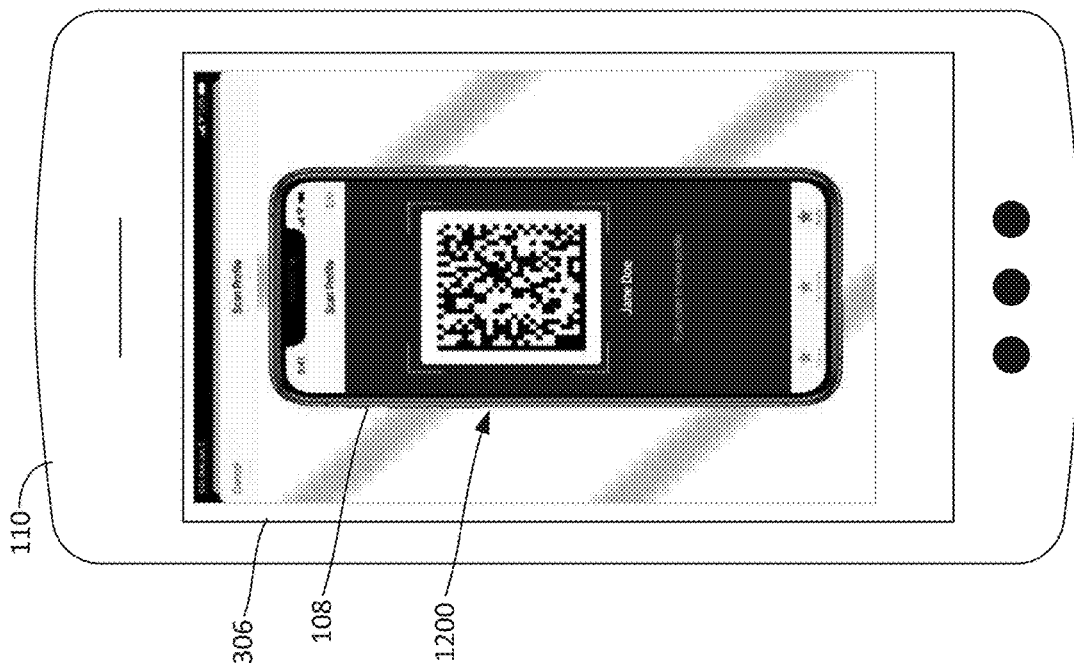
Figure 18:
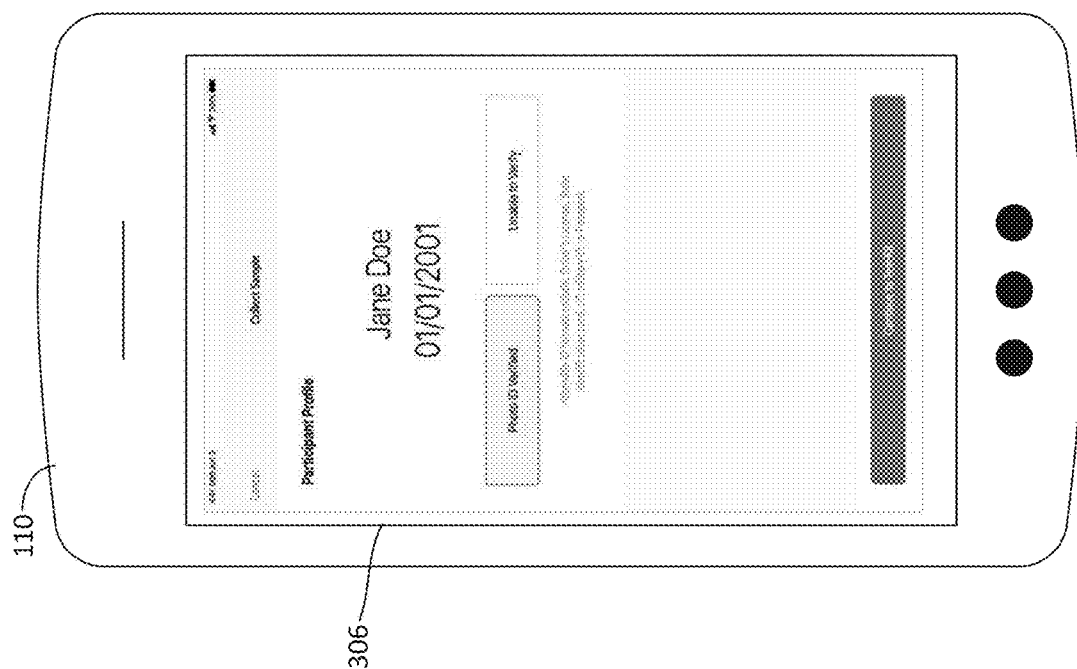

To identify the user 102, the tester 104 uses the camera 308 of the tester device 110 to scan the identity code 1200 on the user device 108. For example, FIG. 16 shows the display 306 on the tester device 110, which is displaying the view from the camera 308. The tester 104 aligns the user device 108 in the view of the camera 308. The tester application 118 detects and interprets the identity code 1200 to obtain the user account ID. The tester application 118 sends the user account ID to the digital pass management system 100. The digital pass management system 100 searches the database 502 for the corresponding record (e.g., the data entry 510) and returns the name and/or other identifying information of the user 102. For example, FIG. 17 shows the name of the user "Jane Doe" and user's birthday "Jan. 1, 2001" on the display 306 of the tester device 110. In some examples, the tester 104 may ask the user 102 for physical identification (e.g., a driver's license, a state ID, etc.) to confirm the user's identity. The user 102 may show his/her identification to the tester 104. If the ID matches the name and birthday on the tester device 110, the tester 104 can then select "Photo ID Verified" as shown in FIG. 18. If not, the tester 104 can select "Unable to Verify." In some examples, if the user 102 does not have his/her user device 108, the user 102 can use his/her ID or other identifying means to confirm their identity with the test 104. In some examples, the user 102 may enter his/her username and/or password into the tester application 118 on the tester device 110.

In some examples, the tester 104 uses the camera 308 to scan the user's driver's license or other ID (e.g., take a picture of the ID, scan a code (e.g., a barcode) on the ID, etc.). The record generator 310 can create a record based on data obtained from the scanned ID and/or communicate with the digital pass management system 100 to obtain a record based on data obtained from the scanned ID. Additionally or alternatively, in some examples, the user 102 can scan his/her driver's license or other ID with the user device 108 (e.g., with the camera 207 of the user device 108). In such an example, the user application 116 can create a record with data obtained from the scanned ID and/or communicate data to the tester device 110 and/or digital pass management system 100.

The test to be performed is a medical diagnostic test including, for example, a rapid diagnostic test (RDT). The diagnostic test detects a presence or an absence of an analyte of interest, such as an infectious disease, a pathogen, an antibody, etc. The test can be performed using any type of testing kit, device, and/or equipment. Different tests may require different types of samples from a user. A sample can include a nasal swab, an oral fluid swab, blood, urine, etc.

The test or assay can be any test or assay able to detect an analyte of interest. The analyte can be monovalent (monoepitopic) or polyvalent (polyepitopic), synthetic or natural, antigenic or haptenic, and may be a single compound or plurality of compounds which share at least one common epitopic or determinant site. The analyte can be a nucleic acid, a protein, a nucleocapsid protein, an antibody or an antigen. The analyte can be a part of a cell such as bacteria or a cell bearing a blood group antigen such as A, B, D, etc., or an HLA antigen, plasma membrane receptors or a microorganism, e.g., bacterium, fungus, protozoan, or virus. The analyte can also be a chemical compound, such as a drug or a metabolite thereof. In some examples, the test is an assay to detect an analyte associated with an infectious disease.

In some examples, the test is performed using a disposable test kit, such as a disposable lateral flow test kit. An example disposable lateral flow test kit that may be used is the BinaxNOW® test kit manufactured by Abbott Laboratories, having headquarters in Abbott Park, Ill., USA. In some examples, each test kit contains a unique test kit ID (e.g., a serial number), which may be generated by the manufacturer and/or distributer. The test kit ID may be displayed as a test kit code (e.g., a machine-readable code, such as a QR code) on the test kit. In other examples, the test may be performed using a laboratory analyzer device (e.g., a molecular or clinical chemistry analyzer device). In some examples, the test may be performed using a point of care laboratory analyzer device such as the ID NOW™ analyzer manufactured by Abbott Laboratories. In some examples, test cartridges are used with the laboratory analyzer device. In some such examples, each cartridge contains a unique test kit ID generated by the manufacturer and/or distributer.

In some examples, the test selector 312 of the tester application 118 analyzes the information provided including, for example, user symptoms, travel history, health conditions and/or history, family health history, lifestyle, etc. to determine what diagnostic tests should be performed. For example, the test selector 312 may determine what analyte of interest or infectious diseases a user may have been exposed to based on the data derived from the user's information. The sample indicator 314 prompts the tester 104 as to what sample or samples to gather from the user 102 based on the test determined by the test selector 312. For example, if the test selector 312 determine that the user 102 should be tested for COVID-19, the sample indicator 314 prompts the tester 104 to gather a sample of nasal secretions using, for example, a nasopharyngeal swab.

Figure 19:
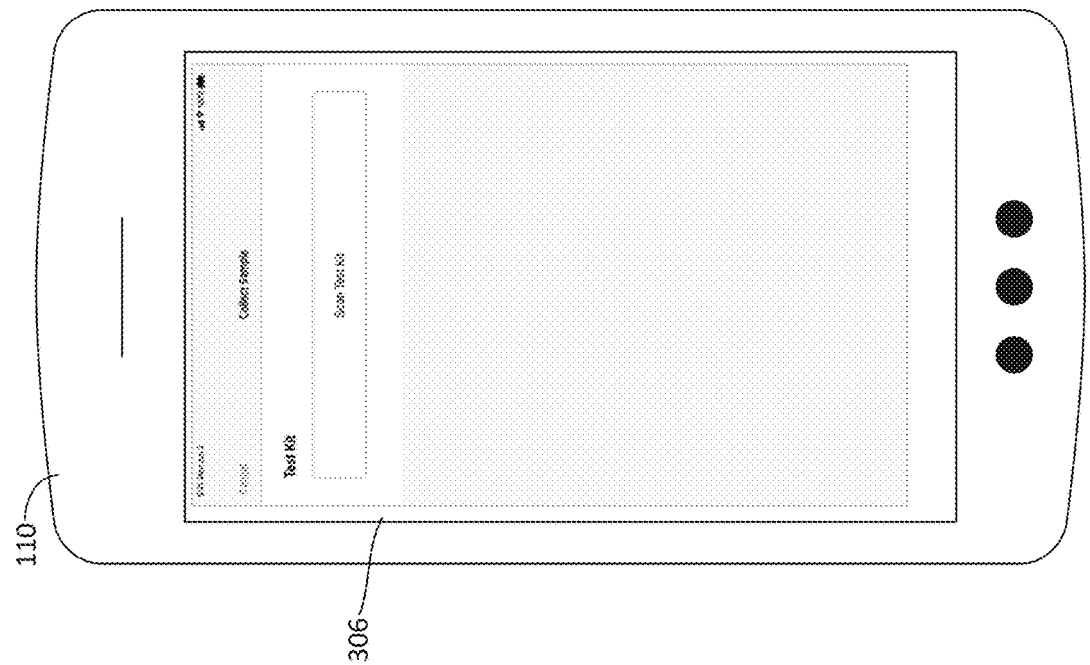

When the tester 104 is ready to perform the test, the tester 104 can scan a code on the test kit. In some examples, the tester 104 selects an option on the screen of the tester device 110 such as, for example, "Scan Test Kit" as shown in FIG. 19. The tester 104 uses the camera 308 on the tester device 110 to scan a test kit code 2000 on a test kit 2002, as shown in FIG. 20. Additionally or alternatively, tester 104 can use another device to obtain scan the test kit code 2000, such as a mounted or a handheld scanner that is communicatively coupled to the tester device 110. In this example, the test kit 2002 is a disposable lateral flow test kit. In other examples, such as when the test is to be performed using a laboratory analyzer device, the tester 104 can scan a test kit code on a test cartridge that is used to insert the sample into the laboratory analyzer device. In this example, the test kit code 2000 is a Data Matrix Code. In other examples, the test kit code 2000 can be another type of code, such as a bar code or a QR code.

The test kit code 2000 contains the test kit ID (e.g., a serial ID, lot ID, and/or expiration date from the manufacturer) associated with the test kit 2002. As disclosed herein, each test kit may include a unique test kit ID that is generated for every test kit. The record generator 310 of the tester application 118 detects and interprets the test kit code 2000 to obtain the test kit ID. The tester application 118 sends the test kit ID to the digital pass management system 100, which stores the test kit ID with the user's account. For example, as shown in FIG. 5, the data entry 508 includes a test kit ID and date of the test.

In some examples, the validator 506 of the digital pass management system 100 verifies or authenticates the validity of the test kit by comparing the test kit ID with a list of valid test kit IDs from the manufacturer. Test kits with IDs that are not included in a list of valid test kit IDs may be counterfeit. In some examples, the validator 506 of the digital pass management system 100 verifies the validity of the test kit by evaluating an expiration date of the test kit. In some examples, the validator 506 of the digital pass management system 100 verifies the validity of the test kit by evaluating a recall status of the test kit. In some examples, the validator 506 of the digital pass management system 100 verifies the validity of the test kit by evaluating if the test kit has already been used. If the validator 506 determines that a test kit is not a valid test kit, the digital pass management system 100 notifies the tester 104 (e.g., by exchanging communications between the transceiver 508 and the transceiver 304). After a test kit is used, the record generator 504 records the test kit as being used. Any attempt to use the test kit again will result in the validator 506 indicating that the test kit is not valid.

In some examples, before or after scanning the test kit code 2000, the tester application 118 displays instructions for how to obtain a sample from the user 102 and/or use the test kit 2000. The instructions are based on what sample type the sample indicator 314 selected for the test. For example, FIG. 21 shows an interface screen with a procedure for collecting the sample and performing the test with the test kit 2000. In some examples, the instructions are specific to the type of test kit or test cartridge that has been scanned.

In some examples, the test is performed at the point of care. That is, the test is performed at the location where the sample was gathered from the user, such as for example, at the testing facility or a medical office or clinic. In some examples, a sample is gathered and a test is performed at the user's home. In other examples, the sample is shipped to a remote location, and the test is performed at the remote location. For example, the testing facility may obtain the sample from the user 102 and ship the sample to the remote testing facility. As another example, the user 102 may obtain his/her own sample (e.g., from an at-home sample kit) and ship the sample the remote testing facility. In some examples, such as with a disposable lateral flow test kit, the results are provided via a visual indication (e.g., one or more lines or colors) on the test kit. In other examples, such as with a laboratory analyzer device, the results are provided on a digital screen of the laboratory analyzer device.

Figure 22:
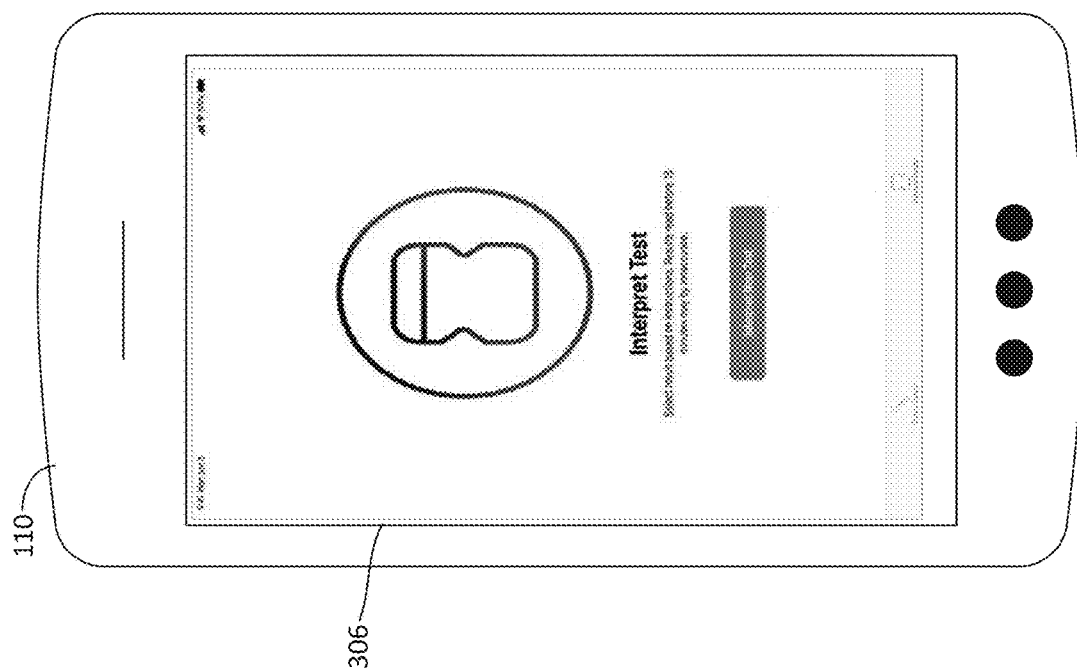

When the test is complete, the tester 104 interprets the test results. For example, via the tester application 118, the tester 104 can select "Interpret New Test" as shown in FIG. 22 to enter the results. In some examples, the tester 104 interpreting the results of the test is the same tester 104 who gathered the samples (in this context "same tester" means the same facility though the individual obtaining the sample and the individual interpreting results are two different people). In some examples, the tester 104 interpreting the results of the test is different than the tester 104 who gathered the sample. For example, the tester 104 who gathered the sample may be a medical facility such as, for example, a doctor's office, and the tester 104 who interprets the results may be a lab technician at a diagnostic laboratory.

Figure 23:
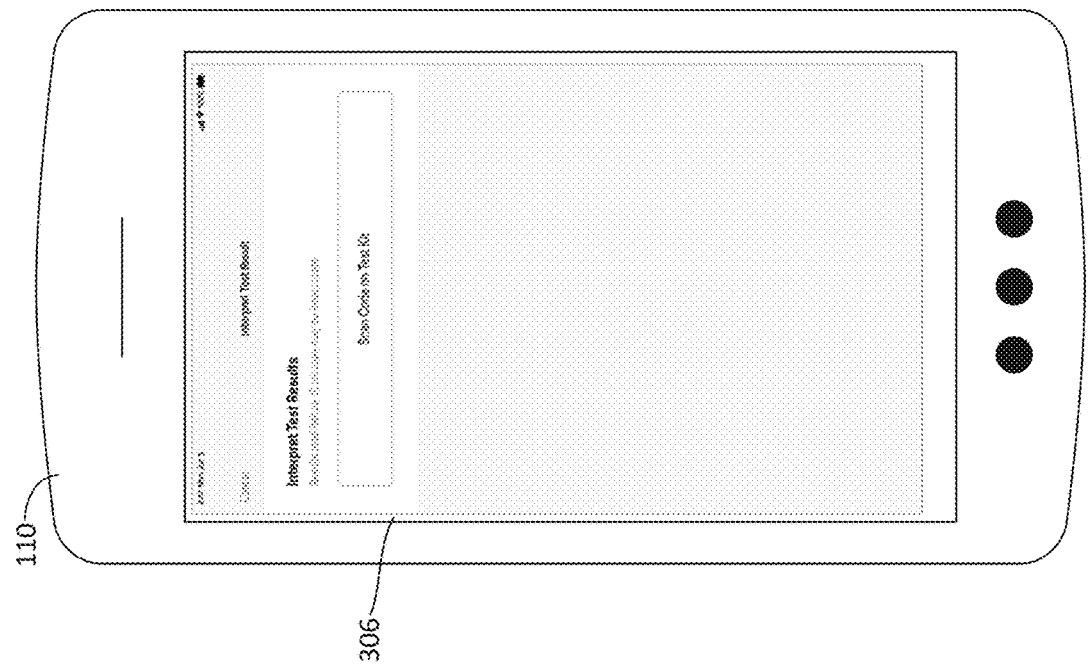
Figure 24:
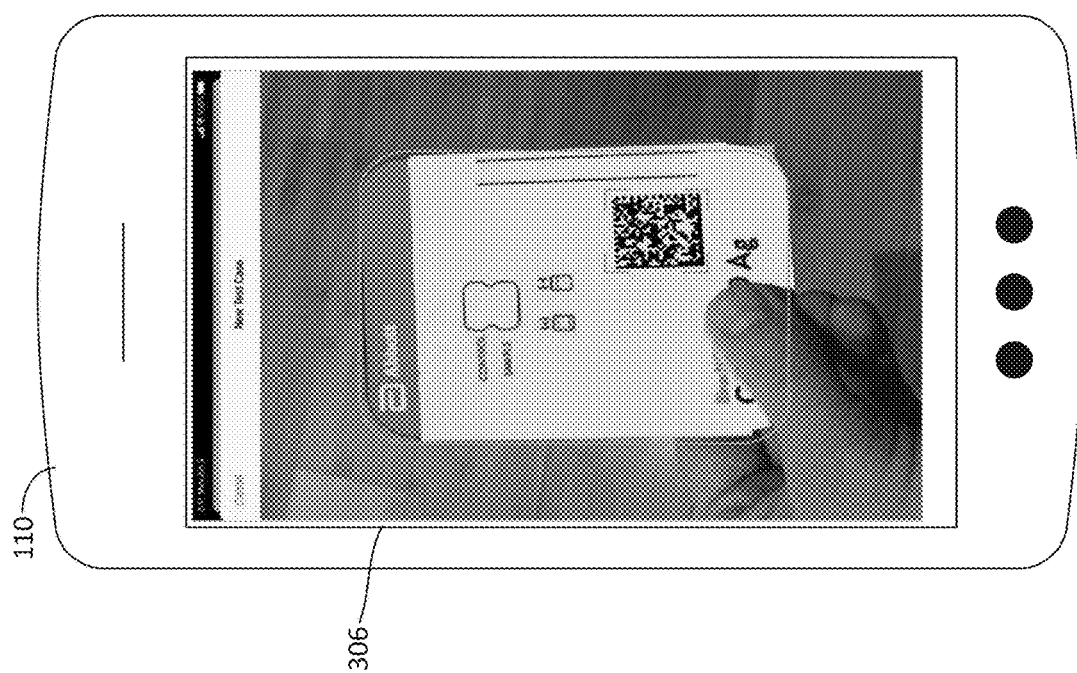

In some examples, when viewing and/or interpreting the results, the tester 104 scans the test kit code 2000 on the test kit 2002 again, as shown in FIGS. 23 and 24. In some examples, scanning the test kit code 2000 after the test is complete confirms the same test kit 2000 that was used to perform the test is the same test kit that is being interpreted. In some examples, the comparator 316 of the tester application 118 compares the two test kit IDs. Additionally or alternatively, in some examples, the test kit IDs are sent to the digital pass management system 100 for comparison by the validator 506. In other examples, a second scan of the test kit ID is not performed.

Figure 25:
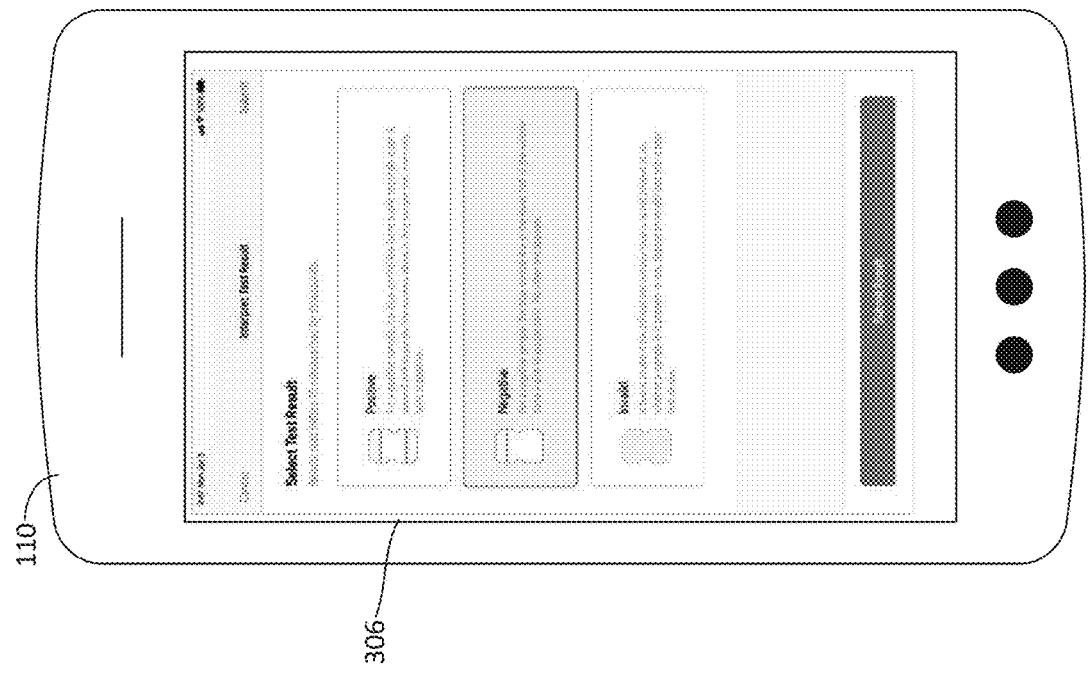

In some examples, the tester application 118 provides a notification for the interpretation and entry of the result of the diagnostic test. For example, the tester application 118 can present the tester 104 with selectable options for the results of the test, as shown in FIG. 25. In this example, the options include positive, negative, and invalid (or inconclusive). In some examples, as shown in FIG. 25, the options include graphics that match the visual indicators on the test kit 2002. The tester 104 reviews the test results from the test kit 2002 and selects the matching result. The tester application 118, using the transceiver 304, sends the results along with other identifying information to the digital pass management system 100, where the record generator 504 adds the results to the user's account in the database 502, including the date of the test.

In other examples, the camera 308 can be used to obtain an image of the test kit 2002, and the reader 318 of the tester application 118 analyzes the image to automatically interpret the results. In such examples, the tester 104 does not need to enter the results into the tester device 110. In other examples, such as with a diagnostic test performed by a laboratory analyzer device, the laboratory analyzer device may automatically send the results to the tester application 118 and/or the digital pass management system 100.

In some examples, the tester 104 takes a picture of the used test kit 2002 (or at least a portion of the test kit 2002) as evidence of the results. In some such examples, the picture of the used test kit 2002 is saved in the database 502 with the user's account (as shown in FIG. 5) and/or can be sent to the user 102 as evidence and/or for record keeping. For example, the transceiver 508 can transmit at least a portion of the test kit 2002 to the user device 108.

The record generator 504 of the digital pass management system 100 adds the results to the user account. For example, the data entry 510 in FIG. 5 shows the result "Negative" saved with the user account. In some examples, other information can also be stored in the user account, such as, for example, the name and location of the testing facility that performed the test, the ID of the tester 104, an image of the test kit code, whether the user 102 has any symptoms, an image of the test kit when reviewing the results (for records), etc. The digital pass management system 100 sends the results and/or other information (e.g., the test kit ID) to the user application 116 on the user device 108 by, for example, exchanging communications between the transceiver 508 and the transceiver 204.

Figure 26:
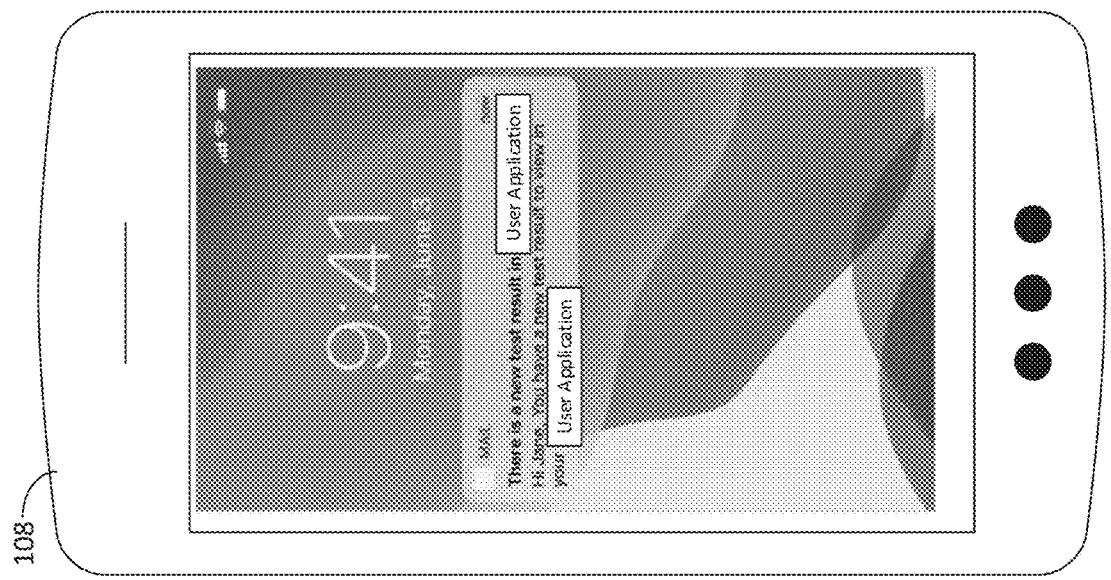

The user application 116 can then access the test results. In some examples, the test results are sent to the user device 108 via a text, an email, a URL link, etc. In other examples, the test results are pushed to the user application 116. For example, FIG. 26 shows an example push notification on the user device 108 indicating new results have been received. The user 102 may review the results via the user application 116 or other means on the user device 108, as shown in FIG. 27A. As shown in FIG. 27A, the user application 116 displays information relating to the test, such as the date of the test, the name of the user 102, and the result of the test. In some examples, the digital pass management system 100 sends other information to the user device 108 such as, for example, the test kit ID that was used to perform the test, the location of the test, the ID of the tester 104, etc. For example, FIG. 27B shows another example interface that may be displayed by the user application 116. The interface shown in FIG. 27B includes the date of the test, the name of the user 102, the result of the test, and the test kit ID (including the lot and serial number). This information may be stored in the memory 202 with the results on the user device 108.

The analyzer 216 of the user application 116 determines what the test results are (e.g., positive, negative, or invalid/inconclusive). In some examples, in addition to displaying the results, the notifier 210 of the user application 116 on the user device 108 can present instructions or guidelines (e.g., the CDC guidelines) relating to the infectious disease and/or the results. If the results are negative, for example, the post-testing instructions may be minimal. For example, FIG. 27A shows a list of guidelines for the user 102 to follow. The guidelines may be updated as new guidelines are released. If the results are positive, for example, the post-testing instructions may include recommending a doctor's appointment, a follow-up exam, further testing, quarantine, and/or other actions. In some examples, prior to issuing a positive result, the tester 104 may call the user 102 to alert the user 102 immediately and personally about the positive result.

Figure 28B:
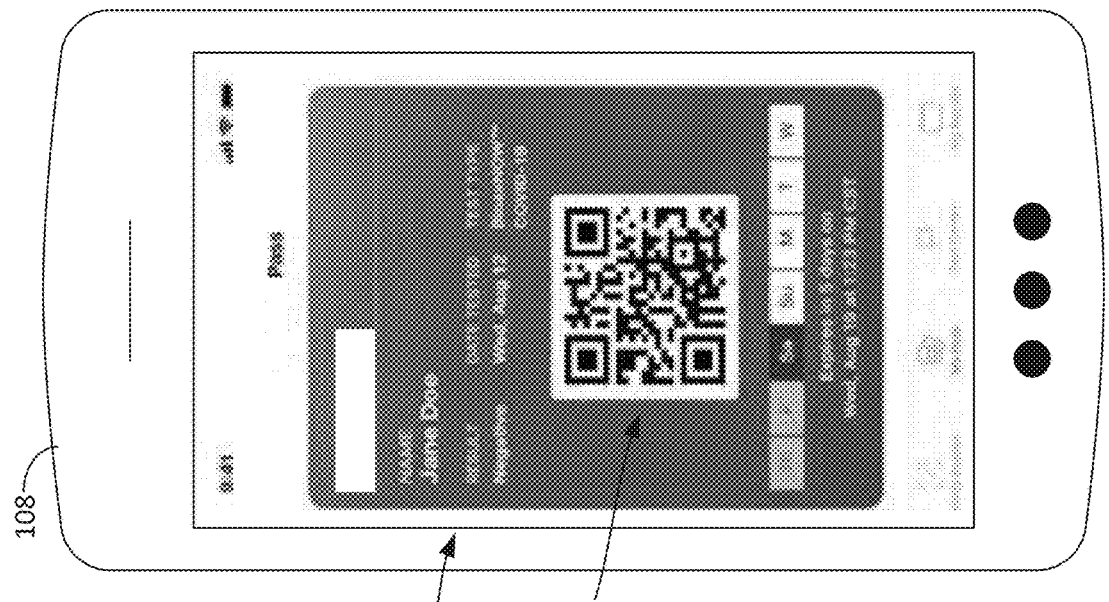
Figure 28A:
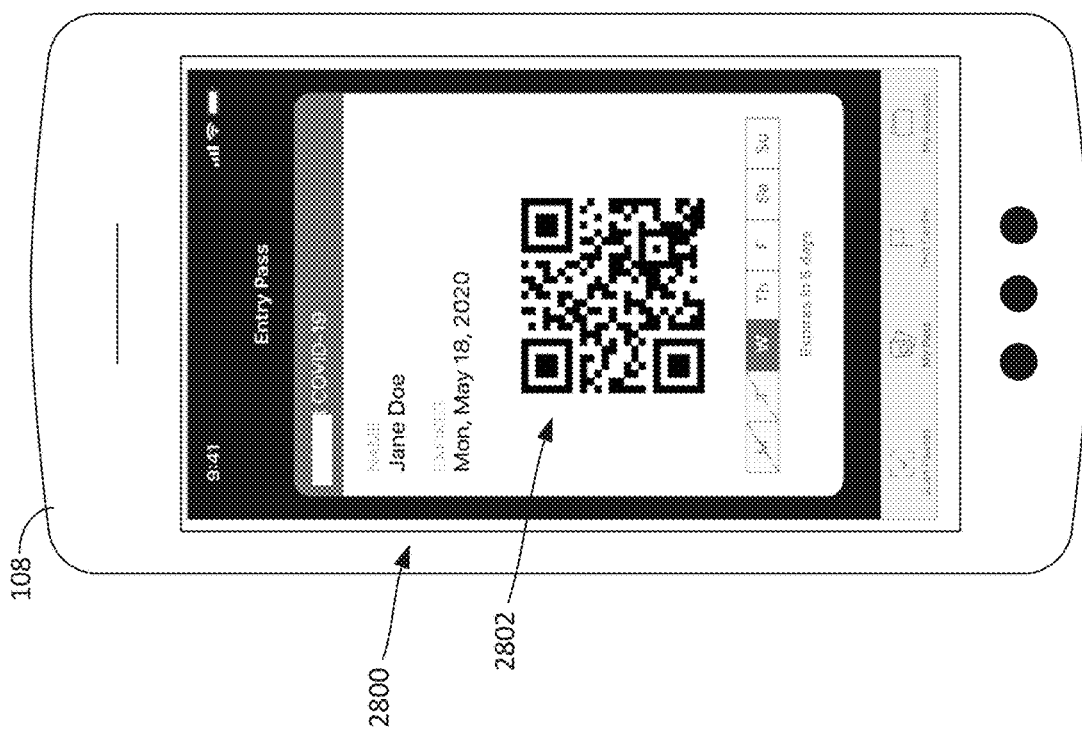

If the analyzer 216 determines that the results are negative, the code generator 212 of the user application 116 on the user device 108 generates a digital pass 2800, as shown in FIG. 28A. In other words, when the analyzer 216 determines that a test result is negative, the generation of a digital pass is triggered. The digital pass 2800 is a record that the user 102 tested negative for the infectious disease and/or analytes associated with the infectious disease. The digital pass 2800 can be used to confirm with a verifier that the user 102 tested negative for the infectious disease, as disclosed in further detail herein. In some examples, the user 102 can access the digital pass(es) by clicking "Go to My Pass" as shown in the interfaces in FIGS. 27A and 27B.

If the analyzer 216 determines that the results are positive or invalid (inconclusive), no digital pass is generated. In some examples, the notifier 210 may alert the user 102 that no digital pass is to be generated because of the test results. In some examples, the notifier 210 provides an indication within the user application 116 that there is no valid digital pass.

If analyzer 216 determines the results are negative, the code generator 212 of the user application 116 generates the digital pass 2800 and saves the digital pass 2800 on the user device 108 (e.g., in the memory 202). In some examples, the digital pass 2800 is saved as part of a digital wallet on the user device 108 that can be accessed with or without the user application 116. In some examples, the digital wallet contains other digital passes (e.g., for the same infectious disease and/or other infectious diseases) and/or other types of passes (e.g., airline boarding passes, movie tickets, etc.).

In some examples, the digital pass 2800 includes a digital pass code 2802. The code generator 212 of the user application 116 generates the digital pass code 2802. The digital pass code 2802 can be a machine-readable code. In this example, the digital pass code 2802 is a QR code. In other examples, the digital pass code 2802 can be another type of code, such as, for example, a bar code, a Data Matrix Code, and/or other types of machine-readable codes. In some examples, to generate the digital pass 2800, the code generator 212 communicates (via the transceiver 204) with the tester 104 and/or the digital pass management system 100 to access data related to the test kit ID and an object ID. The object ID is the ID of the user account. In some examples, the digital pass code 2802 includes the user account ID and the test kit ID associated with the diagnostic test. Thus, in some examples, the digital pass code 2802 includes information to identify the user 102. In other examples, the digital pass code 2802 can include other identifying information in addition to or as an alternative to the user account ID and the test kit ID. The digital pass code 2802 enables the verifier 106 to quickly, accurately, and safely obtain information from the user 102 that can be used to verify the user 102. The code generator 212 embeds the QR code (or other type of machine-readable code) into the digital pass 2800. In some examples, the code generator 212 adds further details to the digital pass 2800 including, for example, the user's name and an expiration date of the digital pass 2800. The output 218 sends the digital pass 2800 to the display 206 for presentation by the user 102.

In some examples, the digital pass 2800 has an expiration date or time, which represents a threshold number of days or time that the digital pass 2800 is still valid. After the expiration date or time, the digital pass 2800 is no longer valid. In some examples, the example time comparator 214 monitors time to determine when an expiration date or time is approaching or has passed. The expiration date may be a predetermined number of days after the test, such as five days, seven days, ten days, etc., for example. In other examples, the expiration may be based on a certain time (e.g., 30 hours from the diagnostic test). In some examples, the expiration date or time is based on a pathogen incubation period or contagious period. In some examples, the expiration date or time is set by the organization or entity associated with the verifier 106. The scheduler 208 monitors the dates and/or times of expiration of the digital passes. In some examples, as shown in FIG. 28A, the user application 116 displays a calendar showing the current day and the number of days until the digital pass 2800 expires. Additionally or alternatively, the user application 116 may display a live ticker, such as a day and/or time counter that counts to the expiration date (e.g., by the day, by the hour, by the minute, but the second, etc.). This may enable the user 102 to easily determine how much time is left until expiration and plan to retake a test before the current digital pass 2800 expires. In some examples, if the scheduler 208 determines that the digital pass 2800 has expired, the notifier 210 notifies the user 102 that the pass has expired. In some examples, if the scheduler 208 determines that the digital pass 2800 is about to expire, the notifier 210 notifies the user 102 of the upcoming expiration. Thus, the scheduler 208 determines a validity of the digital pass based on the expiration date. In some examples, the notifier 210 notifies the user 102 to schedule another test before and/or after the expiration of the digital pass 2800. For example, if the number of days left before expiration drops below a threshold (e.g., one day), the scheduler 208 can display a notification or reminder to schedule a new diagnostic test. Therefore, the scheduler 208 can display a notification to the user 102 to schedule a second diagnostic test based on the number of days since the first diagnostic test and the threshold number of days. In some examples, if the user 102 is re-tested before a digital pass expires, a new digital pass is generated and the old digital pass is saved in a library that can be viewed for a certain amount of time. In some examples, the code generator 212 can automatically deletes or otherwise removes expired digital passes from the user application 116 when they expire. In other examples, if the user 102 takes another test and passes, the same digital pass 2800 can be updated and used again by extending the expiration date. In some examples, an expired digital pass can still be viewed for a threshold number of days or time after the expiration. For example, a digital pass may be viewable for up to seven days after expiration, after which the code generator 212 deletes or otherwise removes the digital pass. However, the result of the test and other information relating to the test can still be viewed in a results history interface. As disclosed in further detail herein, if the user 102 attempts to use an expired digital pass, the verifier device 112 can detect the expiration and deny the user 102 access to the verifier location.

In some examples, after the user application 116 receives the test result, and prior to generating the digital pass 2800, the time comparator 214 determines whether the expiration time or date has already passed. This may occur, for example, if there was a delay in testing or sending the results. In some examples, if the expiration has already passed, the code generator 212 does not generate the digital pass 2800. If the expiration date has not already passed, the code generator 212 generates the digital pass 2800 as disclosed herein. Therefore, in some examples, the code generator 212 generates the digital pass 2800 in response to the result being negative and the number of days (or time) since the diagnostic test being below a threshold number of days (or time).

FIG. 28B shows another example digital pass 2804 with an example digital pass code 2806 that can be generated by the code generator 212. The digital pass 2804 is substantially the same as the digital pass 2800 of FIG. 28A, but displays additional information, such as, for example, the result of the test, the date of the test, and the type of test that used. Therefore, the digital pass 2800, 2804 is an interface that is generated by the code generator 212 of the user application 116. In some examples, the digital pass 2800, 2804 is re-regenerated each time the user 102 opens the digital pass 2800, 2804. The digital pass 2800, 2804 can include the user identification (e.g., the user's name, the user account ID, etc.) and an indicator. The indicator can include the digital pass code 2802, 2806, the test result, the date of the test, and/or the expiration date, as shown in FIGS. 28A and 28B. The indicator is generated in response to the result begin negative and the number of days (or time) since the diagnostic test being below a threshold number of numbers (or threshold time). Therefore, the indicator is indicative of the health status of the user 102.

As disclosed above, in some examples, the code generator 212 may create additional digital passes (e.g., for the same infectious disease and/or other infectious diseases). In some examples, a single digital pass may include information related to a number of tests infectious disease and/or other infectious diseases.

When the user 102 decides to enter the location monitored by the verifier 106, the user 102 displays the digital pass 2800 on the user device 108 to the verifier 106. For example, if the verifier 106 is an airline, the user 102 may display the digital pass 2800 to a gate agent before boarding the plane. As another example, if the verifier 106 is an office (e.g., the user's place of employment), the user 102 can display the digital pass 2800 to a person (e.g., a security officer or representative of the employer) in the lobby of the office. In some examples, the user application 116 on the user device 108 may send the digital pass 2800 to another device to be displayed. For example, if the user has a smartwatch with a display screen, the transceiver 204 may transmit the digital pass 2800 to the user's smartwatch to be displayed.

Figure 29:
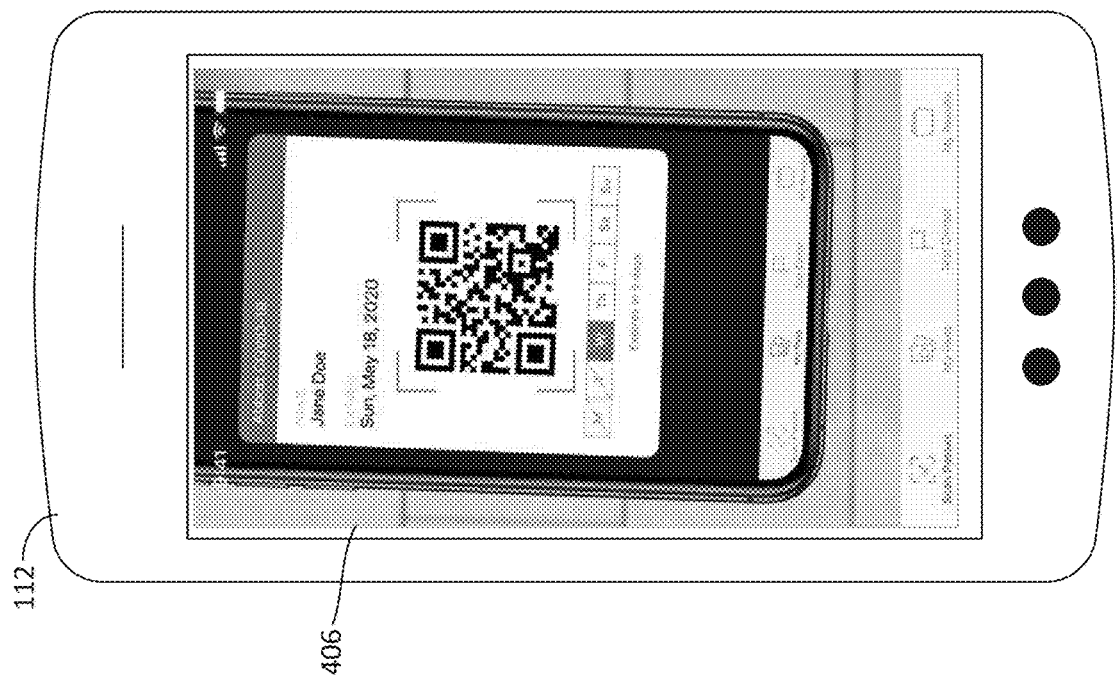

The verifier 106 uses the camera 408 of the verifier device 112 to read or scan the digital pass code 2802 on the user device 108. For example, FIG. 29 shows the display 406 on the verifier device 112, which is displaying the view from the camera 408. Additionally or alternatively, the verifier 106 can use another device to scan the digital pass code 2082, such as a mounted or a handheld scanner (e.g., a QR code or barcode scanner) communicatively coupled to the verifier device 112. The detector 410 of the verifier application 120 detects the digital pass code 2802. The certifier 412 interprets the digital pass code 2802 and obtains the user account ID and the test kit ID (and/or other identifying information) embedded in the digital pass code 2802. The certifier 312 sends (e.g., via the transceiver 404) the user account ID and test kit ID to the digital pass management system 100.

The validator 506 of the digital pass management system 100 inspects the records to determine whether the user account ID and test kit ID match the user account and are still valid (e.g., not expired and still associated with the verifier organization). For example, the validator 506 may verify the result of the diagnostic test based on the user account ID and the test kit ID. In other words, the validator 506 may match user account ID and the test kit ID to the result of the diagnostic test. The validator 506 may also determine the number of days since the diagnostic test and compare the number of days since the diagnostic test to a threshold number of days. The validator 506 may transmit a verification outcome (indicating whether the digital pass 2800 is valid, invalid, or not found) based on the verification of the result and the number of days. For example, if the diagnostic test result is negative and the number of days since the diagnostic test satisfies (e.g., is below) the threshold number of days, the validator 506 transmits a first notice, notification, or message indicating the digital pass 2800 is valid.

If the number of days since the diagnostic since does not satisfy (e.g., is greater than) the threshold number of days, the validator 506 transmits a second notice, notification, or message indicating the digital pass 2800 is expired or not valid. In some examples, the validator 506 may also transmit the second notice, notification, or message if the user account ID has been inactivated or removed from a verifier organization associated with the verifier 106 (e.g., if an employee no longer works with the employer) or another reason. Additionally or alternatively, the validator 506 may transmit the second notice, notification, or message if the test result was positive or inconclusive. This helps prevent against fraudulent generation of a digital pass. If validator

506 could not find a diagnostic test associated/matched with the user account ID and/or the test kit ID, the validator 506 transmits a third notice, notification, or message indicating the digital pass 2800 is not found. In some examples, if the result was inconclusive (e.g., the sample was contaminated or an insufficient amount of sample was gathered to effectively conduct the diagnostic test), the validator 506 transmits a fourth notice, notification, or message indicating the result was inconclusive.

In some examples, in addition to or as an alternative to using the number of days to determine if the digital pass 2800 has expired, the validator 506 may use an amount of time (e.g., 30 hours). For example, the validator 506 may determine an amount of time between performance of the diagnostic test and receipt of the user account ID and test kit ID from the verifier device 112. When the amount of time satisfies (e.g., is below) a threshold amount of time, for example, the validator 506 may transmit the first notice, notification, or message disclosed above to indicate the digital pass 2800 is still valid. When the amount of time does not satisfy (e.g., is greater) than the threshold amount of time, for example, the validator 506 may transmit the second notice, notification, or message disclosed above to indicate the digital pass 2800 is expired or not valid.

In some examples, the threshold number of days and/or threshold amount of time is set by the verifier organization. Additionally or alternatively, the threshold number of days and/or the threshold amount of time may be based on a biological characteristic of the analyte of interest, such as an incubation period of the pathogen and/or a contagious period of the pathogen.

Figure 30:
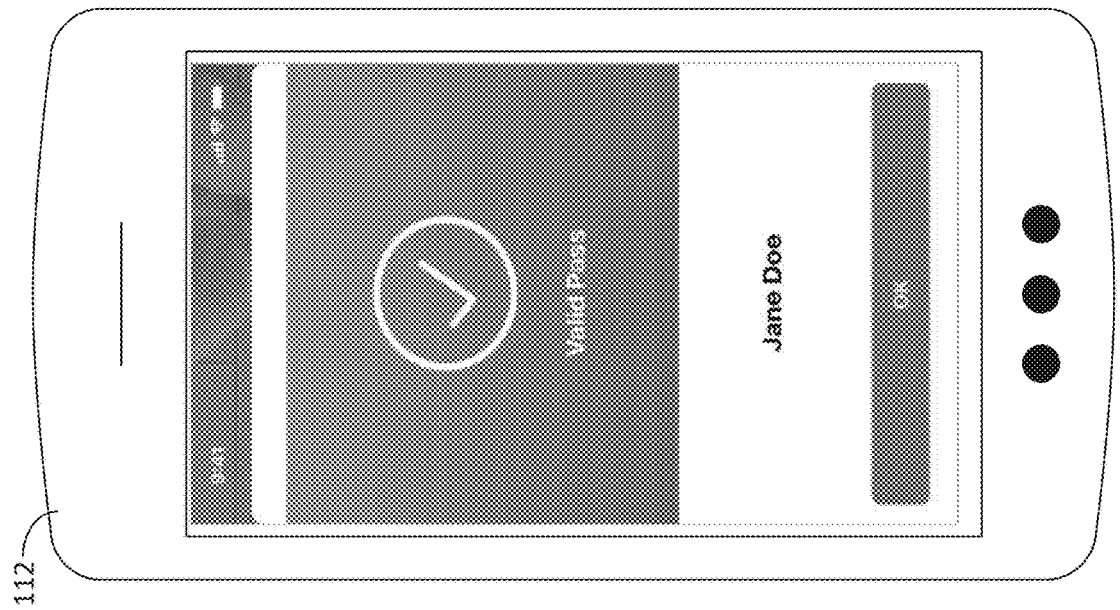
FIGS. 29-32 are example user interface screens that may be displayed on the example verifier device of FIG. 4 by the example verification application.
Figure 31:
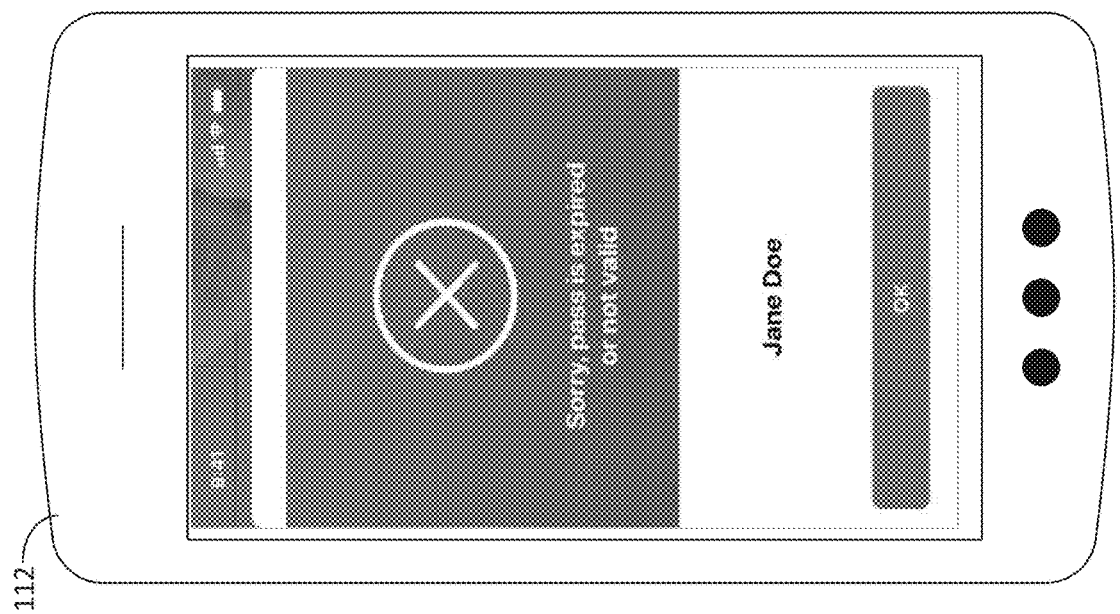
Figure 34:
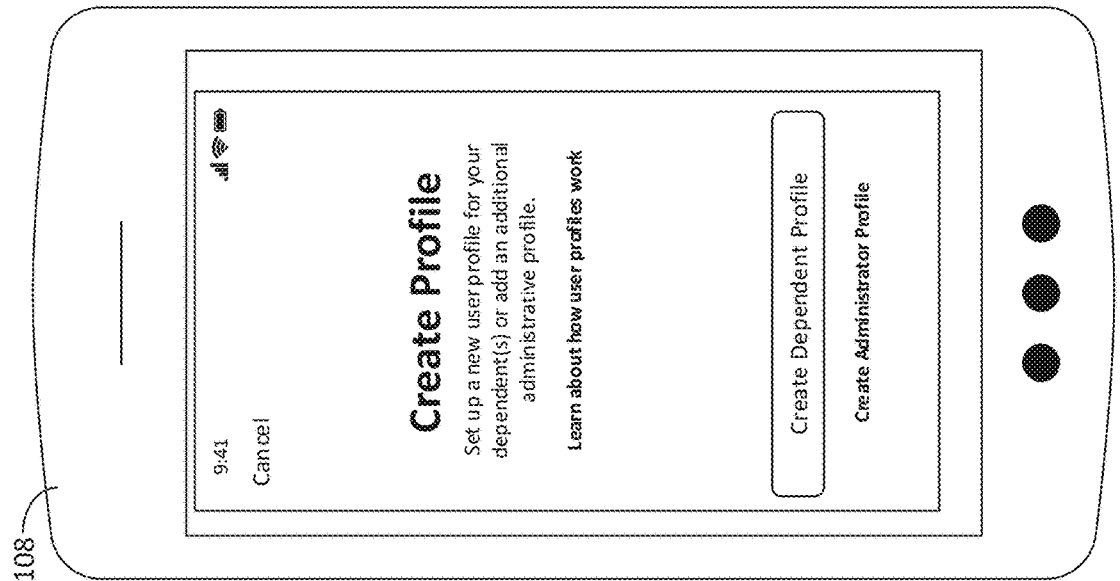
FIGS. 33-38 are example interface screens that may be displayed on the example user device of FIG. 2 by the example user application.

If the digital pass 2800 is valid, the notifier 414 of the verifier application 120 displays a positive or an acceptance message (e.g., a first notice), such as, for example, the valid message shown in FIG. 30. The acceptance message confirms that the user 102 has recently tested negative for the infectious disease or analyte of interest and can be allowed access to the location. If the certifier 412 determines that the digital pass 2800 is expired or invalid, the notifier 414 of the verifier application 120 can display a negative or denial message (e.g., a second notice), such as, for example, the message shown in FIG. 31 indicating that the pass is expired or not valid. As such, the verifier 106 can deny the user 102 access to the location. In some examples, if the result of the test was inconclusive, the notifier 414 can display the same interface as shown in FIG. 31 or another interface/display indicating the result was inconclusive. In such an instance, the verifier 106 can decide whether to allow or deny access to the user 102. If a digital pass is not found, the notifier 414 of the verifier application 120 can display another message (e.g., a third notice), such as, for example, the message shown in FIG. 32 indicating that a pass is not found. In such an instance, the verifier 106 can deny the user 102 access. Therefore, the verifier application 120 can display the first notice (FIG. 30), the second notice (FIG. 31), the third notice (FIG. 32), and/or any other notices to grant or deny the user 102 access to the location based on the verification outcome and a location of the verifier device 112.

In some examples, instead of or in addition to the validator 506 checking whether the digital pass has expired, the digital pass management system 100 confirms the result was negative and then sends the date of the diagnostic test to the verifier device 112. Then, the verifier application 120 compares the number of days or amount of time since the diagnostic test to a threshold number of days or amount of time. Depending on the outcome, the verification application 120 can present one of the interfaces shown in FIGS. 30-32.

In some examples, this enables the verifier 106 to set their own preferred expiration threshold through the verifier application 120 and without reliance on the validator 506 to maintain and/or verify expiration dates.

In some examples, different verifiers can have different expiration times or thresholds. For example, a first verifier may have a first expiration threshold of seven days and a second verifier may have a second expiration threshold of five days. These expiration thresholds can be saved with the digital pass management system 100 and/or in their corresponding verification applications. When the digital pass 2800 is scanned by the first verifier, the number of days or time since the diagnostic test is compared to the first expiration threshold, and when the digital pass 2800 is scanned by the second verifier, the number of days or time since the diagnostic test is compared to the second expiration threshold. This enables verifier organizations to set their preferred expiration thresholds.

In addition to or as an alternative to displaying the verification outcome on the verifier device 112, the verifier device 112 can automatically unlock at least one of a door, a gate, or a turnstile based on the verification outcome. For example, the user 102 may present his/her digital pass 2800 to the verification device 112 (e.g., a scanner at a gate) at a gate of a location managed by the verification organization. If the digital pass 2800 is valid, the verification application 120 can unlock the gate to enable the user 102 to access the location. If not, the verification application 120 enables the gate to remain locked to deny the user 102 access to the location.

As disclosed above, the user application 116 can be used to manage multiple digital passes for the user 102. Each digital pass can be generated using the example digital pass verification process disclosed above. The digital passes can be associated with diagnostic tests for the same or different analyte of interest. Each diagnostic test may be used to detect a presence or an absence of a certain analyte of interest. For example, the user application 116 may store a first digital pass with a first digital pass code associated with a first diagnostic test for a first analyte of interest (e.g., COVID-19) and a second digital pass with a second digital pass code associated with a second diagnostic test for a second analyte of interest (e.g., influenza), which may be the same or different than the first analyte of interest.

In some examples, when a digital pass expires, the user 102 can get re-tested for the same analyte of interest to generate a new digital pass for that analyte of interest. In some examples, the second or subsequent diagnostic test may be a different type of test than the first diagnostic test. For example, the first diagnostic test may be an antigen test and the second diagnostic test may be an antibody test. In other examples, other types of tests may be used, such as polymerase chain reaction (PCR)/molecular tests, antigen tests, etc. In some examples, the first diagnostic test is performed with a first type of testing equipment (e.g., a disposable test kit) and the second diagnostic test is performed with a second type of testing equipment (e.g., a laboratory analyzer device) that is different than the first type of testing equipment.

The digital passes can be read by different verifier organizations. For example, a first digital pass can be read by a first verifier device of a first verifier (e.g., a school) when the user 102 desires to enter a location managed by the first verifier, and a second digital pass can be read by a second verifier device of a second verifier (e.g., an employer) when the user 102 desires to enter a location managed by the second verifier.

In some examples, the user 102 can use the user application 116 to manage digital passes associated with multiple verifier organizations or entities. For example, various organizations or entities may require a digital pass for access, such as the user's place of employment, the user's school, an airline, etc. The user 102 can use the user application 116 to add organizations to and/or remove organizations from the user's account. The user application 116 may store (e.g., in a digital wallet) the digital passes for the user 102 associated with the various organizations.

In some examples, the digital pass management system 100 stores information associated with each scan of a digital pass such as the time/date, the person who scanned the pass, the location, the result of the scan (e.g., valid, invalid) etc. This may help prevent fraudulent use of the digital pass (e.g., if a second user attempts to use the same digital pass in a different location at the same time).

In some examples, in addition to the expiration date of the digital pass 2800, other constraints can be placed on a valid digital pass. For example, the organization associated with the verifier 106 may desire to prevent or prohibit access to the verifier location on certain days and/or to allow or prevent access to specific buildings or areas of buildings controlled by the organization. In some examples, the organization may set limits such that the digital pass 2800 is only valid on certain days, within certain time ranges, and/or to certain locations including, for example, specific turnstiles, elevators, doors, etc. For example, the user's employer may desire to only allow certain employees on the premises on certain days of the week to stagger the employees to reduce likelihood of virus transmission. In such an example, the digital pass 2800 may be invalid on certain days of the week, which prevents the user 102 from gaining access to the office on those days. These specific days and/or time ranges can be set by the verifier 106 (e.g., via the verification application 120) and saved with the user's account in the database 502 and/or on the user application 116 with the digital pass 2800. Therefore, the verifier application 120 can display different notices including, for example, the first notice (FIG. 30), the second notice (FIG. 31), or the third notice (FIG. 32) to grant or deny the user 102 access to the location based on the verification outcome and at least one of a time of day or a day of the week.

In some examples, a verifier organization, such as an employer, can deactivate a user's digital pass in the digital pass management system 100 when the user leaves the company (e.g., is fired or voluntarily quits). Then, if the digital pass code 2802 is scanned, the validator 506 invalidates the digital pass code 2802 even when the number of days since the diagnostic test is below the threshold number of days. In such an instance, the validator 506 transmits an invalid message to the verifier device 112. Therefore, the verifier application 120 can display the first notice (FIG. 30), the second notice (FIG. 31), or the third notice (FIG. 32) based at least in part on an employment status of the user 102.

In some examples, after the user 102 has received a digital pass, the user application 116 may require the user 102 to answer a daily health questionnaire to ensure the user 102 has not become sick. For example, the analyzer 216 may cause the user application 116 to display a list of health questions to check whether the user has had any recent symptoms (e.g., "Have you had a temperature over 103° F. in the last 24 hours?", "Have you developed a cough in the last 24 hours?", etc.). In some examples, based on the user 102 answers to one or more of the questions, the analyzer 216 deactivates the digital pass 2800 (e.g., prevents the digital pass 2800 from being displayed), which prevents the user 102 from gaining access to the verifier location. If later (e.g., the next day) the user 102 answers the questions differently, the analyzer 216 may re-activate the digital pass such as, for example, when the user 102 no longer displays symptoms of an illness. In some examples, depending on the answers to the health questions, the analyzer 216 may recommend that a user 102 take a test or, in some situations, that a user does not take a test.

In some examples, each time the user 102 accesses (e.g., opens) the user application 116, the user 102 is required to log in with their account name and password. In some example, the user application 116 may use one or more biometrics of the user 102 to grant access (e.g., via facial recognition using the camera 207, via a thumb print scan, etc.). In some examples, the user application 116 requires multi-factor authentication (MFA). In some such examples, the MFA is associated with the user's phone number, which may be stored with the user's account in the database 502.

In some examples, testers or testing facilities can create accounts with the digital pass management system 100. This enables users to search for testers or testing facilities near the users. In some examples, certain ones of the tester or testing facilities may be registered or approved by certain verifier organizations.

In some examples, the user application 116 can be used to manage one or more profile(s)/account(s) and/or digital pass(es) associated with other persons related to or associated with the user 102. For example, the user 102 may be able create and access user accounts(s) and/or digital pass(es) for younger dependents (e.g., people under the age of 18), such as the user's children, and/or older dependents, such as the user's parents or grandparents, via the user application 116. The user application 116 may enable the user 102 to add dependents, remove dependents, edit dependent account information, etc. The dependent's account ID may be linked to the user's account ID in the digital pass management system 100. The user application 116 may also store all current and/or prior test results and digital passes associated with the dependents. The user 102 can view all prior tests and present digital passes associated with the dependents via the user application 116, similar to the tests and digital passes associated with the user 102 as disclosed herein. The user 102 can use the user application 116 to present the dependent's digital passes to certain verifiers to enable access. For example, the user 102 may use the user application 116 to manage a digital pass associated with the user's child. In such an example, the user 102 may use the user application 116 to present a digital pass for the child to a certain verifier, such as a school when dropping the child off at school or to an airline when boarding an airplane.

Figure 33:
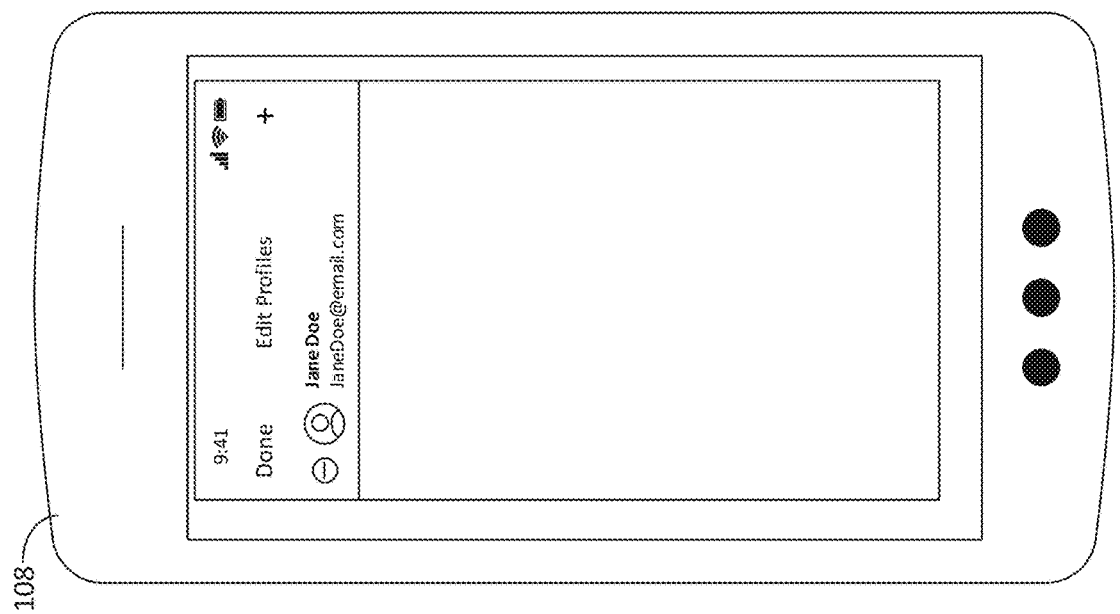
Figure 35:
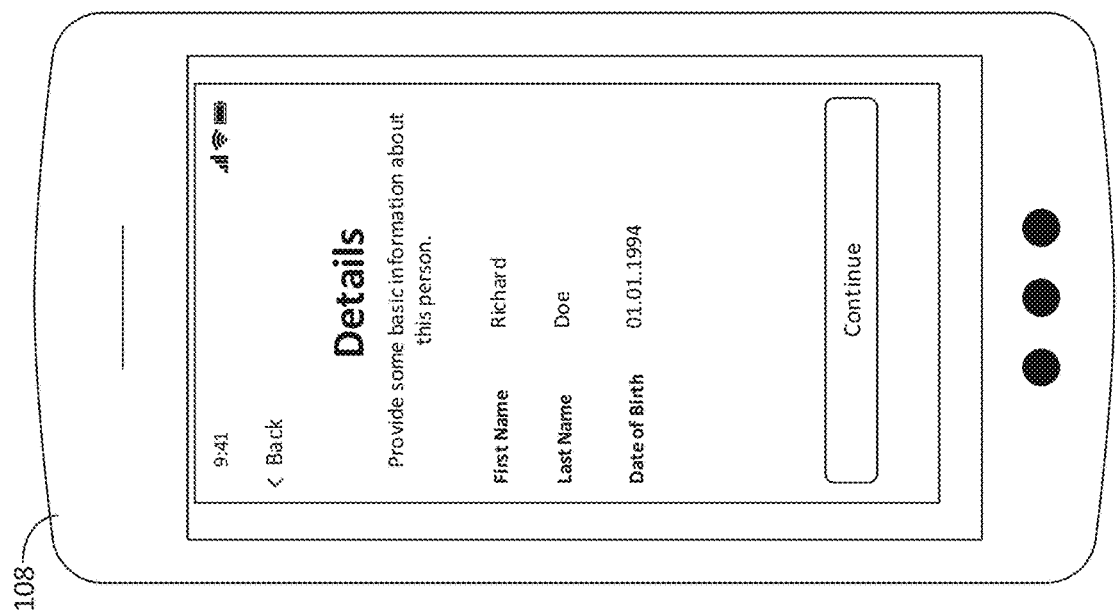

For example, FIG. 33 shows an example interface that may be presented by the user application 116 on the user device 108. The interface shows a list of all profiles or accounts stored and associated with the user's account. The user 102 can select to add an additional profile, such as a profile for a dependent (such as, for example, selecting the '+' symbol shown in FIG. 33). After selecting to add a new profile, the user application 116 presents the interface shown in FIG. 34. The user 102 can select to create, for example, a dependent profile or an administrator profile, such as for example, a person who manages multiple user accounts. The user 102 can select to create a dependent profile. FIG. 35 shows an interface presented by the user application 116 where the user 102 can enter information (e.g., the dependent's name, birthday, address, etc.) to create a dependent account. The user application 116 transmits (e.g., via the transceiver 204) the dependent account information to the digital pass management system 100, which is then stored in the database 502 with the user's account (e.g., in the data entry 510). The user 102 can then have access to the dependent's account and utilize the dependent's account similar to the user's own account as disclosed herein.

As disclosed above, the user 102 can connect or register himself/herself and/or one or more dependents to one or more verifier organization accounts in the digital pass management system 100. This enables the verifier organizations to have access to the user's account information and/or dependent account information. The verifier organization can control certain parameters (e.g., expiration time) associated with the user's digital passes for the verifier organization. The user 102 can connect with an organization via the user application 116. For example, FIG. 36 shows an interface presented by the user application 116 on the user device 108 where the user 102 can enter a code or ID to connect with an organization. The code can be provided via an invite message (e.g., via email or text) from the verifier organization. The user application 116 obtains the identity of the organization from digital pass management system 100 and presents the organization information to the user 102 for confirmation, as shown in FIG. 37. The user 102 can select to add the connection, as shown in FIG. 38. In this example, the profile for a dependent is linked to the organization. The same process can be used to register the user's own account with the verifier organization.

Figure 39:
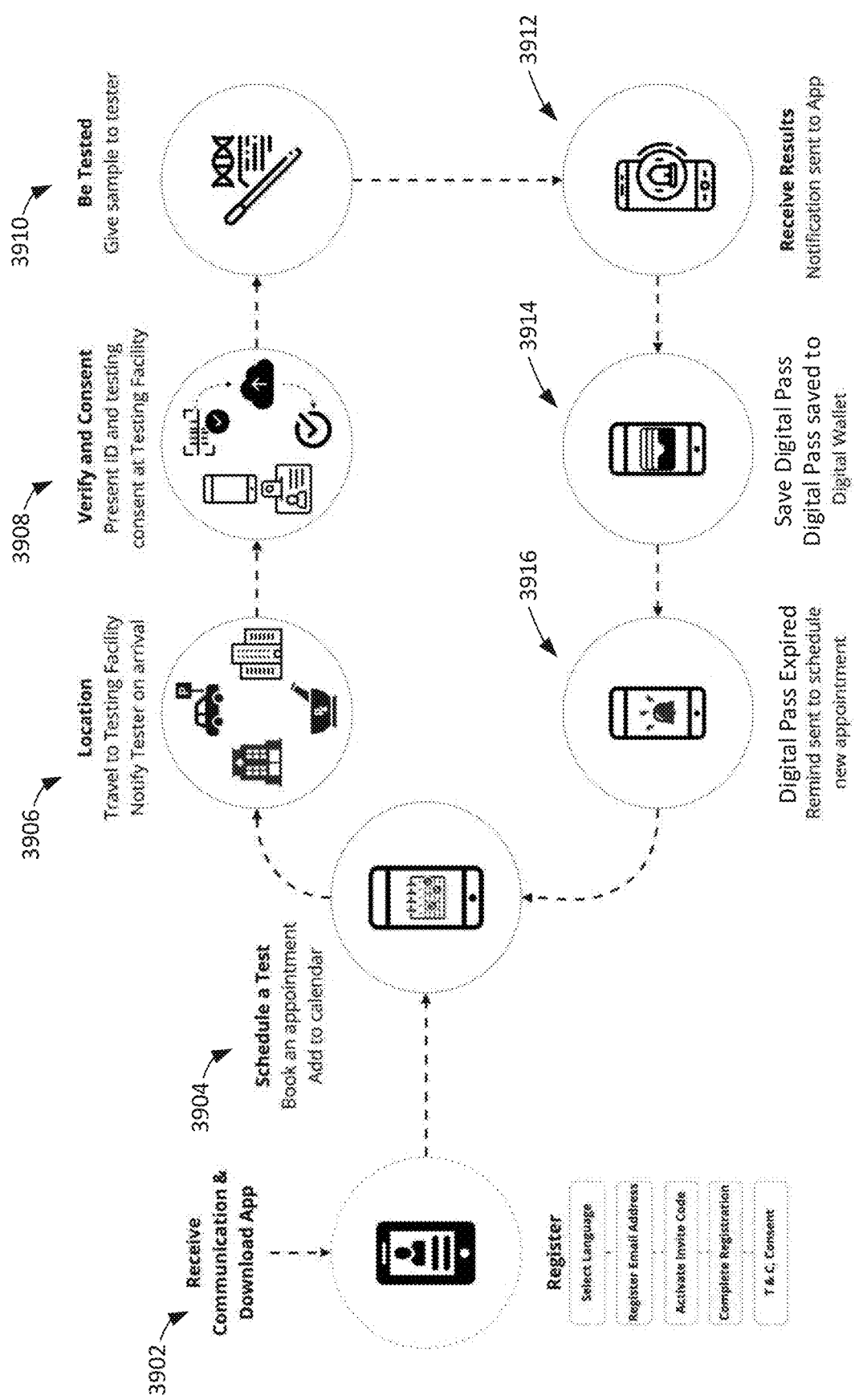
FIG. 39 is an example timeline or sequence of events as performed by and/or experienced by a user during an example digital pass verification process.

FIG. 39 shows an example timeline or sequence of events as performed and/or experienced by a user, such as the user 102, during a digital pass verification process. The example events can be performed in any other order and any of the events can be removed, replaced, and/or repeated.

At step 3902, the user 102 downloads the user application 116 onto the user device 108 and registers with the digital pass management system 100. In some examples, the user device 108 initially receives a communication (e.g., a text, an email, etc.) to download the user application 116. For example, the verifier 106 may send communications to users (e.g., employees, future passengers, etc.) that intend to access the verifier location(s). At step 3904, the user 102 schedules a test. In some examples, the user 102 schedules the test via the user application 116. In such an example, the scheduler 208 books an appointment with a testing facility. In some examples, the notifier 210 provides alerts or reminders about the upcoming appointment.

At step 3906, the user 102 travels to the testing facility and notifies the tester 104. At step 3908, the user 102 provides their identification and consent for the test. For example, the code generator 212 may generate the identity code 1200 (as shown in FIG. 12) on the user device 108, which is then scanned by the tester device 110. In some examples, the user 102 also shows his/her physical ID (e.g., a driver's license) to the tester 104. At step 3910, a sample (e.g., a nasal swab, a urine sample, a blood sample, etc.) is taken from the user 102 and given to the tester 104, and the tester 104 performs the test.

At step 3912, the user device 108 receives the results and the user 102 can review the results on the user device 108. In some examples, the notifier 210 provides an indication (e.g., a push notification) that the results have been received. At step 3914, if the results are negative, the code generator 212 generates the digital pass 2800 and the digital pass code 2082 and saves the digital pass 2800 to a digital wallet on the user device 108. In some examples, the code generator 212 creates an expiration date associated with the digital pass 2800. The user 102 can then use the digital pass 2800 until the digital pass 2800 has expired.

At step 3916, the time comparator 214 and scheduler 208 determines whether the digital pass 2800 has expired (e.g., by comparing the current date to the expiration date of the digital pass 2800). If the digital pass 2800 has expired, the notifier 210 may provide an alert to remind the user 102 to get tested again, and the example cycle may be repeated.

Figure 40A:
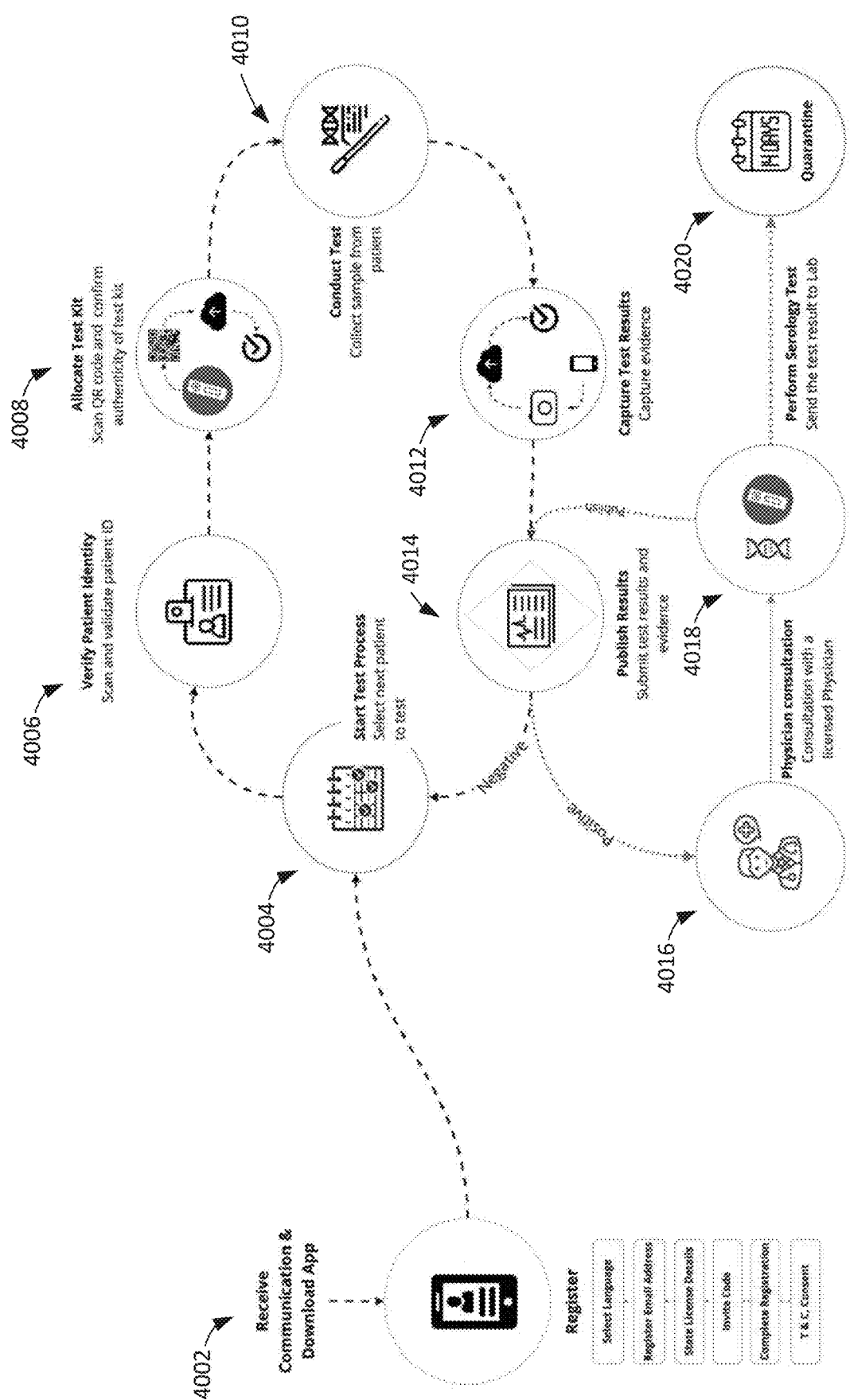
FIG. 40A is an example timeline or sequence of events as performed by and/or experienced by a tester during an example digital pass verification process.

FIG. 40A shows an example timeline or sequence of events as performed and/or experienced by a tester, such as the tester 104, during a digital pass verification process. The example events can be performed in any other order and any of the events can be removed, replaced, and/or repeated.

At step 4002, the tester 104 downloads the tester application 118 onto the tester device 110 and registers with the digital pass management system 100. In some examples, the tester device 110 initially receives a communication (e.g., a text, an email, etc.) to download the tester application 118. At step 4004, the tester 104 starts the test process by selecting the next patient. At step 4006, the tester 104 verifies the patient identity and creates a test record. For example, the reader 318 can detect and interpret the identity code 1200 on the user device 108. The record generator 310 creates a record for the test and may send the user information to the digital pass management system 100 to store with the user account.

At step 4008, the tester 104 selects a test kit or test cartridge to be used. In some examples, the test kit selector 312 determines which test kit or test cartridge should be used. The tester 104 can use the tester device 110 to scan a test kit code on the test kit. The reader 318 detects and interprets the test kit code on the test kit to obtain the test kit ID. The tester application 118 and/or the digital pass management system 100 can verify the authenticity of the test kit (e.g., to ensure the test kit has not been used before, is manufactured by a list of approved manufacturers, has not expired, etc.). The record generator 310 can save the test kit code and/or send the test kit code to the digital pass management system 100 to be saved with the user's account.

At step 4010, the tester 104 collects a sample from the user 102 and performs the test. At step 4012, the tester 104 captures the test results. In some examples, the tester 104 enters the results into the tester application 118 (e.g., by selecting one of a plurality of predefined options). In some examples, the tester 104 uses the tester device 110 to take a picture of at least a portion of the used test kit as evidence. At step 4014, the record generator 310 saves and publishes the results (e.g., sends the results to the user device 108). In some examples, the record generator 310 sends the results and/or the picture(s) to the digital pass management system 100, which sends the results to the user device 108. In some examples, in addition to viewing the results, the user 102 can view the picture of the test kit via the user application 116. In some examples, the user application 116 saves and presents all historical pictures of the test kits associated with the user 102.

If the results are negative, the example cycle can be repeated when the user 102 comes back to get retested again (e.g., after expiration of the digital pass) or an additional test could be ordered and performed to determine a presence of another analyte of interest, confirm results of an initial test or determine possible immunity. If the results are positive, the tester 104 may recommend the user 102 has a consultation with a licensed physician, at step 4016. At step 4018, additional testing may be performed to verify the results. In some examples, a serology test is performed and the test results are sent to a lab. In some examples, the user 102 is quarantined (e.g., via self-quarantining, quarantined in a medical facility, etc.) for a period of time, as step 4020.

Figure 40B:
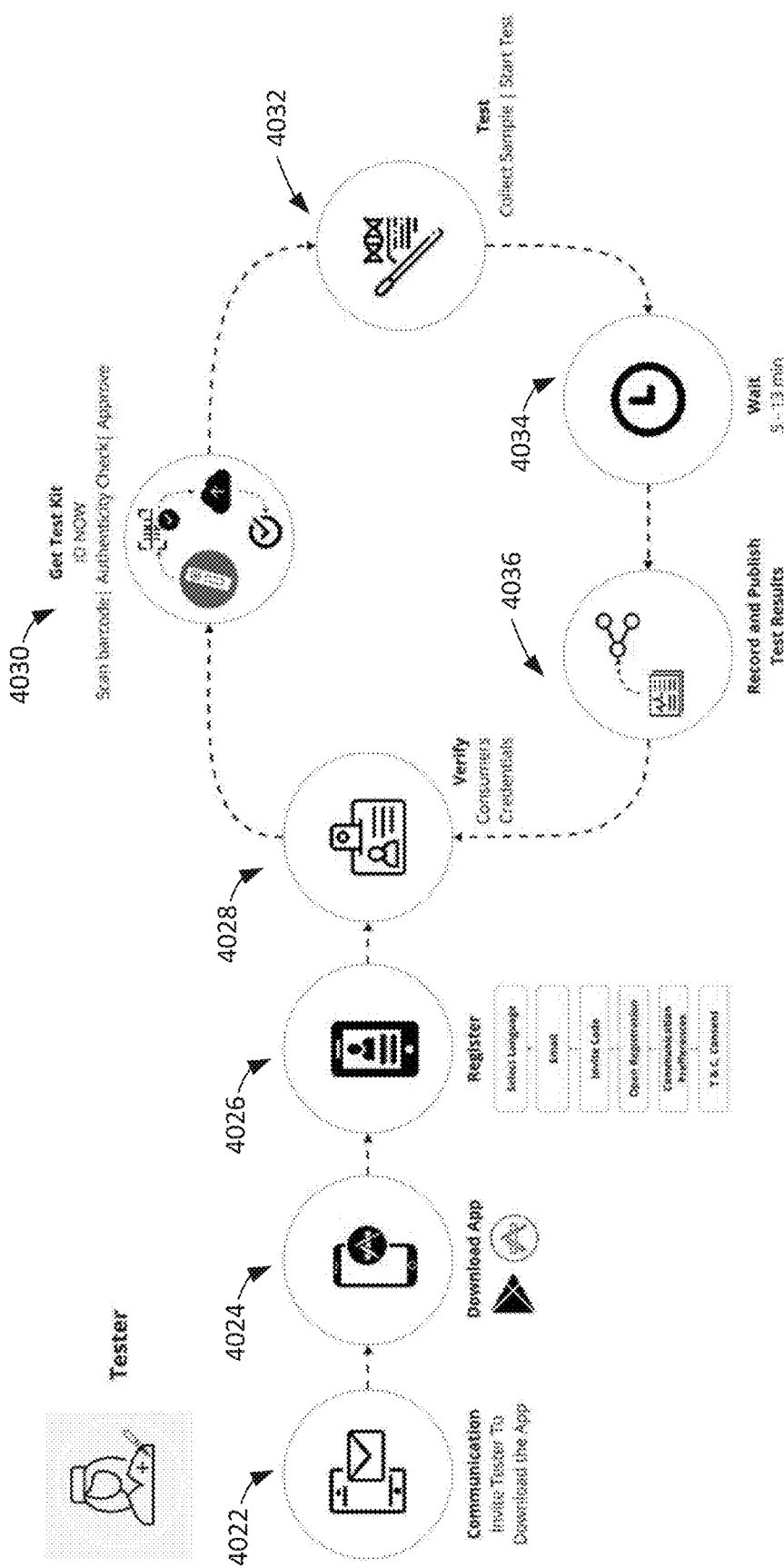
FIG. 40B is another example timeline or sequence of events as performed by and/or experienced by a tester during an example digital pass verification process.

FIG. 40B shows an example timeline or sequence of events as performed and/or experienced by a tester, such as the tester 104, during a digital pass verification process. In this example, a laboratory analyzer device, such as the Abbott Laboratories' ID NOW™ analyzer is used for testing. The example events can be performed in any other order and any of the events can be removed, replaced, and/or repeated.

Similar to the timeline or sequence of events in FIG. 40A, the tester device 110 receives a communication (e.g., an invite) to download the tester application 118 (step 4022), and the tester 104 downloads the tester application 118 (step 4024) and registers with the digital pass management system 100 (step 4026).

At step 4028, the tester 104 verifies the patient identity and creates a test record. For example, the reader 318 can detect and interpret the identity code 1200 on the user device 108. The record generator 310 creates a record for the test and may send the user information to the digital pass management system 100 to store with the user account.

At step 4030, the tester 104 selects a test cartridge to be used in the ID NOW™ analyzer. The tester 104 can use the tester device 110 to scan a test kit code on the test cartridge. The reader 318 detects and interprets the test kit code on the test cartridge to obtain the test kit ID. The tester application 118 and/or the digital pass management system 100 can verify the authenticity of the test cartridge (e.g., to ensure the test cartridge has not been used before, is manufactured by a list of approved manufactures, has not expired, etc.). The record generator 310 can save the test kit code and/or send the test kit code to the digital pass management system 100 to be saved with the user's account.

At step 4032, the tester 104 collects a sample from the user 102 and performs the test. At step 4034, the tester 104 for the test to be completed. In some examples, the ID NOW™ analyzer has a digital screen that displays the results of the test. At step 4036, the tester 104 records and publishes the results. In some examples, the tester 104 enters the results into the tester application 118 (e.g., by selecting one of a plurality of predefined options). In some examples, the tester 104 uses the tester device 110 to take a picture of the digital screen as evidence. The record generator 310 saves and publishes the results (e.g., sends the results to the user device 108). In some examples, the record generator 310 sends the results and/or the picture(s) to the digital pass management system 100, which sends the results to the user device 108. The example cycle can then be repeated with the next patient.

Figure 41:
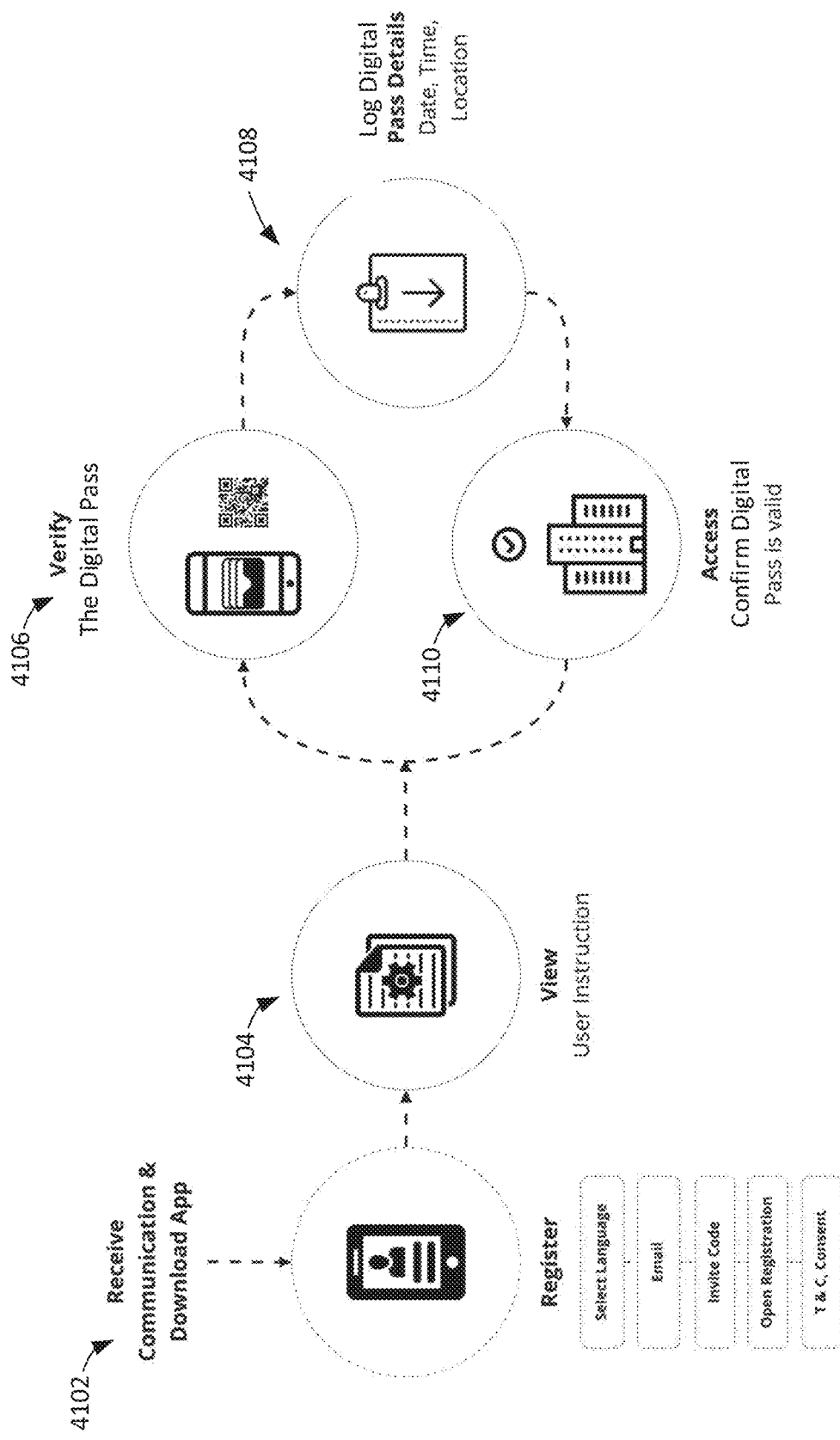
FIG. 41 is an example timeline or sequence of events as performed by and/or experienced by a verifier during an example digital pass verification process.

FIG. 41 shows an example timeline or sequence of events as performed and/or experienced by a verifier, such as the verifier 106, during a digital pass verification process. The example events can be performed in any other order and any of the events can be removed, replaced, and/or repeated.

At step 4102, the verifier 106 downloads the verifier application 120 onto the verifier device 112 and registers with the digital pass management system 100. In some examples, the verifier device 112 initially receives a communication (e.g., a text, an email, etc.) to download the verifier application 120. At step 4104, the verifier application 120 can display instructions on the verifier device 112 for how to use the verification application 120.

At step 4106, the verifier 106 uses the verifier device 112 to scan the digital pass code 2802 on the user device 108. The detector 410 detects the digital pass code 2802 and the certifier 412 interprets the digital pass code 2802 to obtain identifying information (e.g., the user account ID and test kit ID) embedded in the digital pass code 2802. The verifier application 120 records the digital pass details (e.g., date, time, location) and/or sends the details to the digital pass management system 100 to be saved with the user account (step 4108). If the pass is valid, the verifier 106 can grant the user 102 access to the location (step 4110). If not, the verifier 106 can deny the user 102 access to the location.

Figure 42A:
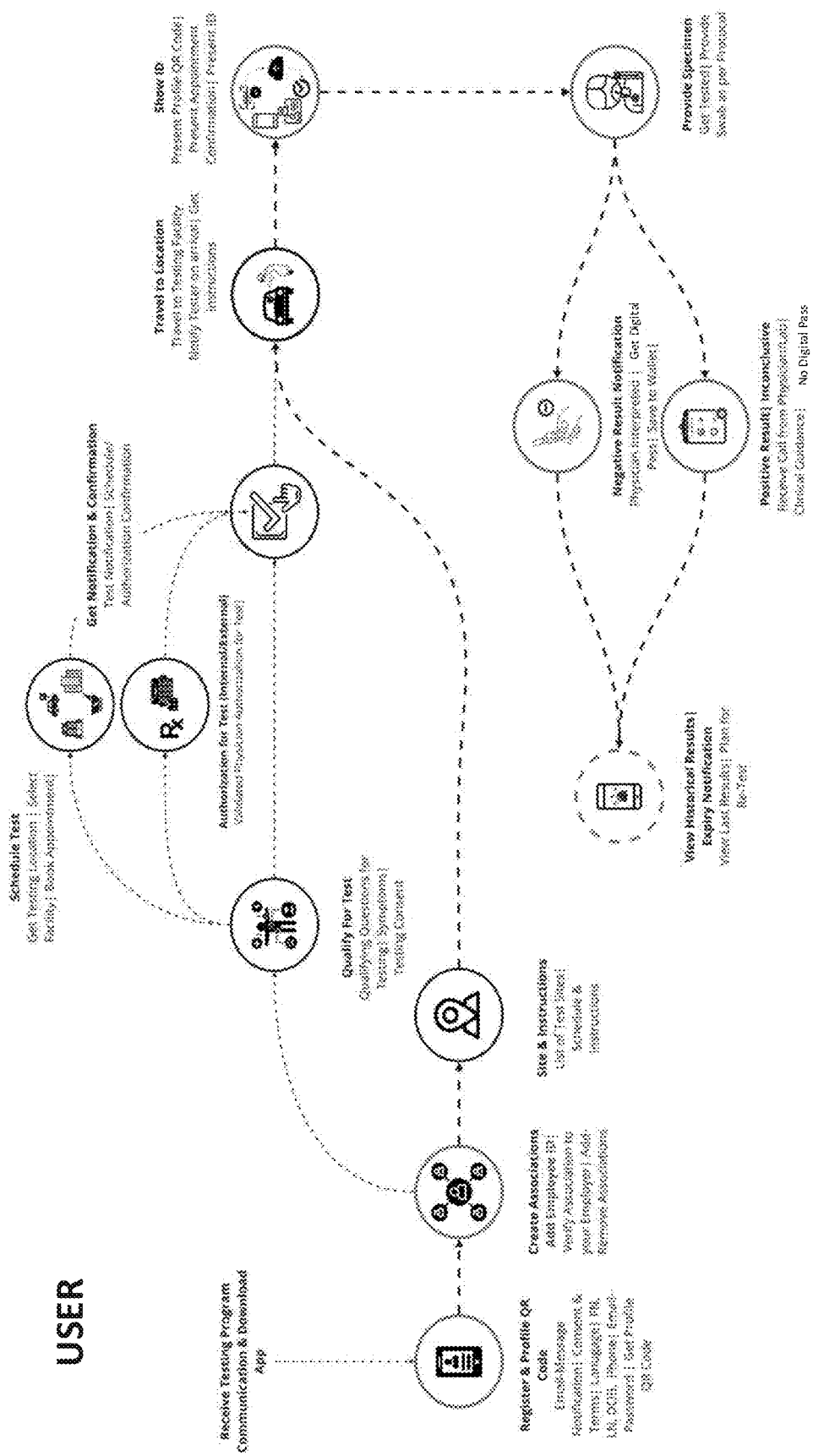
FIGS. 42A, 42B, and 42C are example timelines or sequences of events as performed and/or experienced by a user, a tester, and a verifier, respectively during an example digital pass verification process where an employer is the verifier and an employee is the user.
Figure 42B:
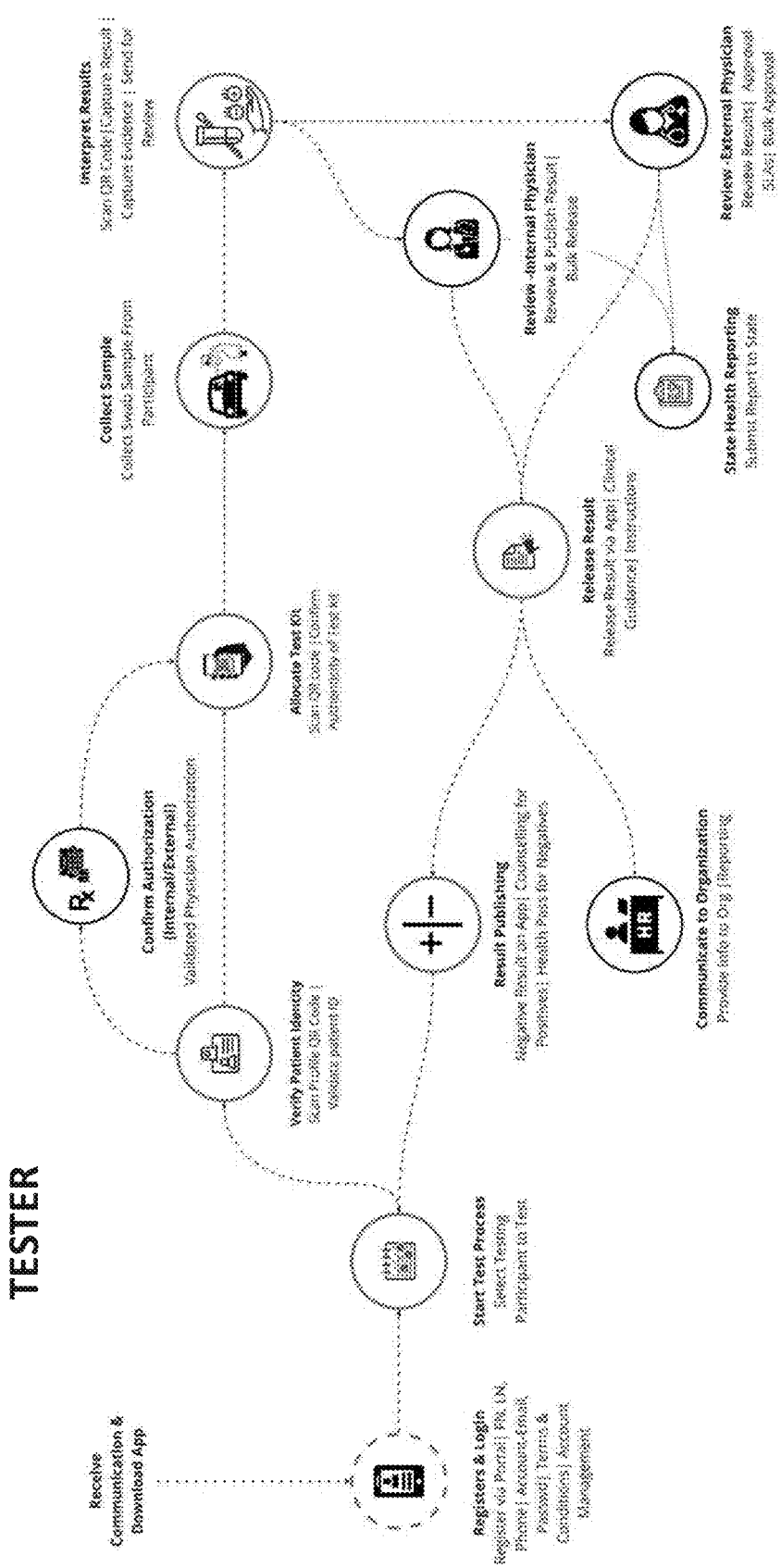
Figure 42C:
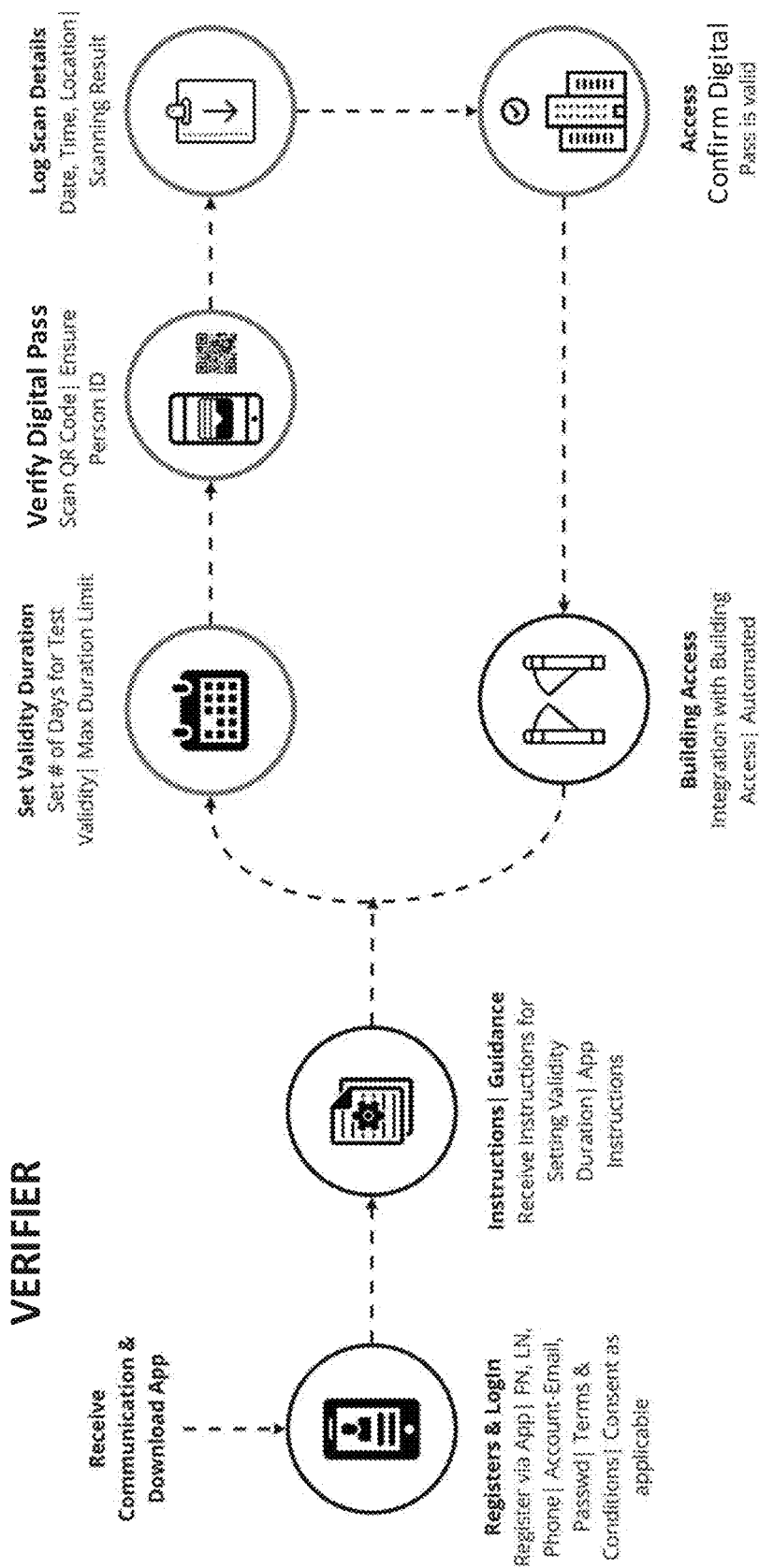

FIGS. 42A, 42B, and 42C show example timelines or sequences of events as performed and/or experienced by a user, a tester, and a verifier, respectively, in connection with a digital pass verification process implemented in connection with an employer as the verifier. The employer (verifier) can use the digital pass verification techniques disclosed herein to confirm the employees (users) have recently tested negative for an infectious disease before allowing the employees to enter the workplace facilities. The example events can be performed in any other order and any of the events can be removed, replaced, and/or repeated.

The timeline in FIG. 42A is similar to the timeline in FIG. 39 for the user 102. However, in this example, when creating the user account, the user 102 can add his/her employee ID information to verify association with a specific employer. The employee ID information can be saved with the user account in the database 502. The user 102 may be prompted to enter additional information and/or answer questions related to the user's recent experiences including, for example, questions about travel, symptoms (e.g., current body temperature), proximity to infected or symptomatic people, etc. The information and/or answers to the questions may be analyzed to determine if the user 102 qualifies to be tested or re-tested. The user 102 may be tested by an internal physician associated with the employer (e.g., an onsite testing department) or an external physician not associated with the employer. In some examples, the employer can authorize or validate requests for tests via external physicians.

The timeline in FIG. 42B is similar to the timelines in FIGS. 40A and 40B for the tester 104. However, in this example, the tester 104 may be an internal physician associated with the employer. In other examples, as shown in FIG. 42B, the user 102 can be tested by an external physician. In some examples the results are communicated to the employer. For example, the tester application 118 and/or the digital pass management system 100 can transmit the test results to the employer (the verifier). In some examples, the results are submitted to the state or other government agency.

The timeline in FIG. 42C is similar to the timeline in FIG. 41 for the verifier 106. In this example, the employer (the verifier) can set the number of days until a digital pass expires. In some examples, the verifier application 120 records the date, time, and location when digital passes are scanned. In some examples, the verifier 106 may be an automated machine. For example, the user 102 may scan his/her digital pass code at a security gate. If the digital pass is valid, the gate automatically opens to allow entry. Thus, in some examples, no human interaction is needed.

Figure 43:
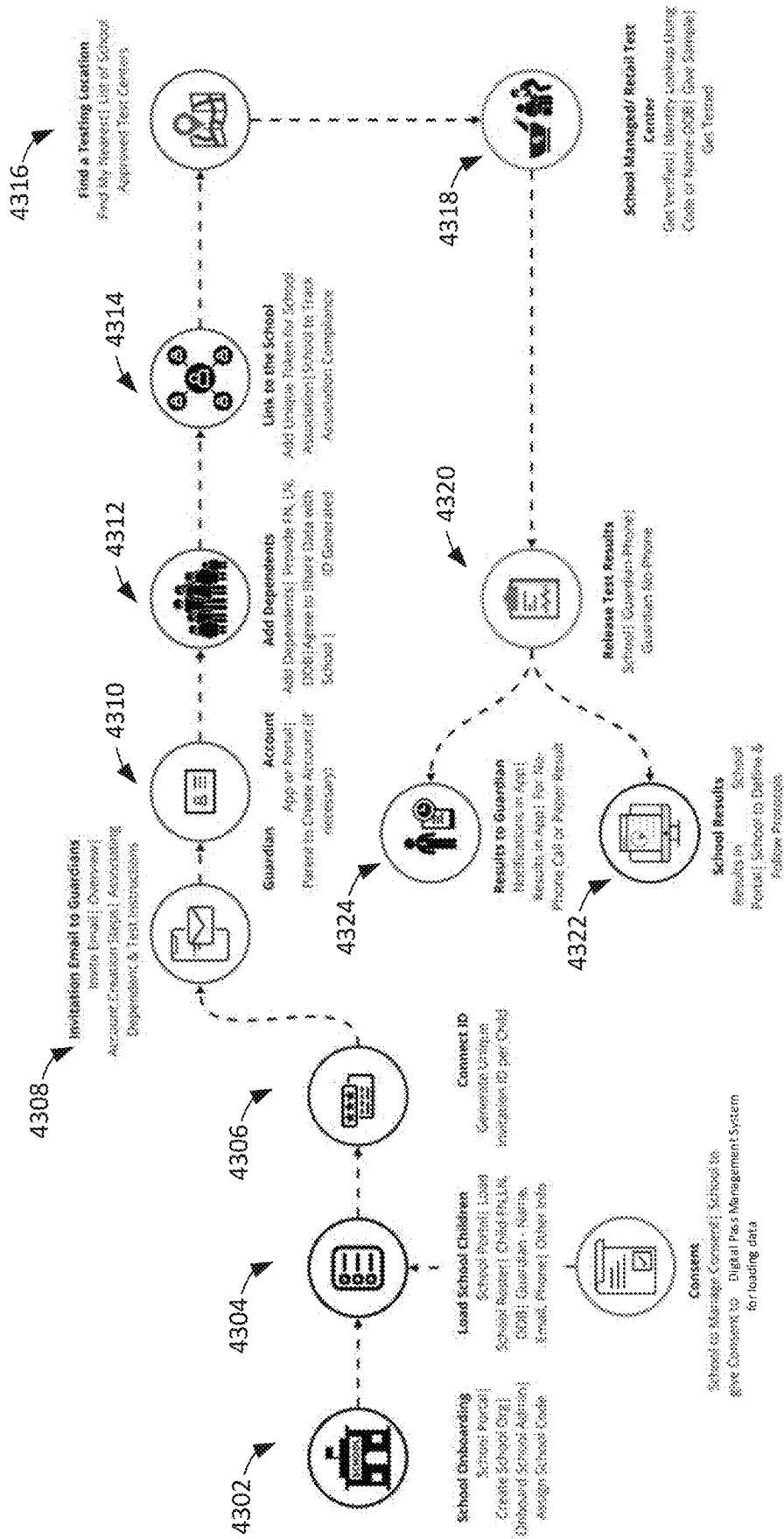
FIG. 43 is example timeline or sequence of events as performed and/or experienced by a digital pass management system, a user, a tester, and a verifier during an example digital pass verification process where a school is the verifier and a student and/or the student's parent is the user.

FIG. 43 shows an example timeline or sequence of events as performed and/or experienced by a digital pass management system, a user, a tester, and a verifier in connection with a digital pass verification process implemented in connection with a school as the verifier. The example timeline or sequence is described in connection with the digital pass management system 100, the user 102 (e.g., a parent or guardian), the tester 104, and the verifier 106 (e.g., a school). The school can use the digital pass verification techniques disclosed herein to confirm the staff and/or students have recently tested negative for an infectious disease before allowing the staff and/or students to enter the school. The example events can be performed in any other order and any of the events can be removed, replaced, and/or repeated.

At step 4302, the verifier 106 (e.g., the school) performs an onboarding process. The verifier 106 (e.g., the school) creates a school organization account with the digital pass management system 100. The verifier 106 (e.g., the school) can create the account using via the verifier application 120 on the verifier device 112 and/or another electronic device (e.g., a computer). The verifier 106 (e.g., the school) can log into the digital pass management system 100 to access and modify information associated with the school organization account. This may be referred to as a school portal. The verifier 106 (e.g., the school) can create administrative controls and privileges for certain people (e.g., human resources (HR) personnel).

At step 4304, the verifier 106 (e.g., the school) can load a school roster into the digital pass management system 100. The school roster may include the names and other identifying information (e.g., parent's names, email addresses, phone numbers, etc.) associated with each of the students. At step 4306, the digital pass management system 100 generates a unique invitation ID for each student. The unique invitation ID can be used to link the student's account or his/her parent's account to the school organization account. At step 4308, the digital pass management system 100 sends the invitation IDs to the parents (e.g., via email, via text message, via regular mail, etc.).

At steps 4310-4314, the user 102 (e.g., a parent) can create a user account for himself/herself and/or a dependent account/profile for the student via the user application 116 and connect their account(s) to the school organization account. Examples of this process are disclosed above in connection with FIGS. 6-11 and 33-38, for example.

At step 4316, the user 102 (e.g., a parent) can use the user application 116 to find a testing location and schedule a test (e.g., via the scheduler 208) to have the child tested. In some examples, only testing center approved by the verifier 106 (e.g., the school) are to be used. At step 4318, the child is tested. An example of the testing process is disclosed in connection with FIGS. 40A and 40B. The results of the tests are sent to the digital pass management system 100 and stored with the user's account.

At step 4320, the digital pass management system 100 releases the results of the tests to the verifier 106 (e.g., the school) and the associated users 102 (e.g., the parents). At step 4322, the verifier 106 (e.g., the school) can log into their account with the digital pass management system 100 to review the results of the students connected to the school organization account. At step 4324, the user 102 (e.g., a parent) can access the result of the test for his/her child in the user application 116. If the user's child tested negative, the user application 116 can generate a digital pass for the child, as disclosed in connection with FIGS. 26, 27A, 27B, 28A, and 28B. The user 102 (e.g., a parent) can use the user application 116 with the digital pass to enable the student to gain entry into the school. The verifier 106 (e.g., the school) may scan the digital pass on the user device 108 each time the student arrives at the school, for example.

Figure 44:
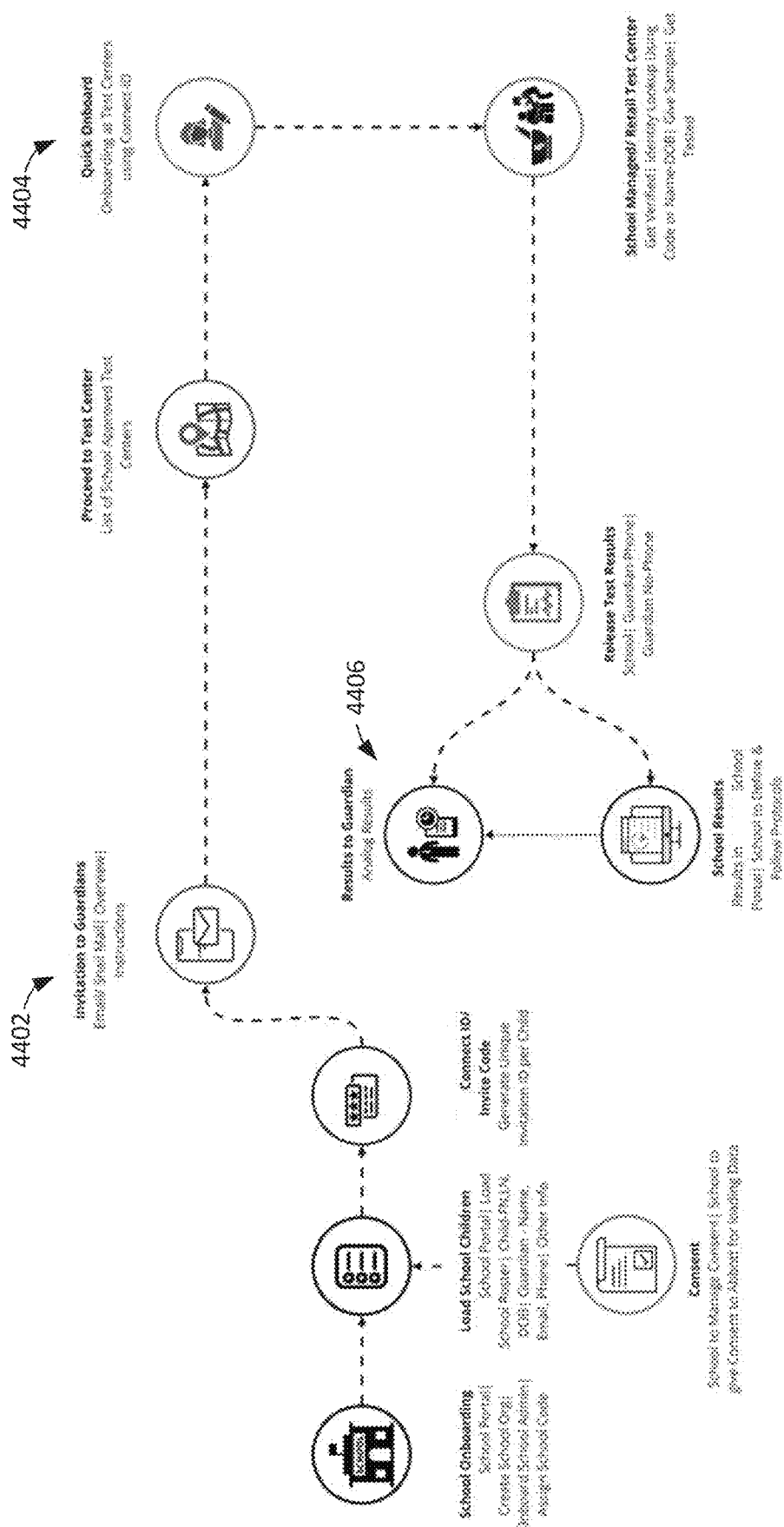
FIG. 44 is another example timeline or sequence of events as performed and/or experienced by a digital pass management system, a user, a tester, and a verifier during an example digital pass verification process where a school is the verifier and a student and/or the student's parent is the user and the user does not have an electronic mobile device.

If the user 102 does not have an electronic mobile device (e.g., a phone) to display a digital pass or does not have an electronic mobile device capable of displaying a digital pass, a similar digital pass verification process can be implemented in which certain information is mailed or emailed to the user 102. For example, FIG. 44 shows an example timeline or sequence of events that is similar to FIG. 43 except the user 102 does not have an electronic mobile device. In this example, at step 4402, the verifier 106 (e.g., the school) and/or the digital pass management system 100 physically mails the instructions and invitation ID (which may be referred to as a Connect-ID) to the user 102. In other examples, the instructions and invitation ID can be emailed to the user 102 who can print the instructions and invitation ID at home. During testing, at step 4404, the user 102 can present the invitation ID to the tester 104. The tester 104 can input the invitation ID into the tester application 118 to link the user 102 (and/or the dependent) to the test. At step 4406, the digital pass management system 100 and/or the verifier 106 (e.g., the school) can physically mail the results to the user 102 or email the results to the user 102, effectively providing the user 102 with the results in an analog manner rather than digitally. In some examples, the digital pass management system 100 and/or the verifier can physically mail the user 102 the digital pass and/or digital pass code on a piece of paper or email the digital pass to the user 102 to print out at home. The user 102 can then present the piece of paper to the verifier 106 as a pass.

While in some of the examples disclosed herein the tester 104 performs the test, in other examples, the user 102 can perform the test themselves. For example, the test may be performed via an at-home disposable test kit (e.g., a lateral flow test strip). In some examples, the user application 116 presents instructions to inform the user 102 on how to collect the sample for the diagnostic test. In some examples, after the test, the user 102 can then enter the results of the test into the user application 116. For example, the user application 116 can provide a notification similar to FIG. 25 for interpretation and entry of the result of the diagnostic test. Additionally or alternatively, the user application 116 can use the camera 207 to scan the test kit, and the analyzer 216 can analyze the image and automatically determine the result of the diagnostic test (e.g., by analyzing the lines and colors on the test kit). In such examples, the user application 116 communicates with the digital pass management system 100 to exchange the information disclosed above to be used in the generation of the digital pass 2800. The at-home test kit may be provided by the verifier 106 or may be paid for individually by the user 102. For example, a user planning to attend a concert may be responsible for obtaining his/her own test. In such an example, the user may order an at-home test kit (e.g., from the concert organization or a third-party organization). The user may conduct the at-home test, upload the results, and receive the digital pass prior to attending the concert. The user 102 can perform the test anywhere, such as at the user's home, a work place, a public facility, a school, etc.

As disclosed above, in some examples, rather than going to a testing facility to get tested, the user 102 may perform the diagnostic test himself/herself. In some examples, the user 102 may perform the test while being virtually monitored by the tester 104 (which may be referred to, in this example, as telehealth, telemed, telemedicine, electronic medicine, and/or virtual testing) to ensure the fidelity of the testing process. For example, the user application 116 can electronically connect the user device 108 with a telehealth service provide prior to collection of the sample. In some examples, the user device 108 and the tester device 110 connect via a video conference session. In such an example, the tester 104 can monitor and watch the user 102 while the user 102 collects his/her sample and performs the diagnostic. In some examples, the user 102 can use the user device 108 to can scan the test kit code on the test kit to obtain the test kit ID. The user application 116 transmits the test kit ID to the digital pass management system 100 to be stored with the user's account. When the test is completed, the user 102 can show the test kit with the result to the tester 104 via the video call. For example, the test kit may include a visual indication (e.g., lines) that indicate the result of the test. The tester 104 can then enter the results into the tester application 118 and transmit the results to the digital pass management system 100.

Figure 45:
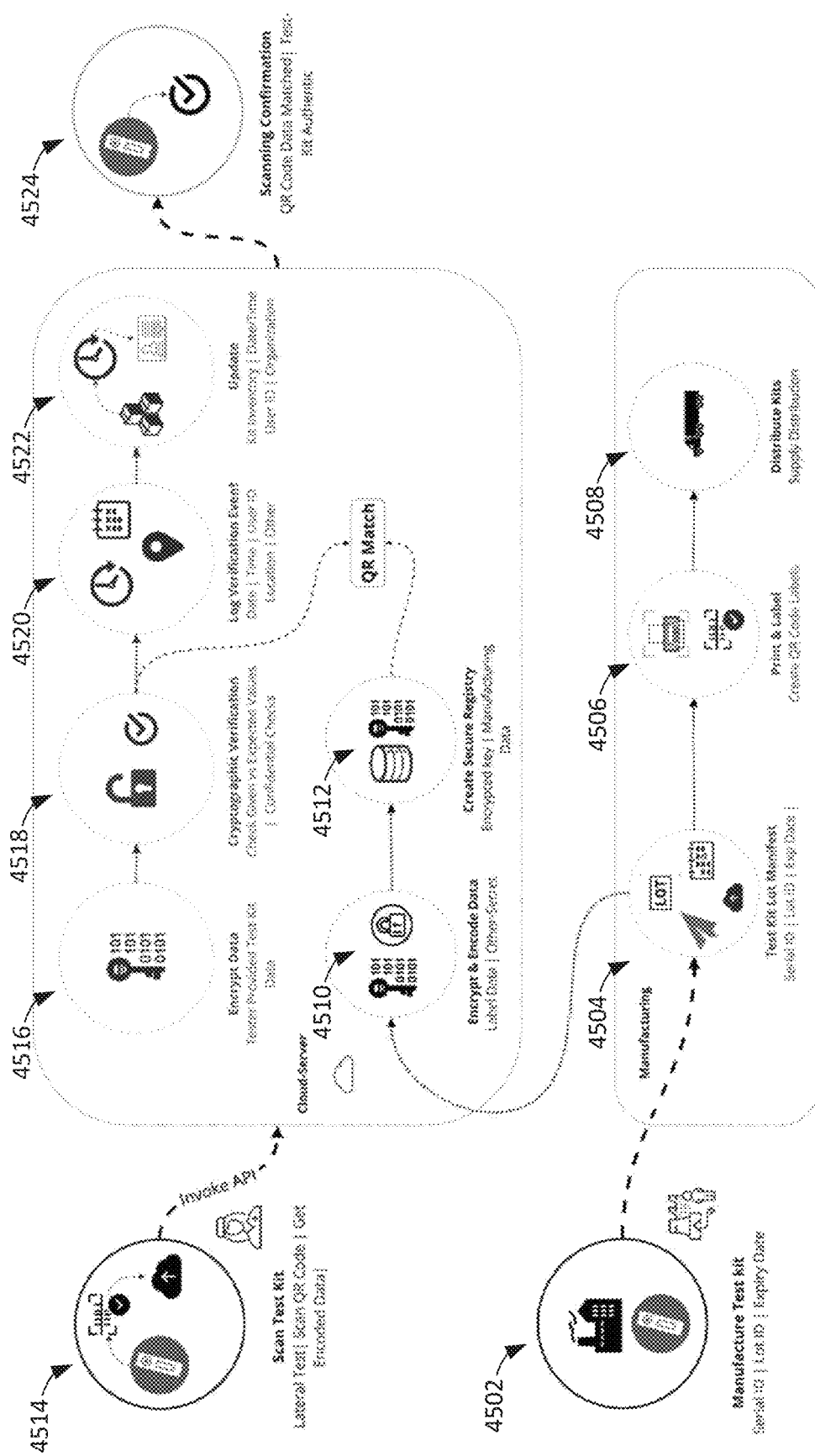
FIG. 45 is an example timeline or sequence of events as performed by and/or experience by a manufacturer and/or distributor of infectious disease test kits.

FIG. 45 shows an example timeline or sequence of events as performed and/or experienced by a manufacturer of the test kits. The example events can be performed in any other order and any of the events can be removed, replaced, and/or repeated.

At step 4502, the manufacturer of the test kits creates serial numbers, lot IDs and expiration dates for the test kits. At step 4504, the manufacture updates a test kit lot manifest. The manufacturing prints and labels the test kits the test kit codes (e.g., QR codes) (step 4506) and distributes the test kits (step 4508). In some examples, the test kit codes include the serial IDs, the lot IDs, and/or the expiration dates.

In some examples, the lot manifest is encrypted and the data is encoded (step 4510) and a secure registry is created (step 4512). In some examples, this secure registry is saved with the digital pass management system 100 and/or otherwise accessible for checking by the digital pass management system 100.

At step 4514, a new test kit is scanned by the tester application 118, which may correspond to steps 4008 and 4030 of FIGS. 40A and 40B. The tester application 118 sends the test kit ID (e.g., the serial ID, the lot ID, the expiration, etc.) that was embedded in the test kit code (step 4516). The digital pass management system 100 or another system verifies the test kit ID by matching the test kit ID with the test kit information in the secured registry (step 4518). The digital pass management system 100 or another system can log the verification event (step 4520) and update the kit inventory (step 4522). The digital pass management system 100 or another system sends the results back to the tester application 118 (step 4524). Steps 4510, 4512, 4516, 4518, 4520, and 4522 may be performed by the digital pass management system 100 and/or another system, such as a cloud-based server managed by the manufacturer.

While an example manner of implementing the example user application 116 and the example user device 108, the example tester application 118 and the example tester device 110, the example verifier application 120 and the example verifier device 112, and the example digital pass management system 100 are illustrated in FIGS. 1-5, one or more of the elements, processes and/or devices illustrated in FIGS. 1-5 may be combined, divided, re-arranged, omitted, eliminated and/or implemented in any other way. Further, the example user application 116, the example processor 200, the example memory 202, the example transceiver 204, the example display 206, the example camera 207, the example scheduler 208, the example notifier 210, the example code generator 212, the example time comparator 214, the example analyzer 216, the example tester application 118, the example processor 300, the example memory 302, the example transceiver 304, the example display 306, the example camera 308, the example record generator 310, the example test selector 312, the example sample indicator 314, the example comparator 316, the example reader 318, the example verifier application 120, the example processor 400 the example memory 402, the example transceiver 404, the example display 406, the example camera 408, the example detector 410, the example certifier 412, the example notifier 414, the example digital pass management system 100, the example processor 500, the example database 502, the example record generator 504, the example validator 506, and/or the example transceiver 508 of FIGS. 1-5 may be implemented by hardware, software, firmware and/or any combination of hardware, software and/or firmware. Thus, for example, any of the example user application 116, the example processor 200, the example memory 202, the example transceiver 204, the example display 206, the example camera 207, the example scheduler 208, the example notifier 210, the example code generator 212, the example time comparator 214, the example analyzer 216, the example tester application 118, the example processor 300, the example memory 302, the example transceiver 304, the example display 306, the example camera 308, the example record generator 310, the example test selector 312, the example sample indicator 314, the example comparator 316, the example reader 318, the example verifier application 120, the example processor 400 the example memory 402, the example transceiver 404, the example display 406, the example camera 408, the example detector 410, the example certifier 412, the example notifier 414, the example digital pass management system 100, the example processor 500, the example database 502, the example record generator 504, the example validator 506, and/or the example transceiver 508 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example user application 116, the example processor 200, the example memory 202, the example transceiver 204, the example display 206, the example camera 207, the example scheduler 208, the example notifier 210, the example code generator 212, the example time comparator 214, the example analyzer 216, the example tester application 118, the example processor 300, the example memory 302, the example transceiver 304, the example display 306, the example camera 308, the example record generator 310, the example test selector 312, the example sample indicator 314, the example comparator 316, the example reader 318, the example verifier application 120, the example processor 400 the example memory 402, the example transceiver 404, the example display 406, the example camera 408, the example detector 410, the example certifier 412, the example notifier 414, the example digital pass management system 100, the example processor 500, the example database 502, the example record generator 504, the example validator 506, and/or the example transceiver 508 is/are hereby expressly defined to include a non-transitory computer readable storage device or storage disk such as a memory, a digital versatile disk (DVD), a compact disk (CD), a Blu-ray disk, etc. including the software and/or firmware. Further still, the example user application 116, the example processor 200, the example memory 202, the example transceiver 204, the example display 206, the example camera 207, the example scheduler 208, the example notifier 210, the example code generator 212, the example time comparator 214, the example analyzer 216, the example tester application 118, the example processor 300, the example memory 302, the example transceiver 304, the example display 306, the example camera 308, the example record generator 310, the example test selector 312, the example sample indicator 314, the example comparator 316, the example reader 318, the example verifier application 120, the example processor 400 the example memory 402, the example transceiver 404, the example display 406, the example camera 408, the example detector 410, the example certifier 412, the example notifier 414, the example digital pass management system 100, the example processor 500, the example database 502, the example record generator 504, the example validator 506, and/or the example transceiver 508 of FIGS. 1-5 may include one or more elements, processes and/or devices in addition to, or instead of, those illustrated in FIGS. 1-5, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

In the illustrated example of FIG. 2, the analyzer 216 includes means for determining a result of a diagnostic test. In this example, the determining means is implemented by any processor structured to perform the corresponding operation by executing software or firmware, or hardware circuit (e.g., discrete and/or integrated analog and/or digital circuitry, an FPGA, a PLD, a FPLD, an ASIC, a comparator, an operational-amplifier (op-amp), a logic circuit, etc.) structured to perform the corresponding operation without executing software or firmware, but other structures are likewise appropriate. In some examples, the analyzer 216 implements the determining means.

In the illustrated example of FIG. 2, the code generator 212 includes means for accessing a test identification based on the result, accessing a user identification based on the result, constructing a machine-readable code based on the test identification and the user identification; and incorporating the code into a digital pass. In this example, the generating means is implemented by any processor structured to perform the corresponding operation by executing software or firmware, or hardware circuit (e.g., discrete and/or integrated analog and/or digital circuitry, an FPGA, a PLD, a FPLD, an ASIC, a comparator, an operational-amplifier (op-amp), a logic circuit, etc.) structured to perform the corresponding operation without executing software or firmware, but other structures are likewise appropriate. In some examples, the code generator 212 implements the determining means.

In the illustrated example of FIG. 2, the output 218 includes means for displaying or outputting for display the digital pass. In this example, the outputting means is implemented by any processor structured to perform the corresponding operation by executing software or firmware, or hardware circuit (e.g., discrete and/or integrated analog and/or digital circuitry, an FPGA, a PLD, a FPLD, an ASIC, a comparator, an operational-amplifier (op-amp), a logic circuit, etc.) structured to perform the corresponding operation without executing software or firmware, but other structures are likewise appropriate. In some examples, the output 218 implements the outputting means.

In the illustrated example of FIG. 2, the scheduler 208 includes means for determining a validity of the digital pass based on an expiration date. In this example, the means for determining validity is implemented by any processor structured to perform the corresponding operation by executing software or firmware, or hardware circuit (e.g., discrete and/or integrated analog and/or digital circuitry, an FPGA, a PLD, a FPLD, an ASIC, a comparator, an operational-amplifier (op-amp), a logic circuit, etc.) structured to perform the corresponding operation without executing software or firmware, but other structures are likewise appropriate. In some examples, the scheduler 208 implements the means for determining validity.

In the illustrated example of FIG. 2, the notifier 210 includes means for prompting scheduling of a test when the time comparator determines the digital pass is not valid In this example, the prompting means is implemented by any processor structured to perform the corresponding operation by executing software or firmware, or hardware circuit (e.g., discrete and/or integrated analog and/or digital circuitry, an FPGA, a PLD, a FPLD, an ASIC, a comparator, an operational-amplifier (op-amp), a logic circuit, etc.) structured to perform the corresponding operation without executing software or firmware, but other structures are likewise appropriate. In some examples, the notifier 210 implements the prompting means.

Figure 46A:
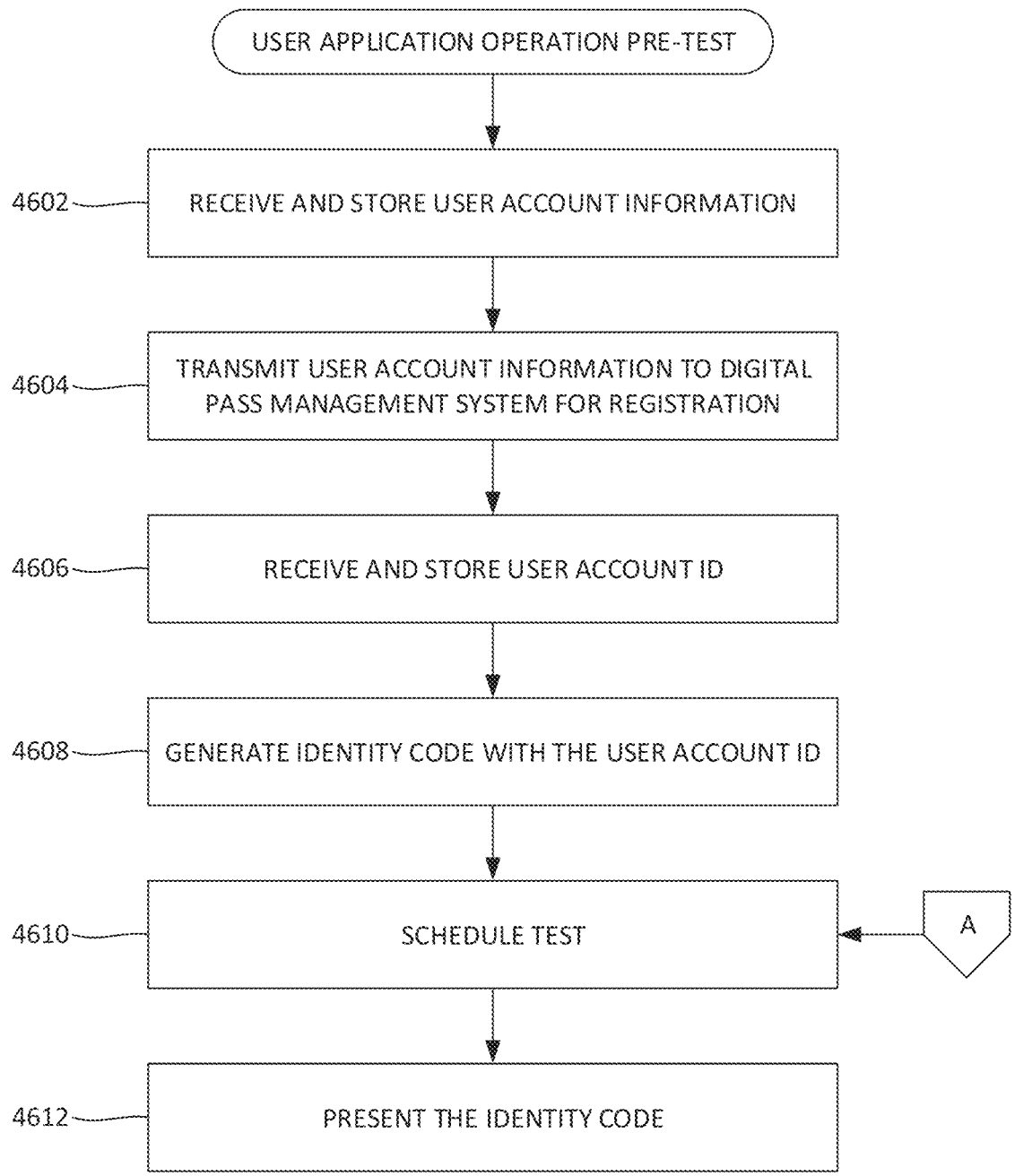
FIGS. 46A and 46B are flowcharts representative of example machine readable instructions that may be executed to implement the example user application on the example user device of FIG. 2.
Figure 46B:
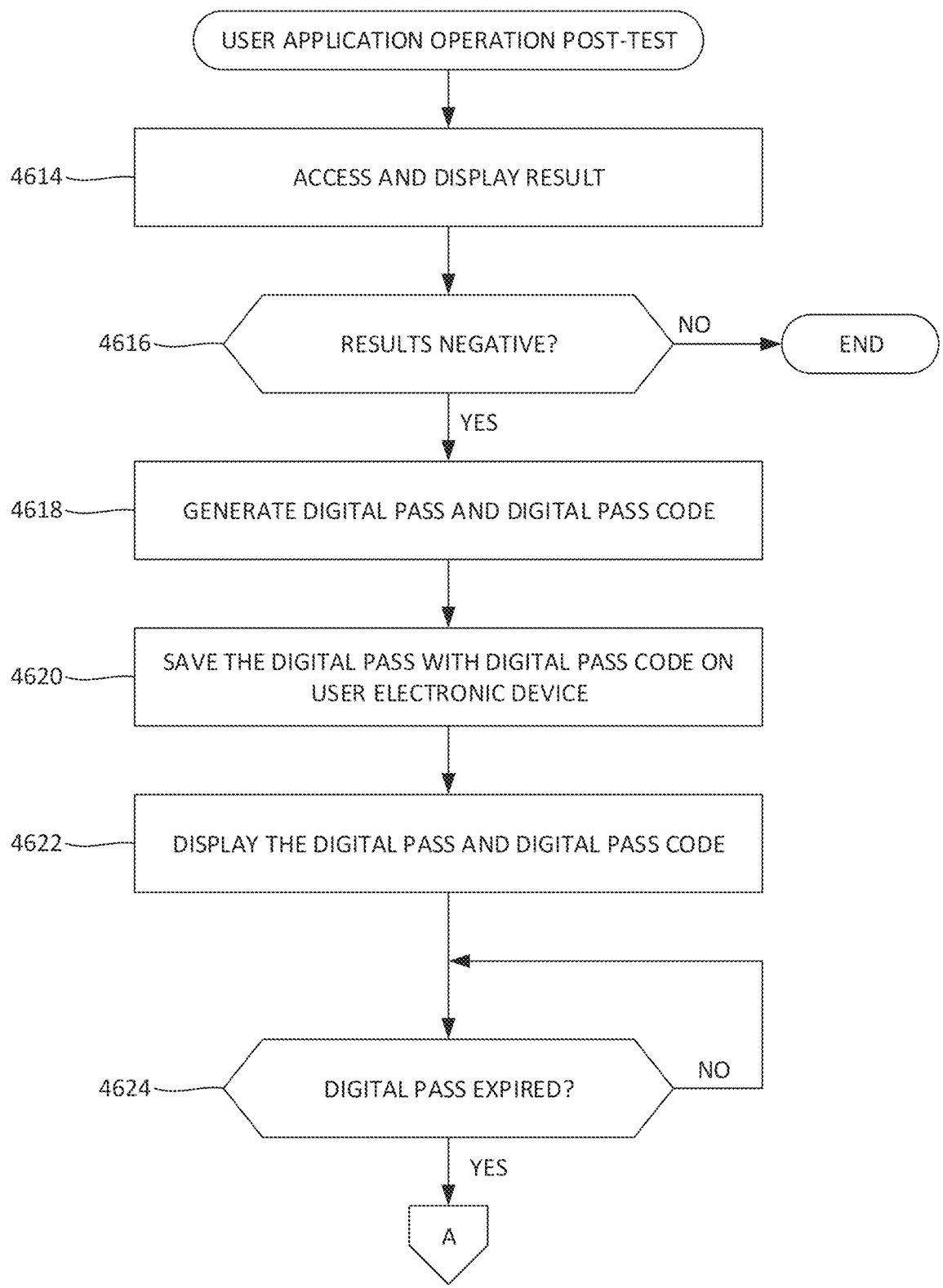

A flowchart representative of example hardware logic, machine readable instructions, hardware implemented state machines, and/or any combination thereof for implementing the user application 116 of FIGS. 1 and 2 is shown in FIGS. 46A and 46B. The machine readable instructions may be one or more executable programs or portion(s) of an executable program for execution by a computer processor and/or processor circuitry, such as the processor 5012 shown in the example processor platform 5000 discussed below in connection with FIG. 50. The program may be embodied in software stored on a non-transitory computer readable storage medium such as a CD-ROM, a floppy disk, a hard drive, a DVD, a Blu-ray disk, or a memory associated with the processor 5012, but the entire program and/or parts thereof could alternatively be executed by a device other than the processor 5012 and/or embodied in firmware or dedicated hardware. Further, although the example program is described with reference to the flowchart illustrated in FIGS. 46A and 46B, many other methods of implementing the example user application 116 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more devices (e.g., a multi-core processor in a single machine, multiple processors distributed across a server rack, etc.).

Figure 47:
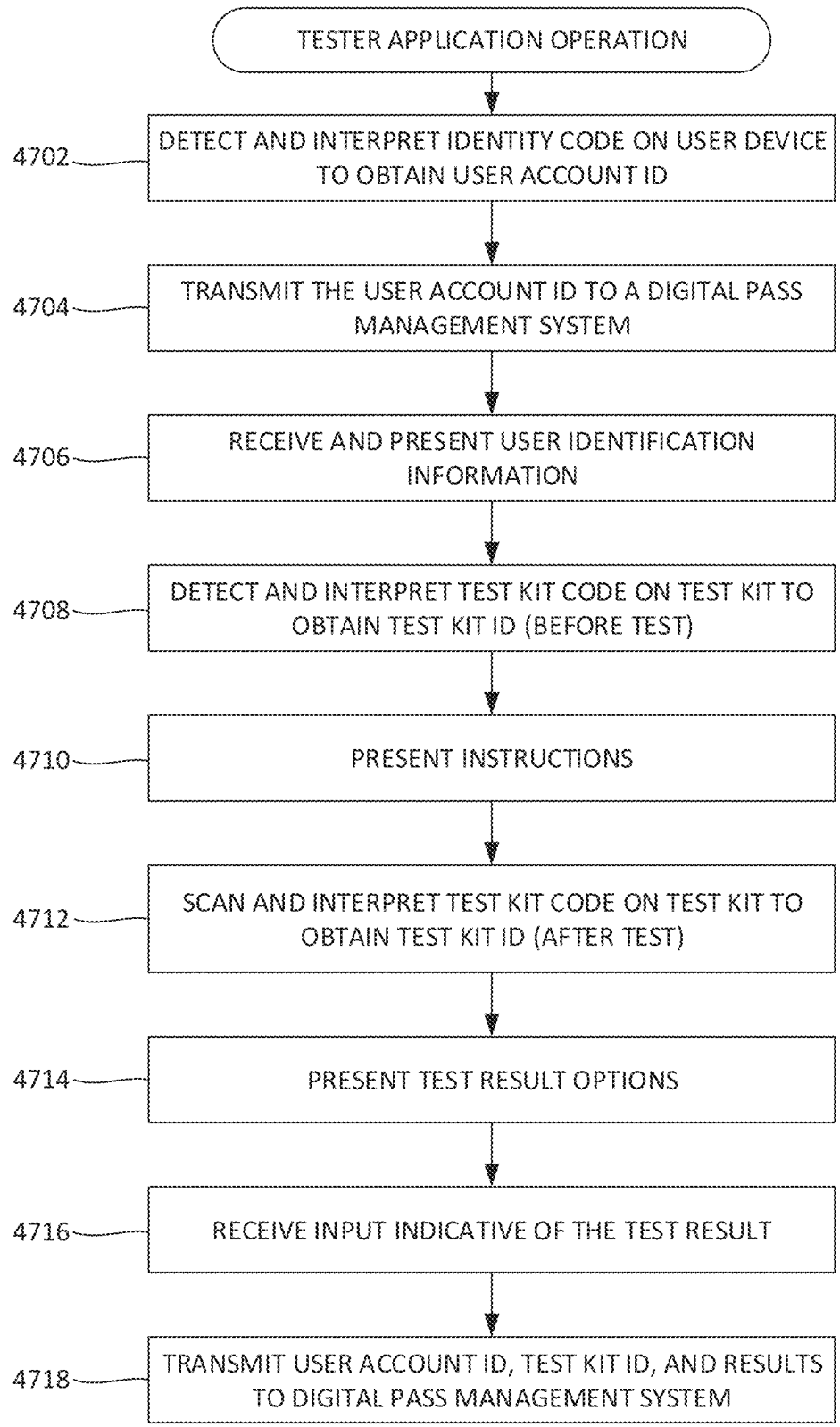
FIG. 47 is a flowchart representative of example machine readable instructions that may be executed to implement the example tester application on the example tester device of FIG. 3.

A flowchart representative of example hardware logic, machine readable instructions, hardware implemented state machines, and/or any combination thereof for implementing the tester application 118 of FIGS. 1 and 3 is shown in FIG. 47. The machine readable instructions may be one or more executable programs or portion(s) of an executable program for execution by a computer processor and/or processor circuitry, such as the processor 5112 shown in the example processor platform 5100 discussed below in connection with FIG. 51. The program may be embodied in software stored on a non-transitory computer readable storage medium such as a CD-ROM, a floppy disk, a hard drive, a DVD, a Blu-ray disk, or a memory associated with the processor 5112, but the entire program and/or parts thereof could alternatively be executed by a device other than the processor 5112 and/or embodied in firmware or dedicated hardware. Further, although the example program is described with reference to the flowchart illustrated in FIG. 47, many other methods of implementing the example tester application 118 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more devices (e.g., a multi-core processor in a single machine, multiple processors distributed across a server rack, etc.).

Figure 48:
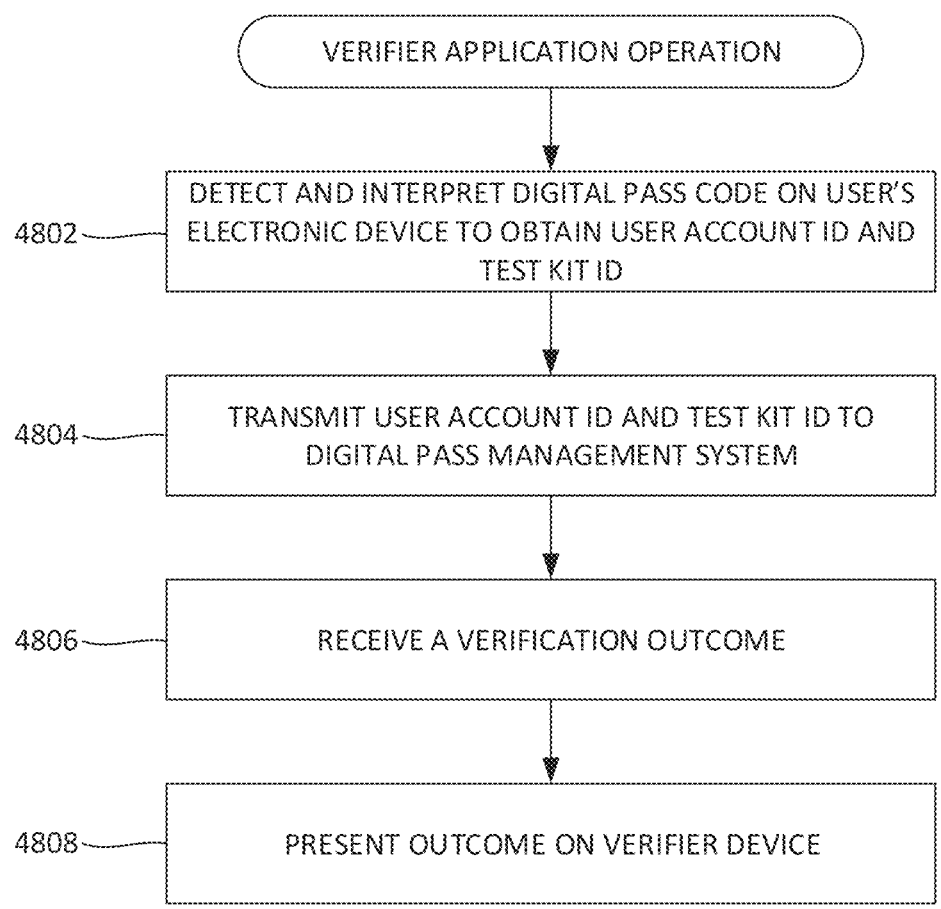
FIG. 48 is a flowchart representative of example machine readable instructions that may be executed to implement the example verifier application on the example verifier device of FIG. 4.

A flowchart representative of example hardware logic, machine readable instructions, hardware implemented state machines, and/or any combination thereof for implementing the verifier application 120 of FIGS. 1 and 4 is shown in FIG. 48. The machine readable instructions may be one or more executable programs or portion(s) of an executable program for execution by a computer processor and/or processor circuitry, such as the processor 5212 shown in the example processor platform 5200 discussed below in connection with FIG. 52. The program may be embodied in software stored on a non-transitory computer readable storage medium such as a CD-ROM, a floppy disk, a hard drive, a DVD, a Blu-ray disk, or a memory associated with the processor 5212, but the entire program and/or parts thereof could alternatively be executed by a device other than the processor 5212 and/or embodied in firmware or dedicated hardware. Further, although the example program is described with reference to the flowchart illustrated in FIG. 48, many other methods of implementing the example verifier application 118 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more devices (e.g., a multi-core processor in a single machine, multiple processors distributed across a server rack, etc.).

Figure 49:
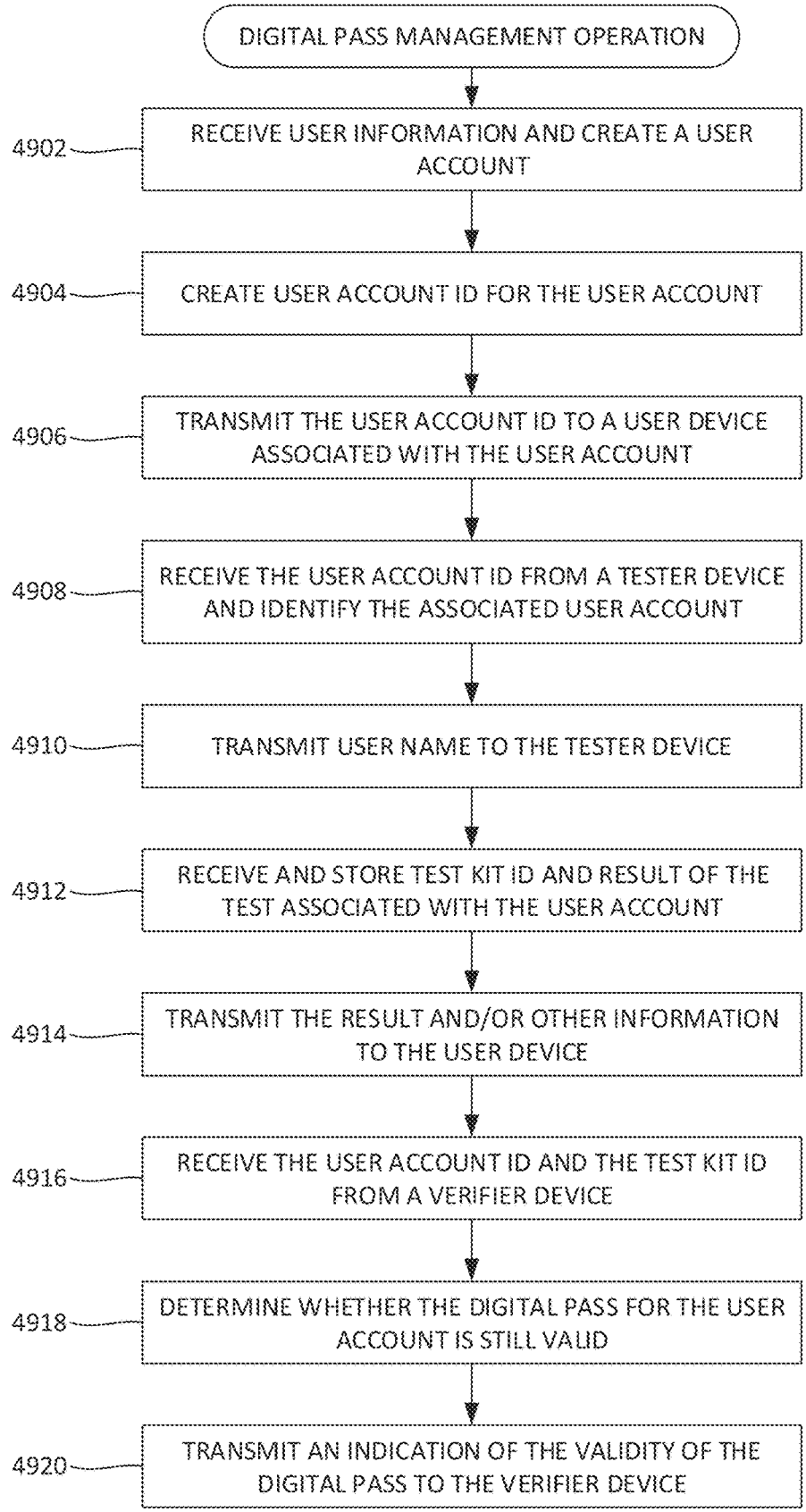
FIG. 49 is a flowchart representative of machine readable instructions which may be executed to implement the example digital pass management system of FIGS. 1 and 5.

A flowchart representative of example hardware logic, machine readable instructions, hardware implemented state machines, and/or any combination thereof for implementing the digital pass management system 100 of FIGS. 1 and 5 is shown in FIG. 49. The machine readable instructions may be one or more executable programs or portion(s) of an executable program for execution by a computer processor and/or processor circuitry, such as the processor 5312 shown in the example processor platform 5300 discussed below in connection with FIG. 53. The program may be embodied in software stored on a non-transitory computer readable storage medium such as a CD-ROM, a floppy disk, a hard drive, a DVD, a Blu-ray disk, or a memory associated with the processor 5312, but the entire program and/or parts thereof could alternatively be executed by a device other than the processor 5312 and/or embodied in firmware or dedicated hardware. Further, although the example program is described with reference to the flowchart illustrated in FIG. 49, many other methods of implementing the example digital pass management system 100 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more devices (e.g., a multi-core processor in a single machine, multiple processors distributed across a server rack, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc. in order to make them directly readable, interpretable, and/or executable by a computing device and/or other machine. For example, the machine readable instructions may be stored in multiple parts, which are individually compressed, encrypted, and stored on separate computing devices, wherein the parts when decrypted, decompressed, and combined form a set of executable instructions that implement one or more functions that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc. in order to execute the instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example processes of FIGS. 46A, 46B, 47, 48, and 49 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, and (3) at least one A and at least one B.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

FIGS. 46A and 46B are flowcharts representative of instructions executed by the user device 108 (e.g., by the processor 200 of the user device 108) to implement the user application 116 and/or otherwise implement operations performed on the user device 108. In some examples, the user 102 downloads the user application 116 onto the user device 108 (e.g., from the digital pass management system 100, the Apple App Store, and/or the Google Play Store). In other examples, the user application 116 can be pre-installed on the user device 108. The user 102 can open the user application 116 and create an account (e.g., by entering his/her name, birthday, etc.). Example interfaces screens for creating an account are shown in FIGS. 6-11. At block 4602, the user application 116 receives and stores (e.g., in the memory 202) the account information entered by the user 102.

At block 4604, the user application 116 transmits (e.g., communicates with the transceiver 204 via the internet) the user account information to the digital pass management system 100 for registration. The record generator 504 of the digital pass management system 100 creates and stores a record of the user account in the database 502. The record generator 504 of the digital pass management system 100 creates a user account ID for the user account. The digital pass management system 100 transmits (e.g., communicates with the transceiver 508) the user account ID to the user device 102. At block 4606, the transceiver 204 receives the user account ID, and the user application 116 stores the user account ID (e.g., in the memory 202).

At block 4608, the code generator 212 of the user application 116 generates the identity code 1200 (e.g., a QR code, a Data Matrix Code, other machine-readable codes) with the user account ID. The identity code 1200 can be used to confirm the identity of the user 102 when the user 102 is tested. The user application 116 stores the identity code 1200 (e.g., in the memory 202).

In some examples, to get tested for an infectious disease, the user 102 can schedule an appointment. For example, at block 4610, the user 102 uses the scheduler 208 of the user application 116 to schedule a test with a testing facility. In other examples, the user 102 can proceed to the testing facility without an appointment.

The user 102 shows the identity code 1200 to the tester 104. For example, at block 4612, the user application 116 presents the identity code 1200 on the display 206 of the user device 108 (e.g., FIG. 12). The tester 104 scans the identity code 104 with the tester device 110. The tester 104 also performs the test as disclosed herein.

In some examples, the user 102 may perform the test themselves. In some such examples, the user application 116 may present instructions to inform the user device 108 how to collect the sample and/or perform the test. In some examples, the user 102 may enter his/her results into the user application 116. For example, the user application 116 can provide a notification similar to FIG. 25 for interpretation and entry of the result of the diagnostic test. The user 102 can then select the appropriate result. Additionally or alternatively, the user application 116 can use the camera 207 to scan the test kit, and the analyzer 216 can analyze the image and automatically determine the result of the diagnostic test (e.g., by analyzing the lines and colors on the test kit). In such examples, the user application 116 communicates with the digital pass management system 100 to exchange the information disclosed above to be used in the generation of the digital pass 2800. In other examples, a remote tester may monitor the user during the testing process. In such examples, the user application 116 can electronically connect with a telehealth service provider prior to collection of the sample. Also, in this example, the remote tester enters the results via a tester device.

Referring to FIG. 46B, at block 4614, the user application 116 accesses and displays the result on the user device 108. In particular, after the test, the result is transmitted to the user device 108 by the tester 104 and/or the digital pass management system 100 as disclosed herein. In some examples, the digital pass management system 100 may automatically transmit the test result to the user application 116 when the digital pass management system 100 receives the result from the tester 104. In other examples, the user application 116 may request the result from the digital pass management system 100. In some examples, the test kit ID and other information is/are also transmitted to the user device 108. The transceiver 204 receives the results, and the notifier 210 displays the results. Examples of these displays are shown in FIGS. 26, 27A, and 27B. The notifier 210 of the user application 116 may display different information depending on the result of the diagnostic test. For example, if the result was positive for the infectious disease, the notifier 210 of the user application 116 may display certain guidelines or suggestions. If the result was negative for the infectious disease, the notifier 210 of the user application 116 may display other guidelines or suggestions. If the result was invalid (e.g., inconclusive), the notifier 210 of the user application 116 may present a suggestion to take the test again.

At block 4616, the analyzer 216 of the user application 116 determines if the result was negative for the infectious disease. In some examples, if the result was not negative (i.e., the result was positive or invalid), the example process may end, and a digital pass is not generated. In other examples, if the analyzer 216 of the user application 116 determines that the result was not negative, the example process may continue with the user 102 scheduling another test (block 4610). If the result was negative, at block 4618, the code generator 212 of the user application 116 generates the digital pass 2800 including the digital pass code 2802 (e.g., a QR code, a Data Matrix Code, and/or other types of machine-readable codes). In some examples, the digital pass code 2802 includes the account ID associated with the user's account and the test kit ID of the test kit used to perform the test. Therefore, the user application 116 accesses the user account ID (e.g., stored in the memory 202) and the test kit ID (e.g., stored in the memory 202) and generates the digital pass code 2802 based on the user account ID and the test kit ID. Example digital passes 2800, 2804 and digital pass codes 2802, 2806 are shown in FIGS. 28A and 28B. At block 4620, the user application 116 saves the digital pass, such as the digital pass 2800 (e.g., in the memory 202). In some examples, the digital pass 2800 is saved in a digital wallet on the user device 108, which can be accessed without the user application 116.

The user 102 can then present the digital pass 2800 to one or more verifiers as needed. At block 4622, the user application 116 presents or displays the digital pass 2800 (including the digital pass code 2802) on the display 206 of the user device 108. The digital pass 2800 can be used to enable the user 102 to gain entry into a location. The digital pass 2800 can be used multiple times with the same verifier or different verifiers.

At block 4624, the time comparator 214 of the user application 116 determines whether the digital pass 2800 has expired. If the digital pass 2800 has not expired, the digital pass 2800 is still valid and can continue to be used. If the digital pass 2800 has expired, the user 102 can get re-tested (e.g., proceeding to block 3810) and the example process continues from there.

The example process shown in FIGS. 46A and 46B can be repeated each time the user 102 (and/or a dependent associated with the user 102) is tested. The user application 116 can manage multiple digital passes for the user 102. The example process can be used in connection with the same type of test (e.g., for a same analyte of interest) or different types of tests (e.g., for different analytes of interest).

FIG. 47 is a flowchart representative of instructions executed by the tester device 110 (e.g., by the processor 300 of the tester device 110) to implement the tester application 118 and/or otherwise implement operations performed on the tester device 110. In some examples, the tester 104 downloads the tester application 118 onto the tester device 110 (e.g., from the digital pass management system 100, the Apple App Store, and/or the Google Play Store). In other examples, the tester application 118 can be pre-installed on the tester device 110.

In some examples, before testing the user 102, the tester 104 creates a new test record by identifying the user 102. As disclosed above, the user 102 can present the identity code 1200 on the user device 108 to the tester 104. The tester 104 uses the tester device 110 to scan the identity code 1200. For example, the tester device 110 may include the camera 308, which can be used to scan the identity code 1200. In some examples, the tester application 118 displays the video feed from the camera 308 to enable the tester 104 to align the identity code 1200 in view of the camera 308. An example of this interface is shown in FIG. 16. At block 4702, the record generator 310 of the tester application 118 detects and interprets the identity code 1200 to obtain the user account ID (and/or other identifying information associated with the user 102) embedded in the identity code 1200.

At block 4704, the tester application 118 transmits the user account ID to the digital pass management system 100 using, for example, the transceiver 304. In some examples, the digital pass management system 100 returns the name and/or other identifying information associated with the user 102 so that the tester 104 can confirm the identity of the user 102. At block 4706, the tester application 118 receives (e.g. via the transceiver 304) and presents the user identification information on the tester device 110. An example user interface showing the user identification information on the tester device 110 is shown in FIG. 17. In some examples, the tester 104 confirms the user's identity via a driver's license or other form of identification. If the user's identity matches, the tester 104 proceeds to perform the test. As disclosed herein, various types of tests can be used.

Depending on the type of test, the test kit or test cartridge contains a test kit code with a unique test kit ID. The tester 104 uses the tester device 110 to scan the test kit code on the test kit or test cartridge. In some examples, the tester application 118 displays the video feed from the camera 308 to enable the tester 104 to align the test kit code in view of the camera 308. An example of this interface is shown in FIG. 20. At block 4708, the record generator 310 of the tester application 118 detects and interprets the test kit code to obtain the test kit ID embedded in the test kit code.

In some examples, at block 4710, the tester application 118 presents instructions on how to perform the test. An example of this interface is shown in FIG. 21. After performing the test, the tester 104 (or another tester) can rescan the test kit code on the test kit. At block 4712, the tester application scans and interprets the test kit code to receive the test kit ID. An example of this interface is shown in FIG.

24. In some examples, this second scan is used to prevent an accidental mix-up of test kits. In other examples, a second scan is not performed.

At block 4714, the tester application 118 presents a user interface with selectable options for the results of the test. An example of this user interface is shown in FIG. 25. The tester 104 can select the appropriate test result. Therefore, the tester application 118 provides a notification for the interpretation and entry of the result of the diagnostic test. At block 4716, the tester application 118 receives input (e.g., from the tester 104 selecting the option on the display 306) indicative of the result of the diagnostic test.

At block 4718, the tester application 118 transmits the user account ID, the test kit ID (from one or both scans), and the test results to the digital pass management system 100 (using, for example, the transceiver 304). The results are saved in the database 502 with the user account and sent to the user device 108. In some examples, the tester application 118 transmits an image of the test kit used in the diagnostic device to be saved in the database 502. In addition to or as an alternative to sending the information to the digital pass management system 100, the tester application 118 can also send the information directly to the user device 108.

FIG. 48 is a flowchart representative of instructions executed by the verifier device 112 (e.g., by the processor 400 of the verifier device 112) to implement the verifier application 120 and/or otherwise implement operations performed on the verifier device 112. In some examples, the verifier 106 downloads the verifier application 120 onto the verifier device 112 (e.g., from the digital pass management system 100, the Apple App Store, and/or the Google Play Store). In other examples, the verifier application 120 can be pre-installed on the verifier device 112.

When the user 102 intends to gain access to the location monitored by the verifier 106, the user 102 can present the digital pass 2800 on the user device 108. The verifier 106 uses the verifier device 112 to scan the digital pass code 2802. For example, the verifier device 112 may include the camera 408, which can be used to scan the digital pass code 2802. In some examples, the verifier application 120 displays the video feed from the camera 408 to enable the verifier 106 to align the digital pass code 2802 in view of the camera 408. An example of this interface is shown in FIG. 29. At block 4802, the detector 410 of the verification application 120 detects the digital pass code 2802 displayed on the user device 108, and the certifier 412 interprets the digital pass code 2802 to obtain the user account ID and the test kit ID. Thus, the verifier application 120 can determine the user account ID and test kit ID based on the digital pass code 2802. In other examples, the digital pass code 2802 can contain other identifying information that can be retrieved by the verifier application 120 when scanning the digital pass code 2802.

At block 4804, the verifier application 120 transmits the user account ID and test kit ID to the digital pass management system 100 (e.g., using the transceiver 404). In some examples, the validator 506 of the digital pass management system 100 determines whether the user account ID and the test kit ID match in the user account. The validator 506 of the digital pass management system 100 also confirms that the result of the test was negative. In some examples, the validator 506 of the digital pass management system 100 also confirms that the expiration date has not passed. The digital pass management system 100 transmits a verification outcome based on whether the digital pass 2800 is determined to be valid, invalid (e.g., expired), or not found to the verifier device 112 (e.g., using the transceiver 508). At block 4806, the verifier application 120 receives (e.g., via the transceiver 404) the verification outcome from the digital pass management system 100. The notifier 414 of the verifier application 120, at block 4808, presents the results. If the digital pass 2800 is valid and not expired, the certifier 412 of the verifier application 120 indicates that the digital pass 2800 is valid. An example of this interface is shown in FIG. 30. The verifier 106 may then allow the user 102 to enter the location.

If the digital pass 2800 is expired or not valid (e.g., because the user 102 has been removed from the verifier organization), the certifier 412 of the verifier application 120 may indicate the digital pass 2800 is expired or not valid. An example of this interface is shown in FIG. 31. In such an instance, the verifier 106 can deny the user 102 access to the location (e.g., an airplane, an office, a mall, a controlled outdoor space, etc.). In some examples, the user 102 has to get tested again to obtain a new, valid digital pass.

If the digital pass is not found, such as if no user account is found, the certifier 412 of the verifier application 120 may indicate the pass is not found. An example of this interface is shown in FIG. 33. In some examples, in addition to or as an alternative to displaying the verification outcome, the verification application 120 can automatically unlock at least one of a door, a gate, or a turnstile based on the verification outcome to enable or deny access to the user 102.

FIG. 49 is a flowchart representative of instructions executed (e.g., by the processor 500) to implement the digital pass management system 100. As disclosed above, the user 102 can create an account by entering user information in the user application 116 on the user device 108. At block 4902, the digital pass management system 100 receives the user information from the user application 116 and the record generator 504 creates a user account. The user account can be saved in the database 502. An example data entry 510 for the user account is shown in FIG. 5. At block 4104, the record generator 504 of the digital pass management system 100 creates a unique user account ID for the user account. At block 4906, the digital pass management system 100 transmits the user account ID to the user device 108 (e.g., using the transceiver 508). The user account ID can be used to generate the identity code 1200, the digital pass 2800, and the digital pass code 2802, as disclosed in connection with FIGS. 46A and 46B.

As disclosed above, when the user 102 is at the testing facility, the tester 104 scans the identity code 1200 on the user device 108 to obtain the user account ID. The tester application 118 sends the user account ID to the digital pass management system 100. At block 4908, the digital pass management system 100 receives the user account ID from the tester device 110 (e.g., via the tester application 118) and the validator 506 identifies the associated user account. At block 4910, the digital pass management system 100 transmits the user name (and/or other identifying information) to the tester device 110 (e.g., using the transceiver 508). The tester 104 can use the user name to confirm the identity of the user 102 before or after performing the test.

As disclosed above, after the test is performed, the test kit ID and result information is/are sent to the digital pass management system 100. At block 4912, the digital pass management system 100 receives and stores the test kit ID and result of the test associated with the user account. In particular, when the digital pass management system 100 receives the test kit ID and the result, the processor 500 associates the test kit ID and result of the diagnostic test with the user account ID and saves this information in the database 502 with the user account (e.g., in the data entry 510). Thereafter, the processor 500 can access the result of the diagnostic test associated with the test kit ID. At block 4914, the digital pass management system 100 transmits the result of the test to the user device 108 (e.g., using the transceiver 508). In some examples, in addition to the result, the digital pass management system 100 transmits the test kit ID to the user device 108. The test kit ID may be used in the digital pass code 2802, as disclosed herein. In some examples, the digital pass management system 100 verifies at least one of an expiration date of the test kit or a recall status of the test kit based on the test kit prior to transmitting the result of the diagnostic test and the test kit ID. In some examples, the digital pass management system 100 verifies an authenticity of the test kit based on the test kit ID prior to transmitting the result of the diagnostic test and the test kit ID to the user device 108. Additionally or alternatively, the digital pass management system 100 can transmit other information to the user device 108, such as the date of the diagnostic test, the type of test, etc. As disclosed above, the result can be used to create a digital pass on the user device 108.

As disclosed above, the verifier 106 can scan the digital pass code 2802 on the user device 108 to obtain the user account ID and test kit ID. The verifier application 120 sends the user account ID and test kit ID to the digital pass management system 100. At block 4916, the digital pass management system 100 receives the user account ID and the test kit ID from the verifier device 112 (e.g., via the verifier application 120). At block 4918, the validator 506 of the digital pass management system 100 determines whether the digital pass 2800 for the user account is still valid. In some examples, the validator 506 of the digital pass management system 100 confirms that the test kit ID matches the test kit ID associated with the user account. The validator 506 verifies the result of the test based on the user account ID and the test kit ID. In other words, the validator 506 matches the user account ID and the test kit ID with the test result of the diagnostic test. For example, the validator 506 of the digital pass management system 100 determines whether the result of the test associated with the user account for that test kit ID is negative. In some examples, the validator 506 of the digital pass management system 100 confirms whether the digital pass 2800 has not expired. For example, the validator 506 can determine a number of days since the diagnostic test and compare the number of days to a threshold number of days. If the number of days satisfies the threshold (e.g., is at or below the threshold), the validator 506 determines the digital pass 2800 is still valid. If the number of days does not satisfy the threshold (e.g., is above the threshold), the validator 506 determines the digital pass 2800 is not valid. In some examples, even if the number of days satisfies the threshold, the validator 506 can invalidate the digital pass 2800, such as if the user 102 is no longer employed at the verifier organization and the verifier organization has deactivated the user's passes.

Figure 32:
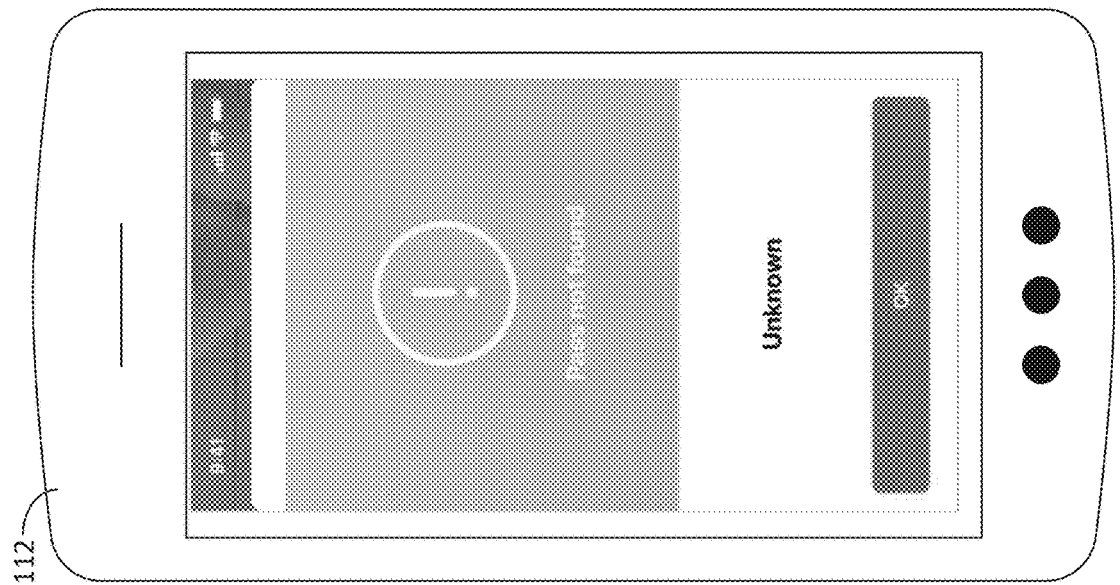

At block 4920, the digital pass management system 100 transmits a verification outcome (e.g., valid, invalid (expired), or not found), indicating the validity of the digital pass 2800, to the verifier device 112 (e.g., using the transceiver 508). The verification outcome can include a first notice when the result of the diagnostic test is negative and the number of days since the diagnostic test is below the threshold number of days, a second notice when the number of days since the diagnostic test is greater than the threshold, or a third notice when the digital pass is not found. The verifier application 120 displays a message associated with the verification outcome, as shown in FIGS. 30-32.

Figure 50:
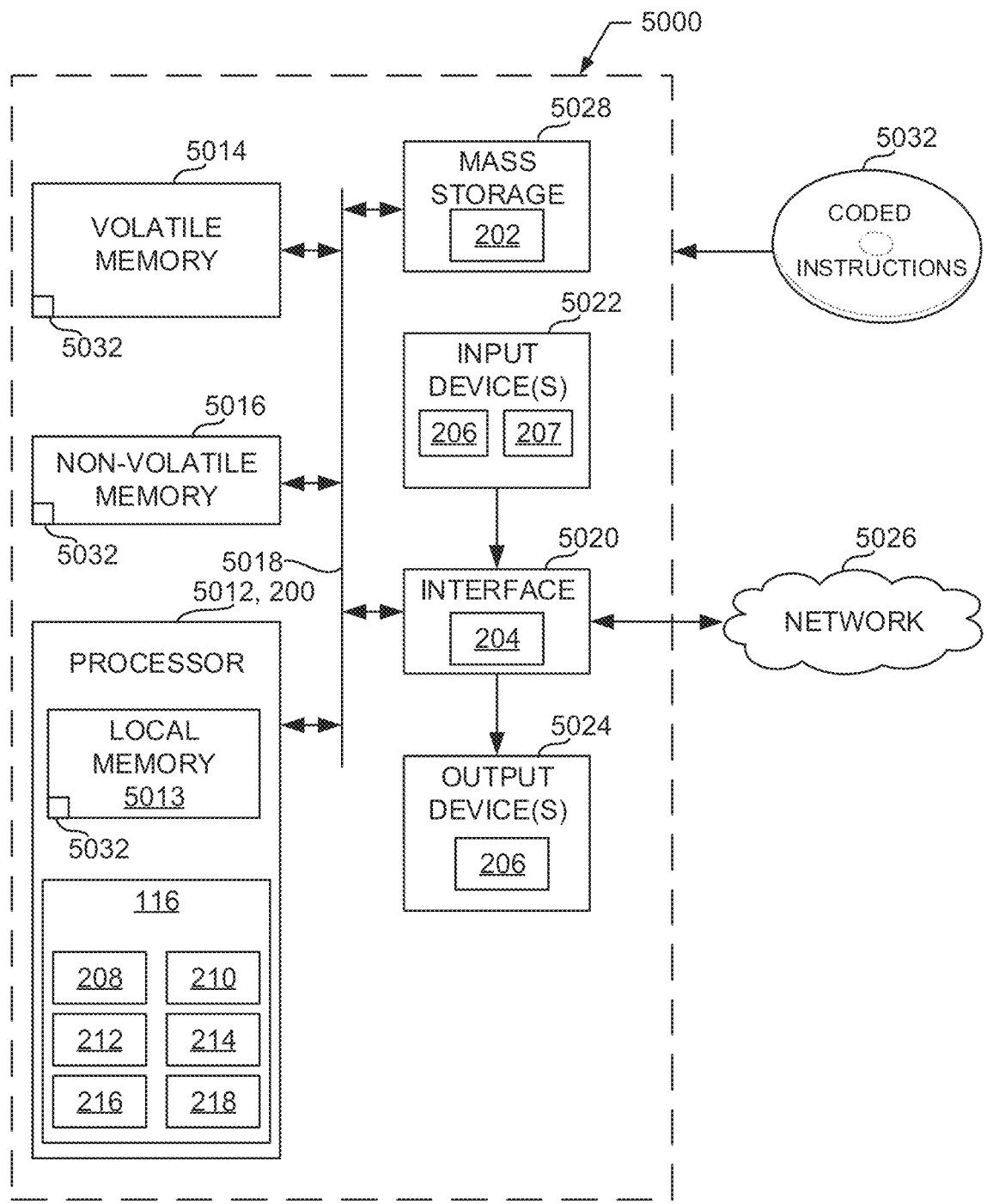
FIG. 50 is a block diagram of an example processing platform structured to execute the instructions of FIGS. 46A and 46B to implement the example user application.

FIG. 50 is a block diagram of an example processor platform 5000 structured to execute the instructions of FIGS. 46A and 46B to implement the user application 116 of FIGS. 1 and 2. The processor platform 5000 can be incorporated into the user device 108. The processor platform 5000 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a personal video recorder, a headset or other wearable device, or any other type of computing device.

The processor platform 5000 of the illustrated example includes a processor 5012. The processor 5012 of the illustrated example is hardware. For example, the processor 5012 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 5012 can represent the processor 200 and implements the example user application 116.

The processor 5012 of the illustrated example includes a local memory 5013 (e.g., a cache). The processor 5012 of the illustrated example is in communication with a main memory including a volatile memory 5014 and a non-volatile memory 5016 via a bus 5018. The volatile memory 5014 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 5016 may be implemented by flash memory and/or any other desired type of memory device. Access to the main memory 5014, 5016 is controlled by a memory controller.

The processor platform 5000 of the illustrated example also includes an interface circuit 5020. The interface circuit 5020 may be implemented by any type of interface standard, such as an Ethernet interface, a universal serial bus (USB), a Bluetooth® interface, a near field communication (NFC) interface, and/or a PCI express interface.

In the illustrated example, one or more input devices 5022 are connected to the interface circuit 5020. The input device(s) 5022 permit(s) a user to enter data and/or commands into the processor 5012. In some examples, the input device(s) 5022 can include the display 206, which may be a touchscreen, and/or the camera 207. Additionally or alternatively, the input device(s) can be implemented by, for example, an audio sensor, a microphone, a keyboard, a button, a mouse, a touchscreen, a track-pad, a trackball, isopoint and/or a voice recognition system.

One or more output devices 5024 are also connected to the interface circuit 5020 of the illustrated example. The output devices 5024 can include the display 206 and can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 5020 of the illustrated example, thus, typically includes a graphics driver card, a graphics driver chip and/or a graphics driver processor.

The interface circuit 5020 of the illustrated example also includes a communication device such as a transmitter, a receiver, a transceiver (e.g., the transceiver 204), a modem, a residential gateway, a wireless access point, and/or a network interface to facilitate exchange of data with external machines (e.g., computing devices of any kind) via a network 5026 (e.g., the network 114, such as the internet). The communication can be via, for example, an Ethernet connection, a digital subscriber line (DSL) connection, a telephone line connection, a coaxial cable system, a satellite system, a line-of-site wireless system, a cellular telephone system, etc.

The processor platform 5000 of the illustrated example also includes one or more mass storage devices 5028 for storing software and/or data. Examples of such mass storage devices 5028 include floppy disk drives, hard drive disks, compact disk drives, Blu-ray disk drives, redundant array of independent disks (RAID) systems, and digital versatile disk (DVD) drives.

The machine executable instructions 5032 of FIGS. 46A and 46B may be stored in the mass storage device 5028, in the volatile memory 5014, in the non-volatile memory 5016, and/or on a removable non-transitory computer readable storage medium such as a CD or DVD. The memory 202 can be implemented by any of the aforementioned.

Figure 51:
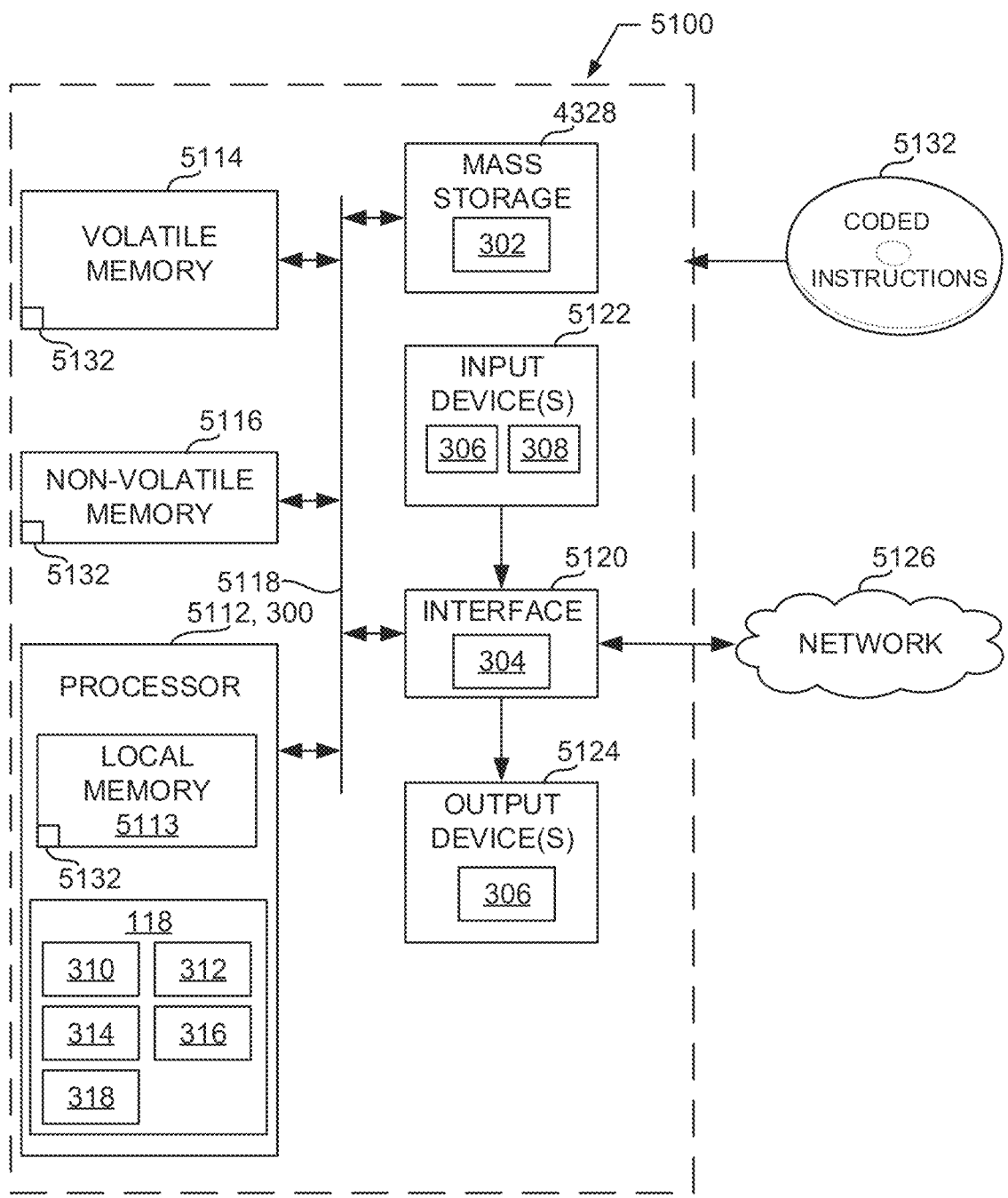
FIG. 51 is a block diagram of an example processing platform structured to execute the instructions of FIG. 47 to implement the example tester application.

FIG. 51 is a block diagram of an example processor platform 5100 structured to execute the instructions of FIG. 47 to implement the tester application 118 of FIGS. 1 and 3. The processor platform 5100 can be incorporated into the tester device 118. The processor platform 5100 can be, for example, a medical instrument (e.g., a laboratory analyzer device) a server, a personal computer, a workstation, a self-learning machine (e.g., a neural network), a mobile device (e.g., a cell phone, a smart phone, a tablet such as an iPad™), a PDA, an Internet appliance, a DVD player, a CD player, a digital video recorder, a Blu-ray player, a personal video recorder, a headset or other wearable device, or any other type of computing device.

The processor platform 5100 of the illustrated example includes a processor 5112. The processor 5112 of the illustrated example is hardware. For example, the processor 5112 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 5112 can represent the processor 300 and implements the example tester application 118.

The processor 5112 of the illustrated example includes a local memory 5113 (e.g., a cache). The processor 5112 of the illustrated example is in communication with a main memory including a volatile memory 5114 and a non-volatile memory 5116 via a bus 5118. The volatile memory 5114 may be implemented by SDRAM, DRAM, RDRAM® and/or any other type of random access memory device. The non-volatile memory 5116 may be implemented by flash memory and/or any other desired type of memory device. Access to the main memory 5114, 5116 is controlled by a memory controller.

The processor platform 5100 of the illustrated example also includes an interface circuit 5120. The interface circuit 5120 may be implemented by any type of interface standard, such as an Ethernet interface, a USB, a Bluetooth® interface, an NFC interface, and/or a PCI express interface.

In the illustrated example, one or more input devices 5122 are connected to the interface circuit 5120. The input device(s) 5122 permit(s) a user to enter data and/or commands into the processor 5112. In some examples, the input device(s) 5122 can include the display 306, which may be a touchscreen, and/or the camera 308. Additionally or alternatively, the input device(s) can be implemented by, for example, an audio sensor, a microphone, a keyboard, a button, a mouse, a track-pad, a trackball, isopoint and/or a voice recognition system.

One or more output devices 5124 are also connected to the interface circuit 5120 of the illustrated example. The output devices 5124 can include the display 306 and can be implemented, for example, by display devices (e.g., an LED, an OLED, an LCD display, a CRT display, an IPS display, a touchscreen, etc.), a tactile output device, a printer and/or speaker. The interface circuit 5120 of the illustrated example, thus, typically includes a graphics driver card, a graphics driver chip and/or a graphics driver processor.

The interface circuit 5120 of the illustrated example also includes a communication device such as a transmitter, a receiver, a transceiver (e.g., the transceiver 304), a modem, a residential gateway, a wireless access point, and/or a network interface to facilitate exchange of data with external machines (e.g., computing devices of any kind) via a network 5126 (e.g., the network 114, such as the internet). The communication can be via, for example, an Ethernet connection, a DSL connection, a telephone line connection, a coaxial cable system, a satellite system, a line-of-site wireless system, a cellular telephone system, etc.

The processor platform 5100 of the illustrated example also includes one or more mass storage devices 5128 for storing software and/or data. Examples of such mass storage devices 5128 include floppy disk drives, hard drive disks, compact disk drives, Blu-ray disk drives, RAID systems, and DVD drives.

The machine executable instructions 5132 of FIG. 47 may be stored in the mass storage device 5128, in the volatile memory 5114, in the non-volatile memory 5116, and/or on a removable non-transitory computer readable storage medium such as a CD or DVD. The memory 302 can be implemented by any of the aforementioned.

Figure 52:
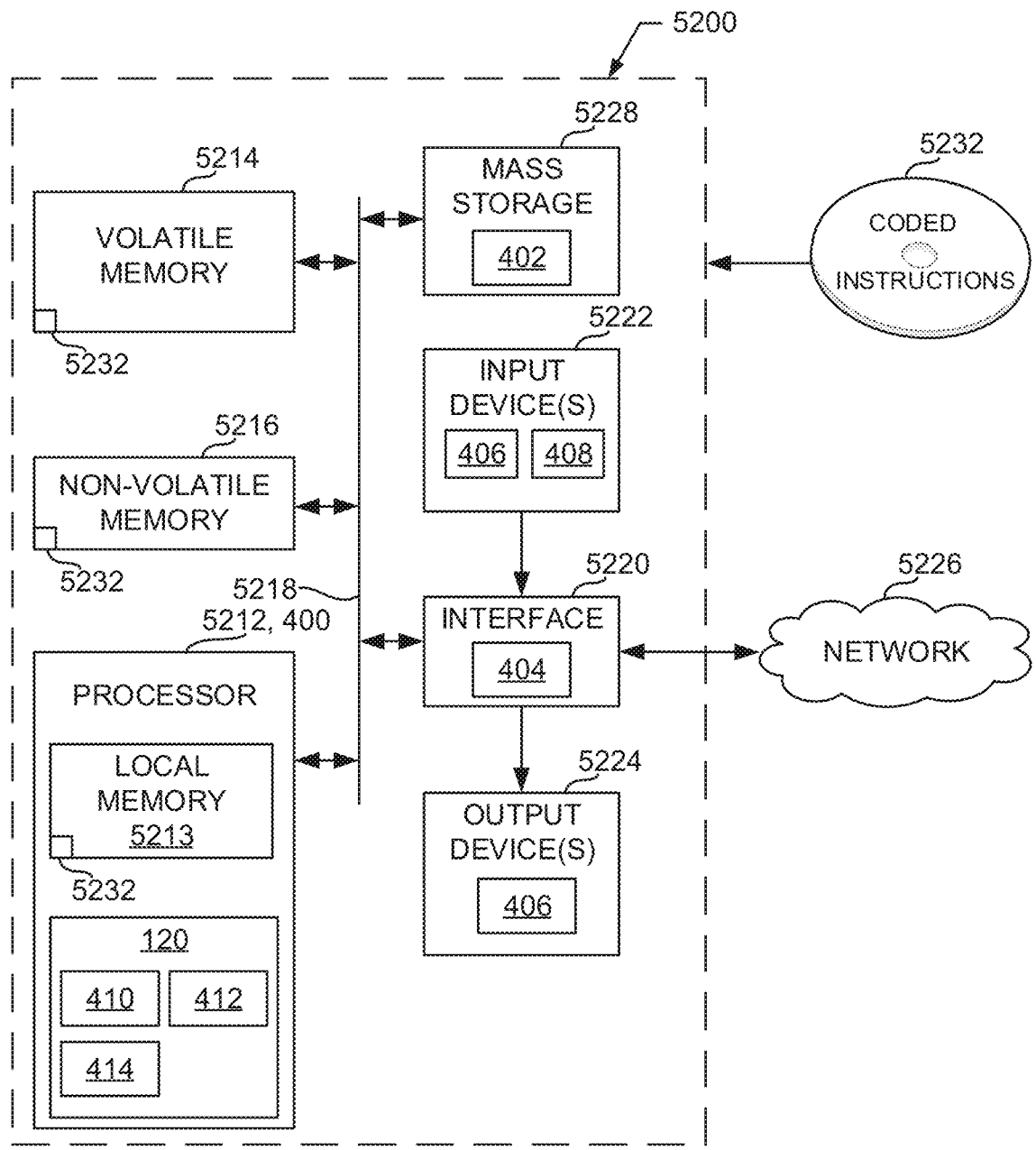
FIG. 52 is a block diagram of an example processing platform structured to execute the instructions of FIG. 48 to implement the example verifier application.

FIG. 52 is a block diagram of an example processor platform 5200 structured to execute the instructions of FIG. 48 to implement the verifier application 120 of FIGS. 1 and 4. The processor platform 5200 incorporated into the verifier device 112. The processor platform 5200 can be can be, for example, a server, a handheld code scanner, a personal computer, a workstation, a self-learning machine (e.g., a neural network), a mobile device (e.g., a cell phone, a smart phone, a tablet such as an iPad™), a PDA, an Internet appliance, a DVD player, a CD player, a digital video recorder, a Blu-ray player, a personal video recorder, a headset or other wearable device, or any other type of computing device.

The processor platform 5200 of the illustrated example includes a processor 5212. The processor 5212 of the illustrated example is hardware. For example, the processor 5212 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 5212 can represent the processor 400 and implements the example verifier application 120.

The processor 5212 of the illustrated example includes a local memory 4413 (e.g., a cache). The processor 5212 of the illustrated example is in communication with a main memory including a volatile memory 5214 and a non-volatile memory 5216 via a bus 5218. The volatile memory 5214 may be implemented by SDRAM, DRAM, RDRAM® and/or any other type of random access memory device. The non-volatile memory 5216 may be implemented by flash memory and/or any other desired type of memory device. Access to the main memory 5214, 5216 is controlled by a memory controller.

The processor platform 5200 of the illustrated example also includes an interface circuit 5220. The interface circuit 5220 may be implemented by any type of interface standard, such as an Ethernet interface, a USB, a Bluetooth® interface, an NFC interface, and/or a PCI express interface.

In the illustrated example, one or more input devices 5222 are connected to the interface circuit 5220. The input device(s) 5222 permit(s) a user to enter data and/or commands into the processor 5212. In some examples, the input device(s) 5222 can include the display 406, which may be a touchscreen, and/or the camera 408. Additionally or alternatively, the input device(s) can be implemented by, for example, an audio sensor, a microphone, a keyboard, a button, a mouse, a track-pad, a trackball, isopoint and/or a voice recognition system.

One or more output devices 5224 are also connected to the interface circuit 5220 of the illustrated example. The output devices 5224 can include the display 406 and can be implemented, for example, by display devices (e.g., an LED, an OLED, an LCD display, a CRT display, an IPS display, a touchscreen, etc.), a tactile output device, a printer and/or speaker. The interface circuit 5220 of the illustrated example, thus, typically includes a graphics driver card, a graphics driver chip and/or a graphics driver processor.

The interface circuit 5220 of the illustrated example also includes a communication device such as a transmitter, a receiver, a transceiver (e.g., the transceiver 404), a modem, a residential gateway, a wireless access point, and/or a network interface to facilitate exchange of data with external machines (e.g., computing devices of any kind) via a network 5226 (e.g., the network 114, such as the internet). The communication can be via, for example, an Ethernet connection, a DSL connection, a telephone line connection, a coaxial cable system, a satellite system, a line-of-site wireless system, a cellular telephone system, etc.

The processor platform 5200 of the illustrated example also includes one or more mass storage devices 5228 for storing software and/or data. Examples of such mass storage devices 5228 include floppy disk drives, hard drive disks, compact disk drives, Blu-ray disk drives, RAID systems, and DVD drives.

The machine executable instructions 5232 of FIG. 48 may be stored in the mass storage device 5228, in the volatile memory 5214, in the non-volatile memory 5216, and/or on a removable non-transitory computer readable storage medium such as a CD or DVD. The memory 402 can be implemented by any of the aforementioned.

Figure 53:
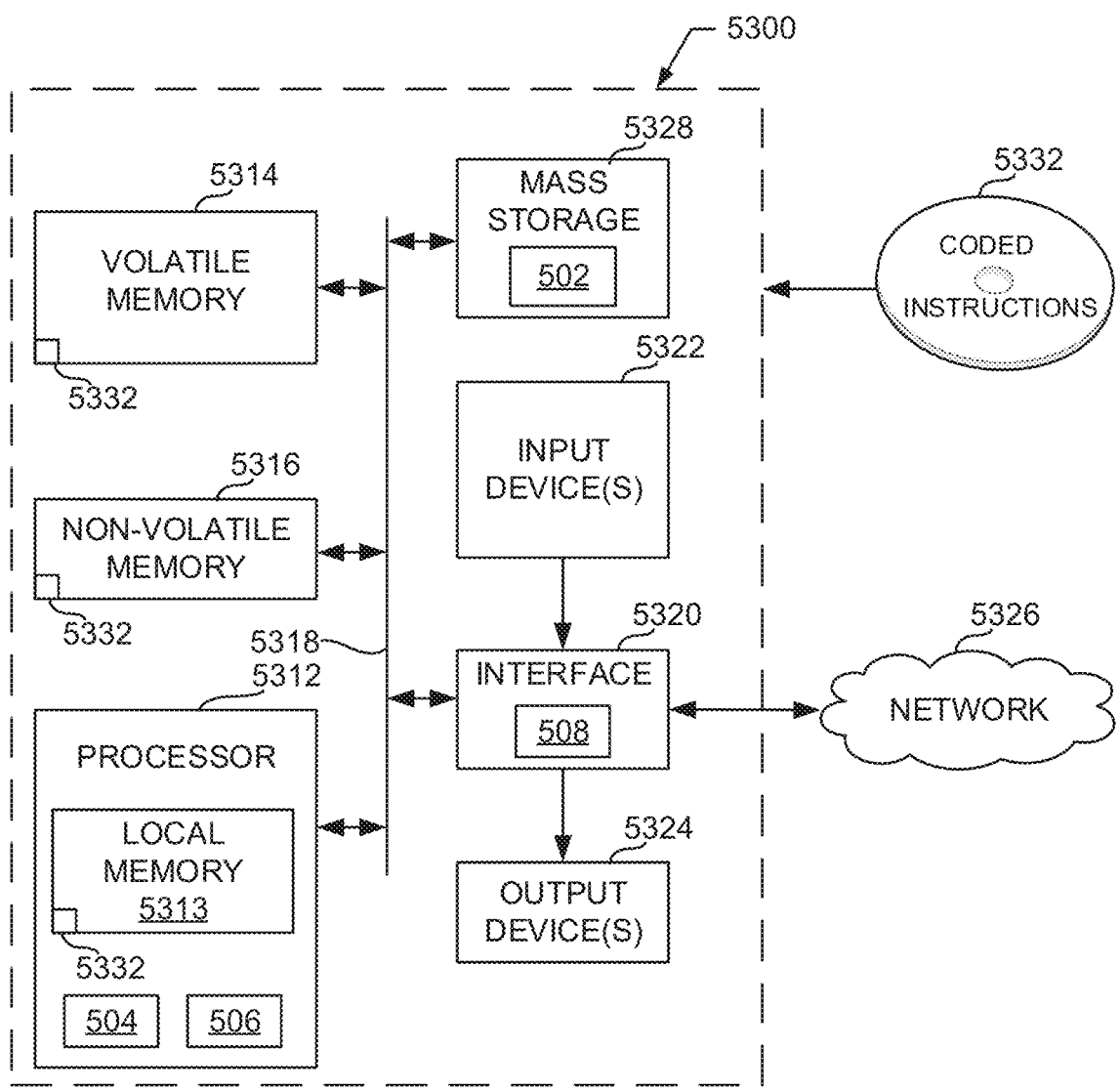
FIG. 53 is a block diagram of an example processing platform structured to execute the instructions of FIG. 49 to implement the digital pass management system.

FIG. 53 is a block diagram of an example processor platform 5300 structured to execute the instructions of FIG. 49 to implement the digital pass management system 100 of FIGS. 1 and 5. The processor platform 5300 can be, for example, a server, a personal computer, a workstation, a self-learning machine (e.g., a neural network), a mobile device (e.g., a cell phone, a smart phone, a tablet such as an iPad™), a PDA, an Internet appliance, a DVD player, a CD player, a digital video recorder, a Blu-ray player, a personal video recorder, a headset or other wearable device, or any other type of computing device.

The processor platform 5300 of the illustrated example includes a processor 5312. The processor 5312 of the illustrated example is hardware. For example, the processor 5312 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 5312 can implement the example record generator 504 and the example validator 506.

The processor 5312 of the illustrated example includes a local memory 5313 (e.g., a cache). The processor 5312 of the illustrated example is in communication with a main memory including a volatile memory 5314 and a non-volatile memory 5316 via a bus 5318. The volatile memory 5314 may be implemented by SDRAM, DRAM, RDRAM® and/or any other type of random access memory device. The non-volatile memory 5316 may be implemented by flash memory and/or any other desired type of memory device. Access to the main memory 5314, 5316 is controlled by a memory controller.

The processor platform 5300 of the illustrated example also includes an interface circuit 5320. The interface circuit 5320 may be implemented by any type of interface standard, such as an Ethernet interface, a USB, a Bluetooth® interface, an NFC interface, and/or a PCI express interface.

In the illustrated example, one or more input devices 5322 are connected to the interface circuit 5320. The input device(s) 5322 permit(s) a user to enter data and/or commands into the processor 5312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 5324 are also connected to the interface circuit 5320 of the illustrated example. The output devices 5324 can be implemented, for example, by display devices (e.g., an LED, an OLED, an LCD display, a CRT display, an IPS display, a touchscreen, etc.), a tactile output device, a printer and/or speaker. The interface circuit 5320 of the illustrated example, thus, typically includes a graphics driver card, a graphics driver chip and/or a graphics driver processor.

The interface circuit 5320 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 5326 (e.g., the network 114, such as the internet). The communication can be via, for example, an Ethernet connection, a DSL connection, a telephone line connection, a coaxial cable system, a satellite system, a line-of-site wireless system, a cellular telephone system, etc.

The processor platform 5300 of the illustrated example also includes one or more mass storage devices 5328 for storing software and/or data. Examples of such mass storage devices 5328 include floppy disk drives, hard drive disks, compact disk drives, Blu-ray disk drives, RAID systems, and DVD drives.

The machine executable instructions 5332 of FIG. 49 may be stored in the mass storage device 5328, in the volatile memory 5314, in the non-volatile memory 5316, and/or on a removable non-transitory computer readable storage medium such as a CD or DVD. The database 502 can be implemented by any of the aforementioned.

Figure 54:
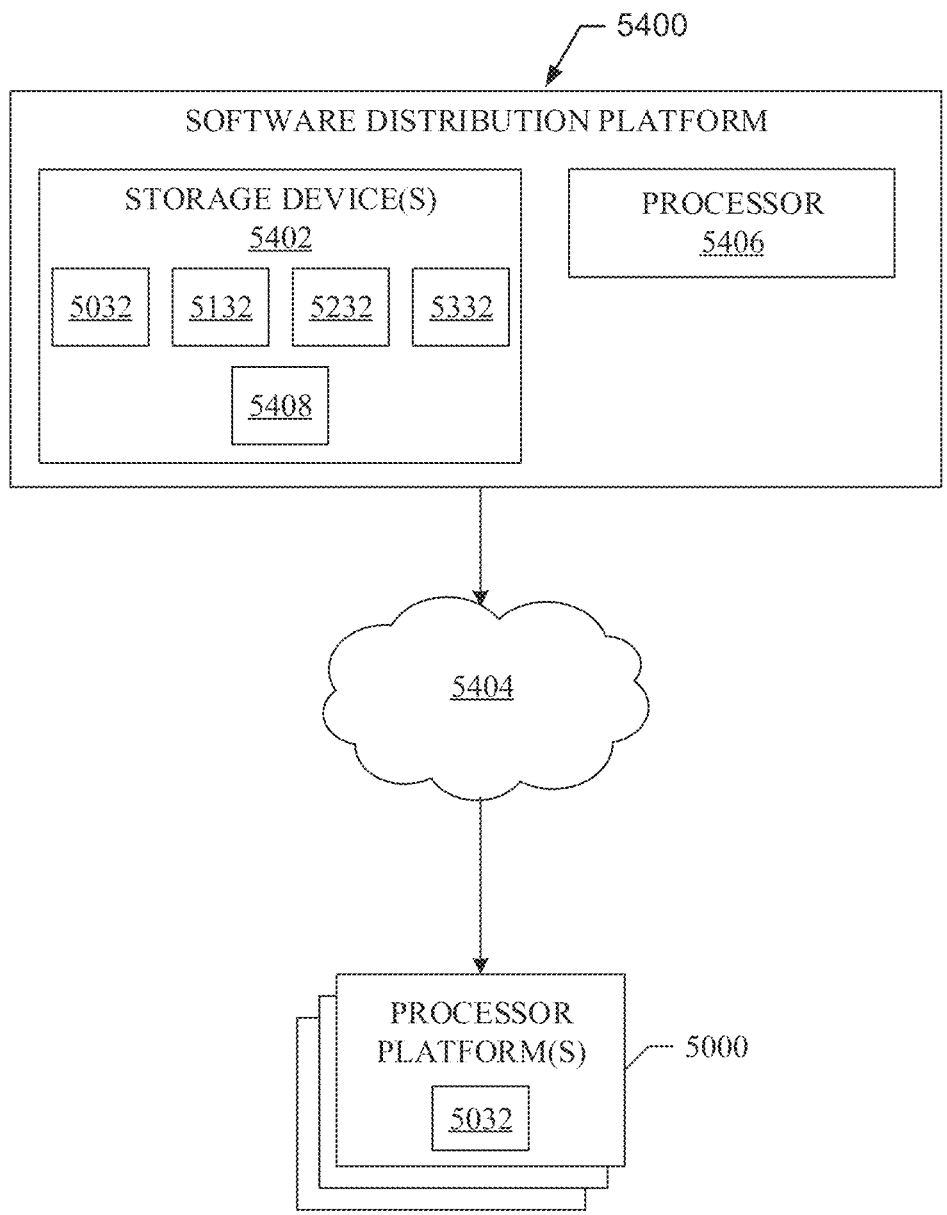
FIG. 54 is a block diagram of an example software distribution platform to distribute software (e.g., software corresponding to the example computer readable instructions of FIGS. 46A, 46B, 47, 48, and 49) to client devices such as consumers (e.g., for license, sale and/or use), retailers (e.g., for sale, re-sale, license, and/or sub-license), and/or original equipment manufacturers (OEMs) (e.g., for inclusion in products to be distributed to, for example, retailers and/or to direct buy customers).

A block diagram illustrating an example software distribution platform 5400 to distribute software such as the example computer readable instructions 5032, 5132, 5232, and 5332 of FIGS. 50-53 to third parties is illustrated in FIG. 54. The example software distribution platform 5400 may be implemented by any computer server, data facility, cloud service, etc., capable of storing and transmitting software to other computing devices. The third parties may be customers, employees, patients, clients of the entity owning and/or operating the software distribution platform. For example, the entity that owns and/or operates the software distribution platform may be a developer, a seller, and/or a licensor of software such as the example computer readable instructions 5032, 5132, 5232, and 5332 of FIGS. 50-53. The third parties may be consumers, users, retailers, OEMs, etc., who purchase and/or license the software for use and/or re-sale and/or sub-licensing.

In the illustrated example, the software distribution platform 5400 includes (or is implemented by) one or more servers to distribute the example computer readable instructions 5032, 5132, 5232, and 5332 to the corresponding processor platforms 5000, 5100, 5200, and 5300 of FIGS. 50-53. The one or more servers include one or more storage devices 5402. The storage devices 5402 can be one or more non-transitory computer readable medium. The storage devices 5402 store the computer readable instructions, which may correspond to the example computer readable instructions 5032, 5132, 5232, and 5332 of FIGS. 50-53, as described above. The one or more servers of the example software distribution platform 5400 are in communication with a network 5404, which may correspond to any one or more of the Internet and/or any of the example networks described above. The one or more servers also include at least one processor 5406. The storage device 5402 stores instructions 5408 that, when executed by the at least one processor 5406, cause the at least one or processor 5406 to transmit and/or otherwise distribute the example computer readable instructions 5032, 5132, 5232, and 5332 of FIGS. 50-53 over the network 5404. In some examples, the one or more servers are responsive to requests to transmit the software to a requesting party as part of a commercial transaction. Payment for the delivery, sale and/or license of the software may be handled by the one or more servers of the software distribution platform and/or via a third party payment entity. The servers enable purchasers and/or licensors to download the computer readable instructions 5032, 5132, 5232, and 5332 from the software distribution platform 5400. For example, the software, which may correspond to the example computer readable instructions 5032, 5132, 5232, and 5332 of FIGS. 50-53, may be downloaded to the example respective processor platforms 5000, 5100, 5200, 5300, which is to execute the computer readable instructions 5032, 5132, 5232, 5332 to implement the user application 116, the tester application 118, the verifier application 120, and/or the digital pass management system 100. In some example, one or more servers of the software distribution platform 5405 periodically offer, transmit, and/or force updates to the software (e.g., the example computer readable instructions 5032, 5132, 5232, and 5332 of FIGS. 50-53) to ensure improvements, patches, updates, etc. are distributed and applied to the software at the end user devices.

From the foregoing, it will be appreciated that example methods, apparatus, systems, and articles of manufacture have been disclosed that enable verifiers to quickly, easily, and accurately verify whether a user (e.g., an employee, a passenger, a spectator, a patient, or other person) has recently tested negative for an infectious diseases before allowing the person access to a particular area or location. As such, the examples, disclosed herein can help reduce the risk of spreading an infectious disease and, thus, improve safety.

The examples disclosed herein also increase communication bandwidth among the user application 116, the tester application 118, the verifier application 120, and the digital pass management system 100 because the digital passes are produced on the user device 108 and do not have to be transmitted over the Internet or computed in the cloud. Furthermore, the user application 116 constructs the digital pass based on a negative result. Therefore, user devices do not expend operating resources to construct a digital pass for every test that is performed.

In some examples, the verifier application 120 communicates directly with the digital pass management system 100. In such examples, the verifier 106 may receive test results without communication with a user. For example, an employer may receive an employee's test result before an employee arrives at work. In this example, the employer may preemptively contact the employee and notify them that they have been restricted from attendance at work.

In some examples, the tester 104 and/or the digital pass management system 100 develop a sequence of tests to recommend to a user. For example, the sequence of tests may be based on a pathogen life cycle and/immune response. In such examples, a first type of test may be recommended at a first time period. Based on an incubation period, the pathogen life cycle, and/or immune response, a second instance of the first type of test and/or a second type of test may be recommended at a second time period. The tester 104 and/or the digital pass management system 100 can transmit a notification of the sequence of diagnostic tests to the user device 108. The scheduler 208 of the user application 116 causes the user device 108 to display the notification of the recommended testing sequence.

In some examples, the tester 104 and/or the digital pass management system 100 may publish test results. In some examples, geographic data regarding where digital pass codes have been scanned is gathered. In some examples, geographic data regarding where positive tests have occurred (e.g., user residential and work data is gathered. The user application 116, the tester application 118, the verifier application 120, and the digital pass management system 100 may work in concert to aggregate geographic data related to positive tests, negative tests, user travel history, and user movement. The aggregated data may be used to create heat maps that identify regions or smaller geographic locations (e.g., a particular school or business) that are areas of relatively higher positivity rates.

Example digital pass verification systems, methods, apparatus, devices, and articles of manufacture are disclosed herein. Further examples and combinations thereof include the following:

Example 1 includes one or more servers to distribute first instructions, second instructions, third instructions, and fourth instructions, on a network. The one or more servers include at least one storage device including fifth instructions and at least one processor to execute the fifth instructions to transmit the first instructions, the second instructions, the third instructions, and the fourth instructions over the network. The first instructions, when executed, cause a first device carried by a person to at least: access a result of a diagnostic test performed on the person, the result provided by a second device; generate a machine-readable code in response to the result being negative; and display the machine-readable code on a display of the first device to enable the person to gain access to a location. The second instructions, when executed, cause the second device to at least: receive input indicative of the result of the diagnostic test; and transmit the result to a third device. The third instructions, when executed, cause a fourth device to at least: detect the machine-readable code from the first device;

determine a user identification associated with the person based on the machine-readable code; determine a test identification associated with the diagnostic test based on the machine-readable code; transmit the user identification and the test identification to the third device, the third device remote from the fourth device; and receive a verification outcome from the third device. The fourth instructions, when executed, cause the third device to at least: transmit the result of the diagnostic test to the first device; receive the user identification and the test identification from the fourth device; verify the result of the diagnostic test based on the user identification and the test identification; determine a number of days since the diagnostic test; and transmit the verification outcome to the fourth device. The verification outcome includes a first notice when the result of the diagnostic test is negative and the number of days since the diagnostic test is below a threshold number of days, and the verification outcome includes a second notice when the number of days since the diagnostic test is greater than the threshold.

Example 2 includes the one or more servers of Example 1, wherein the result is a first result, the diagnostic test is a first diagnostic test, and the machine-readable code is a first machine-readable code. The first instructions, when executed, cause the first device to: access a second result of a second diagnostic test performed on the person; and generate a second machine-readable code in response to the second result being negative.

Example 3 includes the one or more servers of Example 2, wherein the first diagnostic test is to detect a presence or an absence of a first analyte of interest, and the second diagnostic test is to detect a presence or an absence of a second analyte of interest. The second analyte of interest is different than the first analyte of interest.

Example 4 includes the one or more servers of Example 2, wherein the first diagnostic test is to detect a presence or an absence of an analyte of interest, and the second diagnostic test is to detect a presence or an absence of the analyte of interest. The second diagnostic test performed is subsequent to the first diagnostic test.

Example 5 includes the one or more servers of any of Examples 2-4, wherein the second diagnostic test is a different type of diagnostic test than the first diagnostic test.

Example 6 includes the one or more servers of Example 5, wherein the first diagnostic test is an antigen test and the second diagnostic test is an antibody test.

Example 7 includes the one or more servers of an of Examples 2-6, wherein the first diagnostic test is to be performed with a first type of testing equipment and the second diagnostic test is to be performed with a second type of testing equipment. The second type is different than the first type.

Example 8 includes the one or more servers of any of Examples 2-7, wherein the second machine-readable code is to be read by a fifth device. The fifth device is remote from the third device.

Example 9 includes the one or more servers of any of Examples 1-8, wherein the fourth instructions, when executed, enable the third device to invalidate the machine-readable code when the number of days since the diagnostic test is below the threshold number of days.

Example 10 includes the one or more servers of any of Examples 1-9, wherein the diagnostic test is to detect a presence or an absence of a pathogen and the threshold is based on an incubation period of the pathogen.

Example 11 includes the one or more servers of any of Examples 1-10, wherein the diagnostic test is a first diagnostic test, and the first instructions, when executed, cause the first device to display a notification to the person to schedule a second diagnostic test based on the number of days since the first diagnostic test and the threshold number of days.

Example 12 includes the one or more servers of any of Examples 1-11, wherein the third instructions, when executed, cause the fourth device to display the first notice or the second notice to grant or deny the person access to the location based on the verification outcome and a location of the fourth device.

Example 13 includes the one or more servers of any of Examples 1-12, wherein the third instructions, when executed, cause the fourth device to display the first notice or the second notice to grant or deny the person access to the location based on the verification outcome and at least one of a time of day or a day of the week.

Example 14 includes the one or more servers of any of Examples 1-13, wherein the third instructions, when executed, cause the fourth device to automatically unlock at least one of a door, a gate, or a turnstile based on the verification outcome.

Example 15 includes the one or more servers of any of Examples 1-14, wherein the fourth instructions, when executed, cause the third device to: develop a sequence of diagnostic tests based on at least one of a pathogen incubation period, a pathogen life cycle, or an immune response; and transmit a notification of the sequence of diagnostic tests to the first device. The first instructions, when executed, cause the first device to display the notification of the sequence of diagnostic tests to the person on the first device.

Example 16 includes one or more non-transitory computer readable medium including instructions that, when executed, cause one or more processors in a first device carried by a person to at least: access a result of a diagnostic test performed on the person; generate a machine-readable code in response to the result being negative; and display the machine-readable code on a display of the first device to enable the person to gain access to a location. The instructions, when executed, cause one or more processors in a second device to at least: detect the machine-readable code from the first device; determine a user identification associated with the person based on the machine-readable code; determine a test identification associated with the diagnostic test based on the machine-readable code; transmit the user identification and the test identification to a third device, the third device remote from the second device; and receive a verification outcome from the third device. The instructions, when executed, cause one or more processors in the third device to at least: transmit the result of the diagnostic test to the first device; receive the user identification and the test identification from the second device; verify the result of the diagnostic test based on the user identification and the test identification; determine a number of days since the diagnostic test; and transmit the verification outcome to the second device. The verification outcome includes a first notice when the result of the diagnostic test is negative and the number of days since the diagnostic test is below a threshold number of days, and the verification outcome includes a second notice when the number of days since the diagnostic test is greater than the threshold.

Example 17 includes the one or more non-transitory computer readable medium of Example 16, wherein the instructions, when executed, cause one or more processors in a fourth device to at least: automatically determine the result of the diagnostic test; and transmit the result of the diagnostic test to the third device.

Example 18 includes the one or more non-transitory computer readable medium of Examples 16 or 17, wherein the instructions, when executed, cause one or more processors in a fourth device to at least: provide a notification for the interpretation and entry of the result of the diagnostic test; and transmit the result of the diagnostic test to the third device.

Example 19 includes the one or more non-transitory computer readable medium of an of Examples 16-18, wherein the instructions, when executed, cause one or more processors in a fourth device to transmit an image of at least a portion of a test kit used in the diagnostic test to the first device.

Example 20 includes the one or more non-transitory computer readable medium of any of Examples 16-19, wherein the instructions cause the one or more processors of the second device to display the first notice or the second notice to grant or deny the person access to the location based on the verification outcome and at least one of: a location of the second device, a time of day, a day of the week, or an employment status.

Example 21 includes a server to distribute first instructions on a network. The server includes at least one storage device including second instructions and at least one processor to execute the second instructions to transmit the first instructions over the network. The first instructions, when executed, are to cause a mobile device carried by a person to at least: access a user identification associated with the person; access a result of a diagnostic test performed on a sample gathered from the person; display the result on a display of the mobile device; and generate an interface including the user identification and an indicator. The indicator is generated in response to the result being negative and a number of days since the diagnostic test being below a threshold number of days. The first instructions, when executed, are also to cause the mobile device to display the interface on the display to enable the person to gain entry into a location.

Example 22 includes the server of Example 21, wherein the result is a first result, the diagnostic test is a first diagnostic test, the interface is a first interface, and the indicator is a first indicator. The first instructions, when executed, cause the mobile device to: access a second result of a second diagnostic test; display the second result on the display of the mobile device; and generate a second interface including a second indicator. The second indicator is generated in response to the second result being negative and a number of days since the second diagnostic test being below the threshold number of days.

Example 23 includes the server of Example 22, wherein the person is a first person and the second diagnostic test is performed on a second person.

Example 24 includes the server of any of Examples 21-23, wherein the diagnostic test is to detect a presence or an absence of a pathogen and the threshold number of days is based on an incubation period of the pathogen.

Example 25 includes the server of any of Examples 21-24, wherein the diagnostic test is a first diagnostic test, and the first instructions, when executed, cause the mobile device to display a notification to the person to schedule a second diagnostic test based on the number of days since the diagnostic test and the threshold number of days.

Example 26 includes the server of any of Examples 21-25, wherein the first instructions, when executed, cause the mobile device to inform the person how to collect the sample for the diagnostic test.

Example 27 includes the server of any of Examples 21-26, wherein the first instructions, when executed, cause the mobile device to detect and interpret a test kit code on a test kit to obtain a test kit identification associated with the test kit.

Example 28 includes the server of any of Examples 21-27, wherein the first instructions, when executed, cause the mobile device to provide a notification for interpretation and entry of the result of the diagnostic test.

Example 29 includes the server of any of Examples 21-28, wherein the first instructions, when executed, enable the person to schedule an appointment to provide the sample for the diagnostic test.

Example 30 includes the server of any of Examples 21-29, wherein the first instructions, when executed, cause the mobile device to electronically connect with a telehealth service provider prior to collection of the sample.

Example 31 includes at least one non-transitory computer readable medium including instructions that, when downloaded to a mobile device and executed, cause a processor of the mobile device to at least: access a result of a diagnostic test performed on a sample gathered from a person; generate a machine-readable code in response to the result being negative; and display the machine-readable code on a display of the mobile device to enable the person to gain entry into a location.

Example 32 includes the at least one non-transitory computer readable medium of Example 31, wherein the machine-readable code includes a user identification and a test kit identification associated with a test kit used to perform the diagnostic test.

Example 33 includes the at least one non-transitory computer readable medium of Examples 31 or 32, wherein the result is a first result, the diagnostic test is a first diagnostic test, the sample is a first sample, and the machine-readable code is a first machine-readable code. The instructions, when executed, cause the processor of the mobile device to: access a second result of a second diagnostic test performed on a second sample gathered from the person; and generate a second machine-readable code in response to the second result being negative.

Example 34 includes the at least one non-transitory computer readable medium of Example 33, wherein the first diagnostic test is to detect a presence or an absence of a first analyte of interest, and the second diagnostic test is to detect a presence or an absence of a second analyte of interest. The second analyte of interest is different than the first analyte of interest.

Example 35 includes the at least one non-transitory computer readable medium of Example 33, wherein the first diagnostic test is to detect a presence or an absence of an analyte of interest, and the second diagnostic test is to detect a presence or an absence of the analyte of interest. The second diagnostic test is performed subsequent to the first diagnostic test.

Example 36 includes the at least one non-transitory computer readable medium of Example 36, wherein the first diagnostic test is an antigen test and the second diagnostic test is an antibody test.

Example 37 includes the at least one non-transitory computer readable medium of any of Examples 31-36, wherein the instructions, when executed, cause the processor of the mobile device to: receive a notification of a sequence of diagnostic tests based on at least one of a pathogen incubation period, a pathogen life cycle, or an immune response; and display the notification of the sequence of diagnostic tests to the person on the display of the mobile device.

Example 38 includes the at least one non-transitory computer readable medium of any of Examples 31-37, wherein the instructions, when executed, cause the processor of the mobile device to electronically connect with a telehealth service provider prior to collection of the sample.

Example 39 includes the at least one non-transitory storage medium of any of Examples 31-38, wherein the instructions, when executed, cause the processor of the mobile device to: inform the person how to collect the sample for the diagnostic test; and automatically determine the result of the diagnostic test.

Example 40 includes the at least one non-transitory computer readable medium of any of Examples 31-39, wherein the instructions, when executed, cause the processor of the mobile device to: inform the person how to collect the sample for the diagnostic test; and provide a notification for interpretation and entry of the result of the diagnostic test into the mobile device.

Example 41 includes an apparatus including processor circuitry and memory including instructions which, when executed, cause the processor circuitry to: access a result of a diagnostic test associated with a test kit identification; associate the result of the diagnostic test with a user identification; transmit the result of the diagnostic test and the test kit identification to a first device to cause the first device to generate a machine-readable pass on a display of the first device; receive the user identification and the test kit identification from a second device that is communicatively coupled to a scanner of the second device when the scanner reads the machine-readable pass, and, when the test kit identification and the user identification match the result of the diagnostic test: transmit a first notification to the second device when a number of days since the diagnostic test is less than a threshold number of days to cause the second device to present a first display; and transmit a second notification to the second device when the number of days since the diagnostic test is greater than the threshold number of days to cause the second device to present a second display, the second display different from the first display.

Example 42 includes the apparatus of Example 41, wherein the instructions, when executed, cause the processor circuitry to transmit the second notification to the second device when the user identification has been inactivated from a verifier organization associated with the second device.

Example 43 includes the apparatus of Examples 41 or 42, wherein the instructions, when executed, cause the processor circuitry to transmit a third notification to the second device when at least one of the user identification or the test kit identification is not matched to the result to cause the second device to present a third display. The third display is different from the first display and the second display.

Example 44 includes the apparatus of any of Examples 41-43, wherein the instructions, when executed, cause the processor circuitry to receive the result of the diagnostic test from the first device.

Example 45 includes the apparatus of any of Examples 41-44, wherein the instructions, when executed, cause the processor circuitry to receive the result of the diagnostic test from a third device, the third device remote from the first device and the second device.

Example 46 includes the apparatus of any of Examples 41-45, wherein the threshold number of days is set by a verifier organization associated with the second device.

Example 47 includes the apparatus of any of Examples 41-46, wherein the threshold number of days is based on a biological characteristic of an analyte of interest to be tested in the diagnostic test.

Example 48 includes the apparatus of any of Examples 41-47, wherein the instructions, when executed, cause the processor circuitry to: access results of diagnostic tests; receive sets of user identifications and test kit identifications from one or more second devices; generate a report based on the results and receipt of the sets of user identifications and test kit identifications; and transmit the report to a government agency.

Example 49 includes the apparatus of any of Examples 41-48, wherein the instructions, when executed, cause the processor circuitry to verify at least one of an expiration date of a test kit or a recall status of the test kit based on the test kit identification prior to transmitting the result of the diagnostic test and the test kit identification to the first device.

Example 50 includes the apparatus of any of Examples 41-49, wherein the instructions, when executed, cause the processor circuitry to verify an authenticity of a test kit based on the test kit identification prior to transmitting the result of the diagnostic test and the test kit identification to the first device.

Example 51 includes at least one non-transitory storage medium including instructions that, when executed, cause a machine to: access a result of a diagnostic test associated with a test kit identification; associate the result of the diagnostic test with a user identification; transmit the result of the diagnostic test and the test kit identification to a first device to cause the first device to generate a digital pass code on a display of the first device; receive the user identification and the test kit identification from a second device that is communicatively coupled to a scanner of the second device when the scanner reads the digital pass code; and, when the test kit identification and the user identification match the result of the diagnostic test: transmit a first notification to the second device when an amount of time since the diagnostic test is below a threshold amount of time to cause the second device to present a first display; and transmit a second notification to the second device when the amount of time since the diagnostic test is greater than the threshold amount of time to cause the second device to present a second display, the second display different from the first display.

Example 52 includes the storage medium of Example 51, wherein the instructions, when executed, cause the machine to transmit the second notification to the second device when the user identification has been removed from a verifier organization associated with the second device.

Example 53 includes the storage medium of Examples 51 or 52, wherein the instructions, when executed, cause the machine to transmit a third notification to the second device when at least one of the user identification or the test kit identification is not matched to the result to cause the second device to present a third display. The third display is different from the first display and the second display.

Example 54 includes the storage medium of any of Examples 51-53, wherein the instructions, when executed, cause the machine to receive the result of the diagnostic test from the first device.

Example 55 includes the storage medium of any of Examples 51-54, wherein the instructions, when executed, cause the machine to receive the result of the diagnostic test from a third device, the third device remote from the first device and the second device.

Example 56 includes the storage medium of any of Examples 51-55, wherein the threshold amount of time is set by a verifier organization associated with the second device.

Example 57 includes the storage medium of any of Examples 51-56, wherein the threshold amount of time is based on a biological characteristic of an analyte of interest to be tested in the diagnostic test.

Example 58 includes the storage medium of any of Examples 51-57, wherein the instructions, when executed, cause the machine to: access results of diagnostic tests; receive sets of user identifications and test kit identifications from one or more second devices; generate a report based on the results and receipt of the sets of user identifications and test kit identifications; and transmit the report to a government agency.

Example 59 includes the storage medium of any of Examples 51-58, wherein the instructions, when executed, cause the machine to verify at least one of an expiration date of a test kit or a recall status of the test kit based on the test kit identification prior to transmitting the result of the diagnostic test and the test kit identification to the first device.

Example 60 includes the storage medium of any of Examples 51-59, wherein the instructions, when executed, cause the machine to verify an authenticity of a test kit based on the test kit identification prior to transmitting the result of the diagnostic test and the test kit identification to the first device.

Example 61 is a device to generate a digital pass. The device includes an analyzer to determine a result of a diagnostic test and a code generator to: access a test identification based on the result, access a user identification based on the result, construct a machine-readable code based on the test identification and the user identification, and incorporate the code into a digital pass. The device further includes an output to display the digital pass.

Example 62 includes the device of Example 61, wherein the code generator is to incorporate an expiration date into the digital pass. The device further includes a scheduler to determine a validity of the digital pass based on the expiration date, and a notifier to prompt scheduling of a test when the time comparator determines the digital pass is not valid.

Example 63 is a device to generate a digital pass. The device includes means for determining a result of a diagnostic test, means for generating a code, the generating means to: access a test identification based on the result, access a user identification based on the result, construct a machine-readable code based on the test identification and the user identification, and incorporate the code into a digital pass, and means for displaying the digital pass.

Example 64 includes the device of Example 63, wherein the generating means is to incorporate an expiration date into the digital pass. The device further includes means for determining a validity of the digital pass based on the expiration date, and means for prompting scheduling of a test when the time comparator determines the digital pass is not valid.

Example 65 is an apparatus to generate a digital pass. The apparatus includes processor circuitry and a memory including instructions which, when executed, cause the processor circuitry to: determine a result of a diagnostic test, generate a code, the generating means to: access a test identification based on the result, access a user identification based on the result, construct a machine-readable code based on the test identification and the user identification, and incorporate the code into a digital pass, and display the digital pass.

Example 66 includes the apparatus of Example 65, wherein the instructions, when executed, cause the processor circuitry to: incorporate an expiration date into the digital pass, determine a validity of the digital pass based on the expiration date, and prompt scheduling of a test when the time comparator determines the digital pass is not valid.

Example 67 includes a non-transitory computer readable storage medium including instructions which, when executed, cause one or more processors to at least: determine a result of a diagnostic test, generate a code, the generating means to: access a test identification based on the result, access a user identification based on the result, construct a machine-readable code based on the test identification and the user identification, incorporate the code into a digital pass, and display the digital pass.

Example 68 includes the computer readable storage medium of Example 67, wherein the instructions, when executed, cause the one or more processors to: incorporate an expiration date into the digital pass; determine a validity of the digital pass based on the expiration date, and prompt scheduling of a test when the time comparator determines the digital pass is not valid.

Example 69 includes a method to create a digital pass. The method includes determining, by executing instructions with a processor, a result of a diagnostic test, generating, by executing instructions with the processor, a code, the generating means to: accessing, by executing instructions with the processor, a test identification based on the result, accessing, by executing instructions with the processor, a user identification based on the result, constructing, by executing instructions with the processor, a machine-readable code based on the test identification and the user identification, incorporating, by executing instructions with the processor, the code into a digital pass, and displaying, by executing instructions with the processor, the digital pass.

Example 70 includes the method of Example 69, further including: incorporating, by executing instructions with the processor, an expiration date into the digital pass, determining, by executing instructions with the processor, a validity of the digital pass based on the expiration date, and prompting, by executing instructions with the processor, scheduling of a test when the time comparator determines the digital pass is not valid.

Example 71 is a server to distribute first instructions on a network. The server includes at least one storage device including second instructions, and at least one processor to execute the second instructions to transmit the first instructions over the network. The first instructions, when executed, to cause at least one device to at least: determine a result of a diagnostic test, generate a code, the generating means to: access a test identification based on the result, access a user identification based on the result, construct a machine-readable code based on the test identification and the user identification, incorporate the code into a digital pass, and display the digital pass.

Example 72 includes the server of Example 71, wherein the first instructions, when executed, to cause at least one device to further: incorporate an expiration date into the digital pass, determine a validity of the digital pass based on the expiration date, and prompt scheduling of a test when the time comparator determines the digital pass is not valid.

Example 73 includes a system that includes a first non-transitory computer readable storage medium including a first set of instructions which, when executed, cause at least a first processor to at least: generate a record of a test result of a medical diagnostic test of a biological sample from a user, and transmit the test result to a second processor. The system also includes a second non-transitory computer readable storage medium including a second set of instructions which, when executed, cause at least the second processor to at least: generate a machine-readable code based on the test result and user identification, incorporate the code into a digital pass, and display the digital pass. The system further includes a third non-transitory computer readable storage medium including a third set of instructions which, when executed, cause at least a third processor to at least: scan the digital pass, and verify the test result.

Example 74 includes the system of Example 73, wherein the machine-readable code is a first machine readable code, the second instructions, when executed, cause the second device to: generate a second machine-readable code based on the user identification, and display the second machine-readable code; and the first instructions, when executed, cause a fourth device to: scan the second-machine readable code, and associate the user identification is a test kit and the biological sample.

Example 75 is a server to distribute first, second, and third instructions over a network. The server includes at least one storage device including fourth instructions, and at least one processor to execute the fourth instructions to: transmit the first instructions over the network to a first device, transmit the second instructions over the network to a second device, and transmit the third instructions over the network to a third device. The first instructions, when executed, to cause the first device to: generate a record of a test result of a medical diagnostic test of a biological sample from a user, and transmit the test result to the second device. The second instructions, when executed, to cause the second device to: generate a machine-readable code based on the test result and user identification, incorporate the code into a digital pass, and display the digital pass. The third instructions, when executed, to cause the third device to: scan the digital pass, and verify the test result.

Example 76 includes the server of Example 75, wherein the wherein the machine-readable code is a first machine readable code, the second instructions, when executed, cause the second device to: generate a second machine-readable code based on the user identification, and display the second machine-readable code; and the first instructions, when executed, cause a fourth device to: scan the second-machine readable code, and associate the user identification is a test kit and the biological sample.

Example 77 is device including any feature described, either individually or in combination with any feature, in any configuration.

Example 78 is a system including any feature described, either individually or in combination with any feature, in any configuration.

Example 79 is a server to transmit instructions to perform any method disclosed herein.

Example 80 is a method to operate any device, system, processor, or server disclosed herein.

Example 71 is a non-transitory computer readable storage medium including instructions which, when executed, cause at least one or more processors to perform any method or function disclosed herein.

Although certain example methods, apparatus, systems, and articles of manufacture have been disclosed herein, the scope of coverage of this patent is not limited thereto. On the contrary, this patent covers all methods, apparatus, systems, and articles of manufacture fairly falling within the scope of the claims of this patent.

The following claims are hereby incorporated into this Detailed Description by this reference, with each claim standing on its own as a separate embodiment of the present disclosure.

What is claimed is:

1. A server to distribute instructions over a network, the server comprising:
    at least one storage device including first instructions to be executed by first processor circuitry of a mobile device carried by a person;
    second instructions in the server; and
    second processor circuitry to execute the second instructions to transmit the first instructions over the network to the mobile device,
    the first instructions, when executed, to cause the first processor circuitry of the mobile device to at least:
        access a result of a diagnostic test for an infectious disease performed on the person;
        cause presentation of the result on a display of the mobile device;
        generate a digital pass in response to the result being negative for the infectious disease,
        store the digital pass in a memory of the mobile device;
        cause presentation, at a first time, of the digital pass on the display to enable the person to gain access to a location;
        cause presentation, at a second time subsequent to the first time, of a plurality of health questions on the display associated with symptoms of the infectious disease;
        receive answers to the health questions from the person; and
        prevent, at a third time subsequent to the second time, the digital pass from being presented on the display if one or more of the answers to the health questions indicate the person has at least one symptom of the infectious disease.

2. The server of claim 1, wherein the infectious disease is a disease caused by a coronavirus.

3. The server of claim 1, wherein the first instructions, when executed, cause the first processor circuitry of the mobile device to cause presentation of the health questions on the display on a daily basis.

4. The server of claim 1, wherein the first instructions, when executed, cause the first processor circuitry of the mobile device to cause presentation of a notification to the person on the display to take another diagnostic test based on one or more of the answers to one or more of the health questions.

5. The server of claim 1, wherein the first instructions, when executed, cause the first processor circuitry of the mobile device to delete the digital pass after a threshold number of days since the diagnostic test.

6. The server of claim 1, wherein the answers are first answers, and wherein the first instructions, when executed, cause the first processor circuitry of the mobile device to:
    cause presentation, at a fourth time subsequent to the third time, of the health questions on the display;
    receive second answers to the health questions from the person; and
    cause presentation, at a fifth time subsequent to the fourth time, of the digital pass based on the second answers to the health questions.

7. The server of claim 1, wherein the digital pass includes a machine-readable code.

8. The server of claim 7, wherein the machine-readable code includes a user identification associated with the person and a test kit identification associated with a test kit used to perform the diagnostic test.

9. The server of claim 8, wherein the first instructions, when executed, cause the first processor circuitry of the mobile device to cause a camera of the mobile device to scan a test kit code on the test kit to obtain the test kit identification.

10. The server of claim 8, wherein the machine-readable code is a Quick Response code.

11. One or more non-transitory computer readable medium comprising instructions that, when executed, cause one or more processors in a user device carried by a person to at least:
- access a result of a diagnostic test for an analyte of interest performed on a sample gathered from the person;
- cause presentation of the result on a display of the user device;
- generate a digital pass in response to the result being negative for the analyte of interest;
- store the digital pass in a memory of the user device;
- cause presentation, at a first time, of the digital pass on the display to enable the person to gain access to a location;
- cause presentation, at a second time subsequent to the first time, of a plurality of health questions on the display associated with symptoms of being ill;
- access answers to the health questions from the person; and
- deactivate, at a third time subsequent to the second time, the digital pass display based on one or more of the answers to one or more of the health questions.

12. The one or more non-transitory computer readable medium of claim 11, wherein the analyte of interest is an infectious disease.

13. The one or more non-transitory computer readable medium of claim 11, wherein the analyte of interest is a COVID-19 antibody.

14. The one or more non-transitory computer readable medium of claim 11, wherein the instructions, when executed, cause the one or more processors to cause presentation of the health questions on the display on a daily basis.

15. The one or more non-transitory computer readable medium of claim 11, wherein the instructions, when executed, cause the one or more processors to cause presentation of a notification to the user on the display to take another diagnostic test based on the answers to the health questions.

16. The one or more non-transitory computer readable medium of claim 11, wherein the instructions, when executed, cause the one or more processors to delete the digital pass after a threshold number of days since the diagnostic test.

17. The one or more non-transitory computer readable medium of claim 11, wherein the answers are first answers, and wherein the instructions, when executed, cause the one or more processors to:
- cause presentation, at a fourth time subsequent to the third time, of the health questions on the display;
- receive second answers to the health questions from the person; and
- cause presentation, at a fifth time subsequent to the fourth time, of the digital pass based on the second answers to the health questions.

18. The one or more non-transitory computer readable medium of claim 11, wherein the digital pass includes a machine-readable code.

19. The one or more non-transitory computer readable medium of claim 18, wherein the machine-readable code includes a user identification associated with the person and a test kit identification associated with a test kit used to perform the diagnostic test.

20. The one or more non-transitory computer readable medium of claim 18, wherein the machine-readable code is a Quick Response code.

* * * * *